(12) United States Patent
Thomas et al.

(10) Patent No.: US 8,835,648 B2
(45) Date of Patent: *Sep. 16, 2014

(54) HEDGEHOG PATHWAY ANTAGONISTS AND THERAPEUTIC APPLICATIONS THEREOF

(75) Inventors: J. Russell Thomas, Siena (IT); Gal.la Pericot Mohr, Siena (IT); Chiara Caramelli, Siena (IT); Giacomo Minetto, Siena (IT); Marta Bellini, Siena (IT)

(73) Assignee: Siena Biotech S.p.A., Siena (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/377,290

(22) PCT Filed: Jun. 9, 2010

(86) PCT No.: PCT/EP2010/003441
§ 371 (c)(1),
(2), (4) Date: Dec. 9, 2011

(87) PCT Pub. No.: WO2010/142426
PCT Pub. Date: Dec. 16, 2010

(65) Prior Publication Data
US 2012/0088752 A1    Apr. 12, 2012

(30) Foreign Application Priority Data
Jun. 11, 2009    (EP) .................... 09007726

(51) Int. Cl.
| | | |
|---|---|---|
| *C07D 403/14* | (2006.01) | |
| *C07D 413/14* | (2006.01) | |
| *C07D 471/04* | (2006.01) | |
| *C07D 401/12* | (2006.01) | |
| *C07D 403/12* | (2006.01) | |

(52) U.S. Cl.
CPC ............ *C07D 471/04* (2013.01); *C07D 413/14* (2013.01); *C07D 401/12* (2013.01); *C07D 403/12* (2013.01)

USPC ........ 548/310.7; 540/597; 544/129; 544/139; 544/364; 544/370; 546/118; 546/187; 546/199; 514/217.04; 514/235.5; 514/253.13; 514/255.01; 514/303; 514/316; 514/322; 514/394

(58) Field of Classification Search
USPC ...................................................... 548/310.7
See application file for complete search history.

(56) References Cited

U.S. PATENT DOCUMENTS

2010/0286114 A1*   11/2010   Thomas et al. .......... 514/210.18

FOREIGN PATENT DOCUMENTS

| EP | 1 391 457 A1 | 2/2004 |
|---|---|---|
| WO | WO 03/011219 A2 | 2/2003 |
| WO | WO 2009/074300 A2 | 6/2009 |

OTHER PUBLICATIONS

Golub et al., Science, vol. 286, Oct. 15, 1999, pp. 531-537.*
Cheng et al., Journal of the Pancreas, Jul. 2011, vol. 12, No. 4, pp. 334-338.*
Matthews et al., Cancer Res. (2007), vol. 67(6), pp. 2430-2438.*
Thomas et al., Chemical Abstract 151:56875, 2009.*
Gary V. Borzillo, et al., "The Hedgehog Signaling Pathway As a Target for Anticancer Drug Discovery", Current Topics in Medicinal Chemistry, Bentham Science Publishers Ltd., Netherlands, vol. 5, No. 2, Jan. 1, 2005, pp. 147-157.
Anita Buttner, et al., "Synthesis and Biological Evaluation of SANT-2 and Analogues As Inhibitors of the Hedgehog Signaling Pathway", Bioorganic & Medicinal Chemistry, Pergamon, GB, vol. 17, No. 14, Jul. 15, 2009, pp. 4943-4954.

* cited by examiner

*Primary Examiner* — Laura L. Stockton
(74) *Attorney, Agent, or Firm* — Arent Fox LLP

(57) ABSTRACT

Heterocyclic compounds that modulate the hedgehog signaling pathway, pharmaceutical composition thereof and their therapeutic applications.

17 Claims, No Drawings

HEDGEHOG PATHWAY ANTAGONISTS AND THERAPEUTIC APPLICATIONS THEREOF

CROSS-REFERENCE TO RELATED APPLICATION

This Application is a National Stage entry of International Application No. PCT/EP2010/003441, having an international filing data of Jun. 9, 2010; which claims priority to European Application No.: 09007726.4, filed Jun. 11, 2009.

FIELD OF THE INVENTION

The present invention relates to organic compounds, pharmaceutical compositions thereof and their use for therapy and/or prophylaxis in a mammal, in particular to heterocyclic compounds that modulate the hedgehog signaling pathway.

BACKGROUND OF THE INVENTION

Autoproteolysis of a 45 kDa Human Shh precursor protein gives a 20 kDa N-terminal fragment that is responsible for normal hedgehog signalling and a 25 kDa C-terminal fragment involved in autoprocessing activity in which the N-terminal fragment is conjugated to cholesterol (Lee et al. Science 266 1528-1537 (1994) and Bumcrot et al. Mol. Cell. Biol. 15 2294-2303 (1995)).

Normally functioning Hedgehog (Hh) signaling specifies embryonic pattern by directing cellular differentiation and proliferation, which was first reported in *Drosophila melanogaster* (Nusslein-Vollhard et al. Roux. Arch. Dev. Biol. 193: 267-282 (1984)). Cellular responses to the secreted Hh polypeptide are mediated by two integral membrane proteins, Patched (Ptc) and Smoothened (Smo). Hh binds to the twelve transmembrane protein Ptc and hence reverses the Ptc-mediated suppression of the seven transmembrane protein Smo. This Smo activation then triggers a series of intracellular events, culminating in the stabilization of the transcription factor Cubitus interruptus (Ci) and the expression of Ci-dependent genes. These events are recapitulated during mammalian development and tumourigenesis through multiple protein homologues, including three distinct Hh family members [Sonic (Shh), Indian (Ihh), and Desert (Dhh)], two Ptc proteins (Ptch1 and Ptch2), and three Ci-like transcription factors (Gli1, Gli2, and Gli3). However, there is a single vertebrate homologue of Smo, which is implicated in all forms of Hh signaling by genetic analyses in *Drosophila*, mice, and zebrafish (Chen et al. PNAS 99(22): 14071-14076 (2002)).

Smo initiates a signal cascade causing the activation of Gli transcription factors and their subsequent nuclear translocation resulting in the control of transcription of target genes. Through a negative feedback loop, Gli influences transcription of Ptc and Hip 1 (hedgehog-interacting protein 1 (Hip1)) which inhibit the Hh pathway. The loss of control over the activation of the Hh pathway has been associated with an increasing range of cancers including those affecting the brain such as medulloblastoma (Romer and Curran, Cancer Res 65(12) 4975-4978 (2005)) and glioblastoma (Bar et al. Stem Cells 25(10):2524-33 (2007)); prostate cancer (Sanchez et al. PNAS 101(34) 12561-12566 (2004)); pancreatic cancer (Thayer et al. Nature 423 851-856 (2003)); non-small cell lung carcinoma (Yuan et al. Oncogene 26 1046-1055 (2007); small-cell lung cancer (Watkins et al. Nature 422 313-317 (2003)); breast cancer (Kubo et al. Cancer Res 64 6071-6074 (2004)); various digestive tract tumours (Berman et al. Nature 425 846-851 (2003)) and (Lees et al. Gastroenterology 129(5) 1696-1710 (2006)); basal cell carcinoma (Williams et al. PNAS 100(8) 4616-4621 (2003)); malignant melanoma (Pons and Quintanilla Clin Trans Oncol. 8(7) 466-474 (2006)); squamous cell carcinomas (Xuan et al. Mod Pathol. 19(8) 1139-47 (2006)); B-cell malignancies such as multiple myeloma and lymphomas (Dierks et al. Nat. Med. 13(8) 944-951 (2007); Peacock et al. PNAS 104(10) 4048-4053 (2007)); mesenchymal cancers such as chondrosarcoma (Tiet et al. Am. J. Pathol. 168(1) 321-330 (2006)), clear cell sarcoma of the kidney (Cutcliffe et al. Clin Cancer Res. 11(22): 7986-94 (2005)) and rhabdomyosarcoma (Tostar et al. J. Pathol. 208(1) 17-25 (2006)); chronic myeloid leukaemia (Sengupta et al. Leukemia 21(5) 949-955 (2007)); endometrial carcinoma (Feng et al. Clin. Cancer Res. 13(5) 1389-1398 (2007); hepatocellular carcinomas (Huang et al. Carcinogenesis 27(7) 133401340 (2006)); ovarian tumours (Chen et al. Cancer Sci. 98(1) 68-76 (2007)).

It has also been found that Hh signaling regulates the expression of the ABC transporter proteins multi-drug resistance protein-1 (MDR1, ABCB1, P-glycoprotein) and (BCRP, ABCG2), and that targeted knockdown of MDR1 and BCRP expression by small interfering RNA partially reverses Hh-induced chemoresistance. This would suggest that the Hh pathway may be a target to overcome MDR and increase chemotherapeutic response (Sims-Mourtada et al Oncogene 26(38) 5674-5679 (2007)). The blockade of sonic hedgehog signal pathway was found to enhance the antiproliferative effect of EGFR inhibitors in pancreatic cancer cells (Hu et al. Acta Pharmacol Sin. 28(8) 1224-30 (2007)) and prostate cancer cells (Mimeault et al. Int. J. Cancer 118(4) 1022-31 (2006)).

The hedgehog pathway has also been associated to tumour regrowth after chemoradiotherapy and as a potential target to improve radiation response (Sims-Mourtada et al. Clin. Cancer Res. 12(21) 6565-6572 (2006)) and cyclopamine, a hedgehog pathway antagonist, increases the cytotoxic effects of paclitaxel and radiation in Hh expressing pancreatic cancer cells (Shafaee et al. Cancer Chemother. Pharmacol. 58(6) 765-70 (2006)).

It has also been reported that the inhibition of the Hedgehog signalling pathway may be of use for the treatment of a range of diseases related to inflammation, epithelial cell hyperplasia, fibrosis of tissue or immune disorders (Lamb et al. EP1183040). Inhibition of sonic hedgehog signaling has been reported to reduce chronic rejection and prolong allograft survival in a rat orthotopic small bowel transplantation model. Although acute graft rejection can be controlled by immunosuppressive agents, chronic rejection, which is characterized by arteriosclerosis in the donor organ vessels, is a major hurdle to long-term allograft survival. Graft survival in a rat orthotopic small bowel transplantation model was significantly prolonged after anti-Shh antibody treatment compared with the immunoglobulin G control (116 vs. 77.5 days). Collagen deposition and vascular occlusion in the mesentery were markedly reduced in recipients of the anti-Shh antibody (Chen et al. Transplantation 83(10) 1351-1357 (2007); Lamb et al. EP1183040B1).

It has also been reported that sFRP-1 is the downstream target gene of Hh signaling and that elevated expression of secreted frizzled related protein-1 (sFRP-1) following activation of the Hh pathway provides the molecular link for the inhibitory effect on Wnt signaling (He et al. J. Biol. Chem. 281(47)35598-35602 (2006)). Thus the modulation of Wnt signaling by antagonising Hh pathway through sFRP-1 could provide a method for the treatment of a range of diseases such as osteoporosis (Ai et al. Mol. Cell. Biol. 25(12) 4946-4955 (2005)) among others (Luo et al. Laboratory Investigation, 87, 97-103-(2007)).

Various inhibitors of the Hh pathway have been investigated, including the natural product cyclopamine, which is believed to act by binding to the heptahelical region of Smo. Additionally a number of synthetic small molecule antagonists of the Smo receptor have been reported in recent years: for a review see Kiselyov Anti-Cancer Agents in Medicinal Chemistry 6 445-449 (2006).

PRIOR ART

Lubisch et al. disclose a series of 2-phenyl-benzimidazoles as PARP inhibitors for useful for the cure of various diseases including cancer (WO2000026192) and in the field of cosmetics (WO2001082877). A recurring feature is the presence of a carbamoyl moiety at the 4-position of the benzimidazole ring.

Arienti et al. (WO2003032984) and Ameriks et al. (WO2004093873 and US2004214857) disclose a series of 2-phenyl-benzimidazole derivatives as checkpoint kinase 2 inhibitors for the cure of cancer, further characterised in that the 5-position of the benzimidazole ring is always substituted with either a carboxylate, a carbamoyl or a sulphamoyl group.

Ohemeng et al. (WO9911627 and U.S. Pat. No. 5,942,532) disclose a series of 5-carboxylmidamides-2-phenyl-benzimidazoles compounds as antibacterial agents.

Mjalli et al. (WO2003075921) describe the pharmaceutical applications of a series of 2-phenyl-benzimidazole derivatives.

Alekshun et al. (WO2004041209 and WO2006076009) disclose a series of 2-phenyl-benzimidazolol derivatives with antibiotic activity.

Khaled et al.[1] (Bulletin of the Faculty of Pharmacy (Cairo University), 40(1), 7-13, (2002)) describe the synthesis and antihypertensive activity of 2-phenyl-benzimidazoles derivatives whereas the DNA binding properties of some others are described by Kobuta et al. (Nucleic Acids Research Supplement, 2(Twenty-ninth Symposium on Nucleic Acids Chemistry), 193-194 (2002) and Nucleic Acids Symposium Series, 35(Twenty-third Symposium on Nucleic Acids Chemistry, 1996), 151-152 (1996)).

Guicherit et al. (WO2006050506), Beachy et al. (WO2003088970), Rubin et al. (WO2003011219), Yuach et al. (Nature, 455, 406 (2008) and Dakin et al. (WO2009027746) disclose Aryl- and alkyl-amido/ureido derivatives of 2-phenyl-benzimidazole as Hedgehog pathway antagonists for the cure of various forms of cancer. Guicherit et al. (WO2006050506) and Rubin et al. (WO2003011219) also disclose arylamido derivatives of 2-phenyl-imidazopyridine for the same purpose. The following 22 compounds are disclosed in co-pending application WO2009074300, in the name of the same applicant.

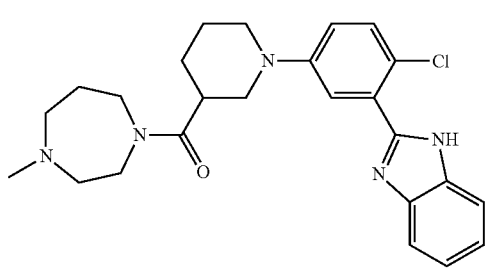

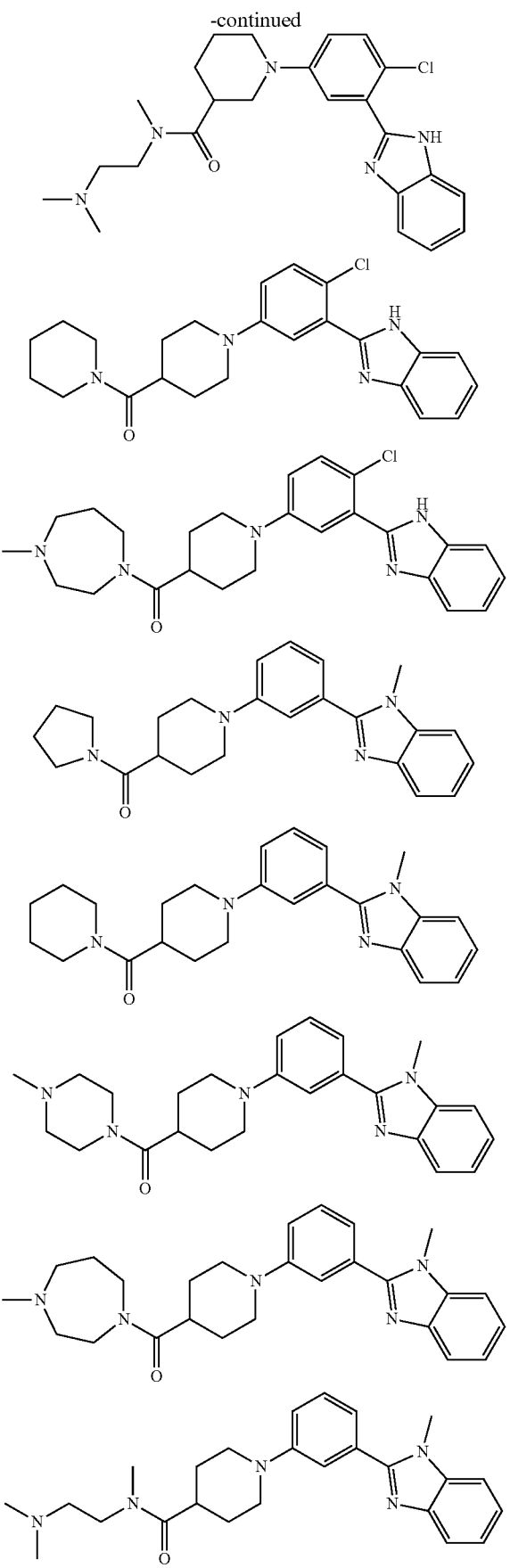

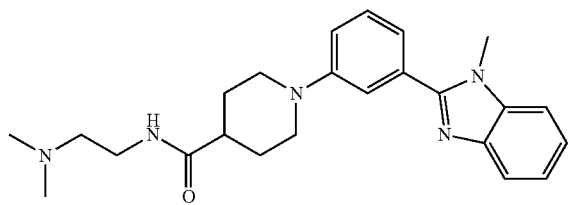
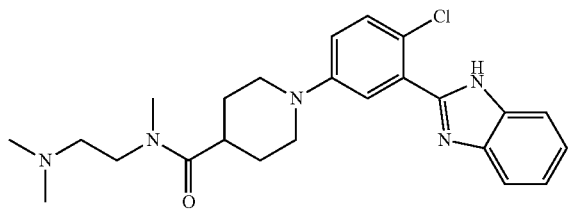
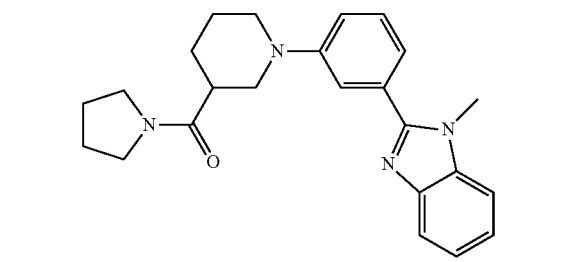
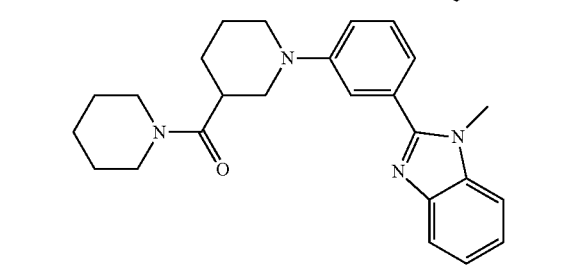
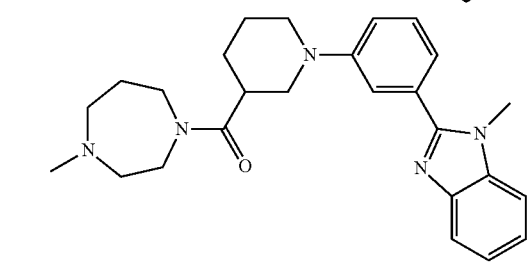
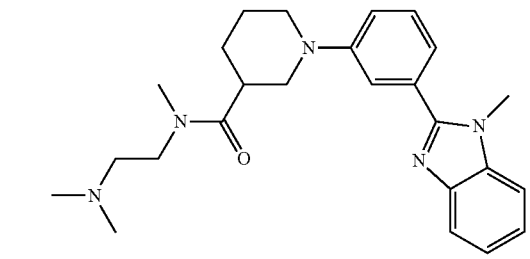
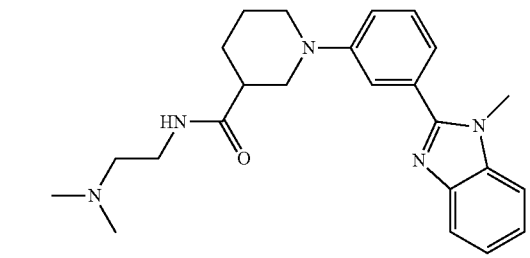
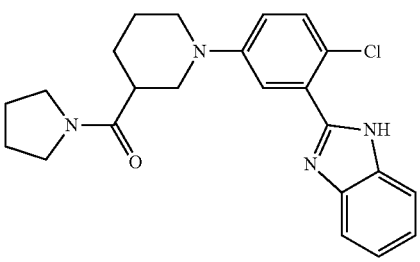
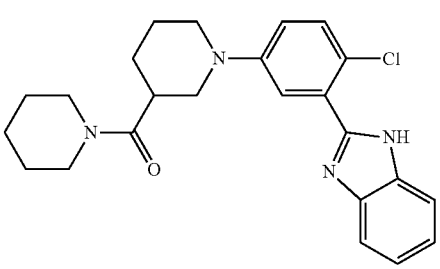
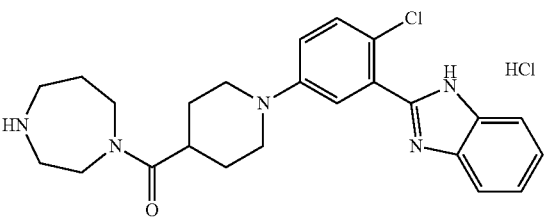
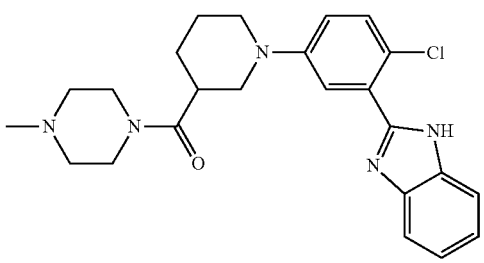
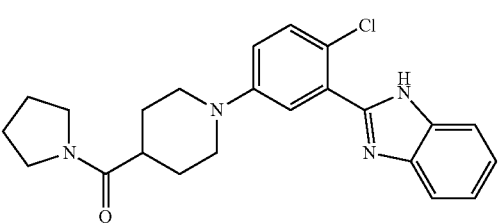
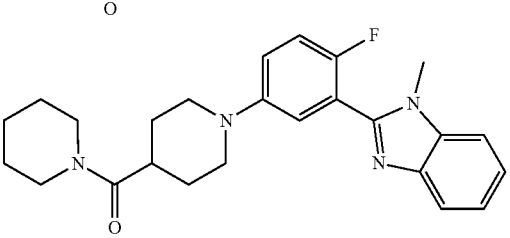

DETAILED DESCRIPTION OF THE INVENTION

This invention provides compounds of formula I

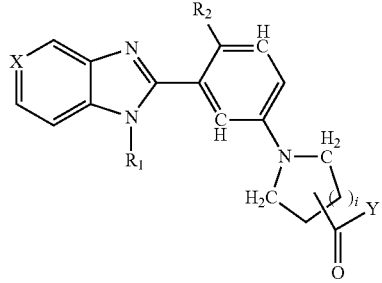

Wherein, as valence and stability permit i may be 1 or 2

$R_1$ may be H; linear, branched or cyclic ($C_1$-$C_4$) alkyl group $R_2$ can be H, Cl or F X can be either N or $CR_3$ $R_3$ may be H; halogen; a linear, branched or cyclic ($C_1$-$C_4$) alkyl or alkoxy group, Y may be

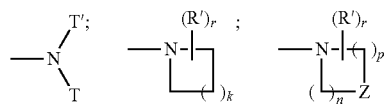

Z may be O or NRx

Rx may be H or a linear, branched or cyclic ($C_1$-$C_4$) alkyl k may be 1, 2, 3 or 4 n and p may independently be 1, 2 or 3 and the sum n+p cannot exceed 5

T may be H or a linear or branched ($C_1$-$C_4$) alkyl group;

T' may be a linear or branched $C_1$-$C_3$ alkyl chain substituted with either a ($C_1$-$C_6$)-dialkylamino group or a 4 to 6 membered saturated heterocycle containing one nitrogen atom and optionally containing a second heteroatom selected from N and O, such heterocyclic ring being optionally substituted a the nitrogen atoms with a ($C_1$-$C_4$) alkyl chain; or a 4 to 6 membered saturated heterocycle containing one nitrogen atom and optionally containing a second heteroatom selected from N and O, such heterocyclic ring being optionally substituted at the nitrogen atoms with a ($C_1$-$C_4$) alkyl chain r may be zero, 1, 2 or 3;

R' may be halogen; hydroxy; amino; cyano; nitro; oxo; linear, or branched ($C_1$-$C_6$) alkyl, dihaloalkyl, azaalkyl, oxaalkyl, alkylcarbonyl, oxaalkylcarbonyl, alkoxycarbonyl, alkylaminocarbonyl, alkylcarbonylamino, alkenyl, oxaalkenyl, azaalkenyl, alkenylcarbonyl, oxaalkenylcarbonyl, alkenyloxycarbonyl, alkenylaminocarbonyl, alkylamino, dialkylamino, mercaptoalkyl, alkoxy, alkylthio group optionally substituted with one or more fluorine atoms; wherein two R' groups may form a 5- to 8-membered ring with spiro or fused junction.

And with the exclusion of:

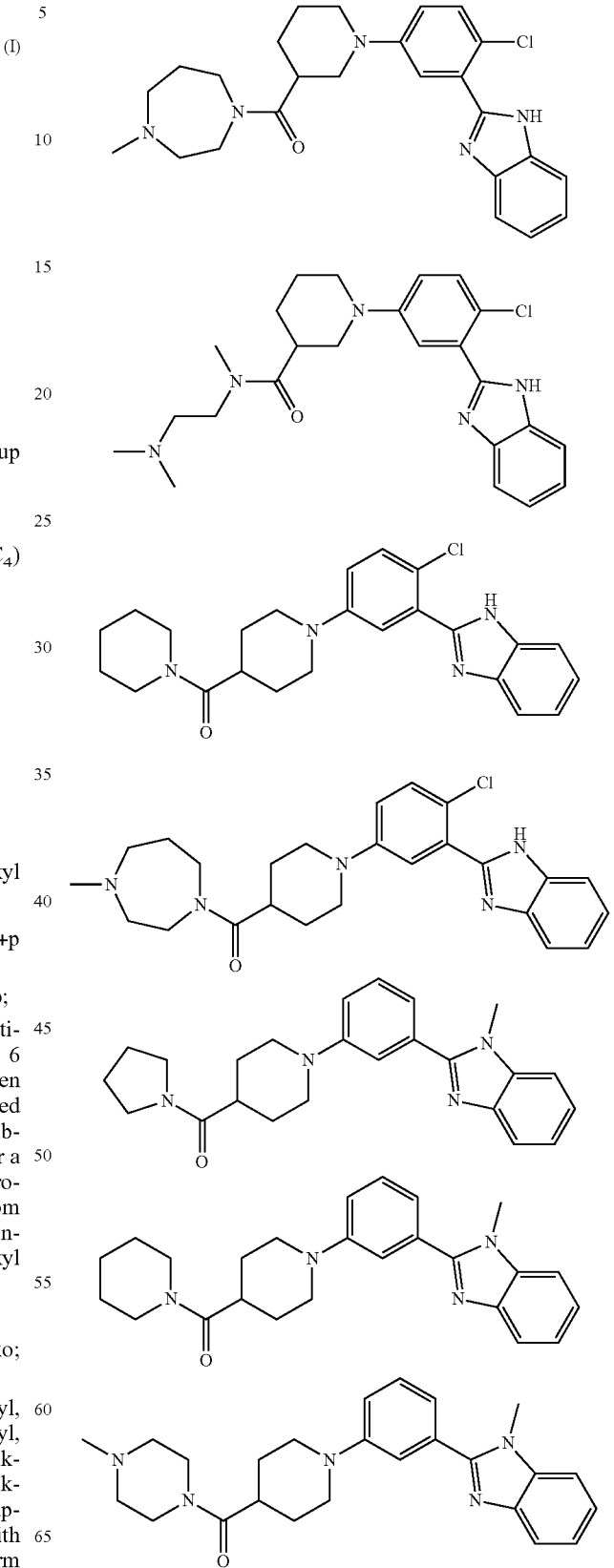

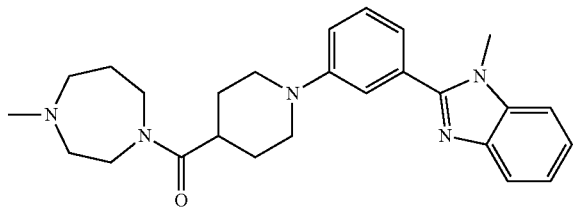
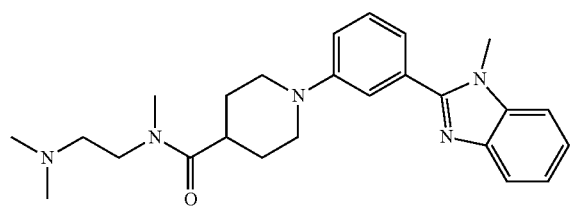
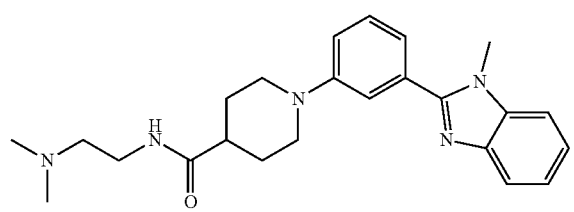
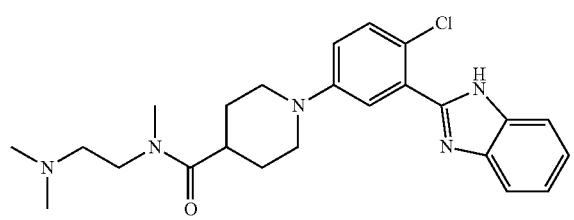
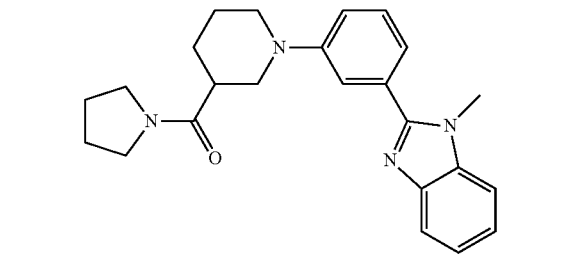
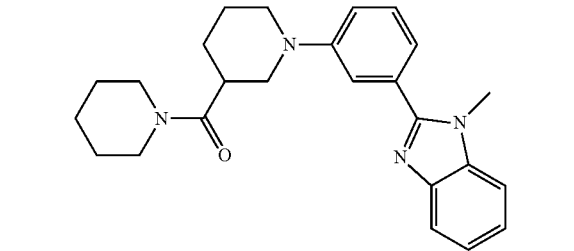
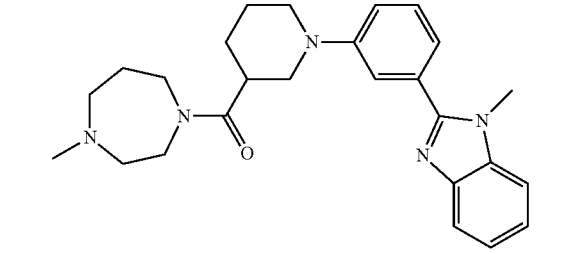
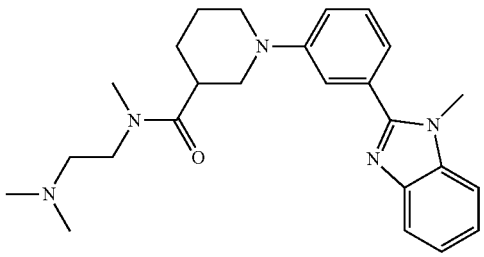
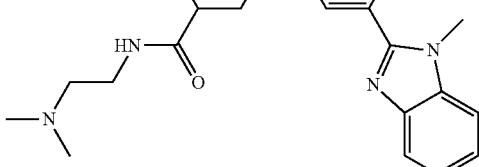
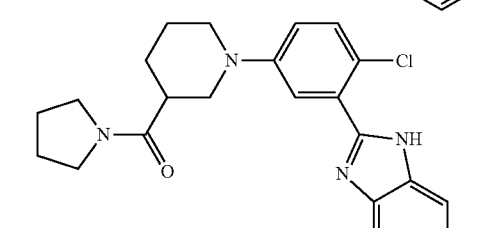
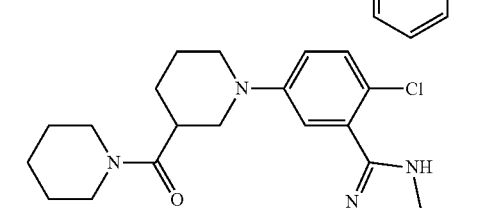
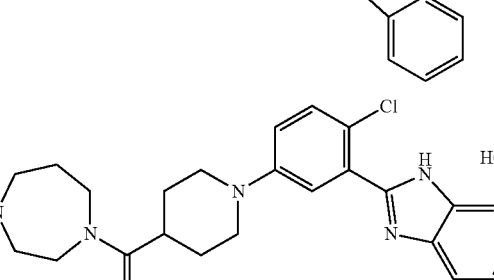
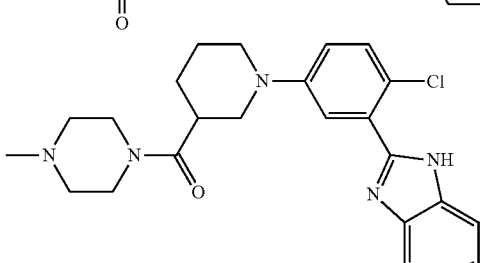
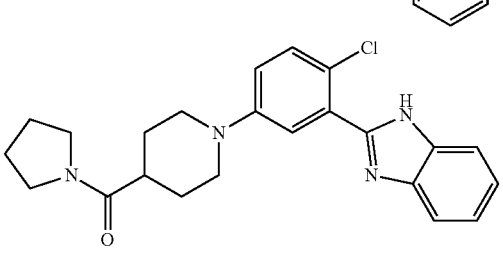

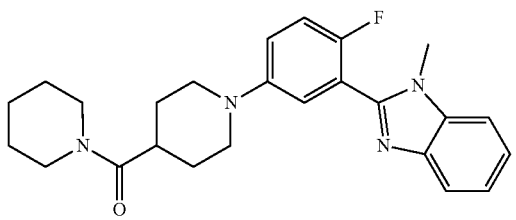

In one embodiment, i equals 2, —C(=O)-Y stands in the 4 position of the ensuing piperidine ring and $R_1$, $R_2$, X, $R_3$, Y, Z, Rx, k, n, p, T, T', r and R' are as defined under formula I above. In another embodiment i equals 2, —C(=O)-Y stands in the 3 position of the ensuing piperidine ring and $R_1$, $R_2$, X, $R_3$, Y, Z, Rx, k, n, p, T, T', r and R' are as defined under formula I above; in other embodiment, i equals 1 and $R_1$, $R_2$, X, $R_3$, Y, Z, Rx, k, n, p, T, T', r and R' are as defined under formula I above; in one embodiment, $R_1$ is H, $R_2$ is not H and i, X, $R_3$, Y, Z, Rx, k, n, p, T, T', r and R' are as defined under formula I above; in another embodiment, $R_2$ is H, $R_1$ is not H and i, X, $R_3$, Y, Z, Rx, k, n, p, T, T', r and R' are as defined under formula I above. In one embodiment X is N and i, $R_1$, $R_2$, $R_3$, Y, Z, Rx, k, n, p, T, T', r and R' are as defined under formula I above; in another embodiment X is $CR_3$ and i, $R_1$, $R_2$, $R_3$, Y, Z, Rx, k, n, p, T, T', r and R' are as defined under formula I above. In one embodiment, $R_3$ is H and i, $R_1$, $R_2$, Y, Z, Rx, k, n, p, T, T', r and R' are as defined under formula I above. In another embodiment, $R_3$ is Cl, F, OMe and Me and i, $R_1$, $R_2$, Y, Z, Rx, k, n, p, T, T', r and R' are as defined under formula I above. In another embodiment r equals zero and i, $R_1$, $R_2$, X, $R_3$, Y, Z, Rx, k, n, p, T and T' are as defined under formula I above In a preferred embodiment, there is provided compounds of formula I above wherein Y is

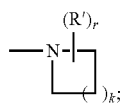

k equals 2, r equals 1, R' is dimethylamino and i, $R_1$, $R_2$, X, and $R_3$ are as defined under formula I above In a second preferred embodiment, there is provided compounds of formula I above wherein Y is

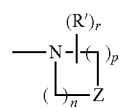

and wherein both n and p equal 2, Z is O, r equals zero and i, $R_1$, $R_2$, X, and $R_3$ are as defined under formula I above In a third preferred embodiment, there is provided compounds of formula I above wherein i equals 2 and —C(=O)-Y stands in the 4 position of the ensuing piperidine ring, X is $CR_3$, $R_3$ is methyl, $R_2$ is F and $R_1$, Y, Z, Rx, k, n, p, T, T', r and R' are as defined under formula I above Particularly interesting compounds are the following:

{1-[4-Fluoro-3-(5-methyl-1H-benzoimidazol-2-yl)-phenyl]-piperidin-4-yl}-piperazin-1-yl-methanone;

Azepan-1-yl-{1-[4-fluoro-3-(5-methyl-1H-benzoimidazol-2-yl)-phenyl]-piperidin-4-yl}-methanone;

{1-[4-Fluoro-3-(5-methyl-1H-benzoimidazol-2-yl)-phenyl]-piperidin-4-yl}-pyrrolidin-1-yl-methanone;

{1-[4-Fluoro-3-(5-methyl-1H-benzoimidazol-2-yl)-phenyl]-piperidin-4-yl}-piperidin-1-yl-methanone;

{(S)-1-[3-(1H-Benzoimidazol-2-yl)-4-chloro-phenyl]-piperidin-3-yl}-morpholin-4-yl-methanone;

{1-[3-(1H-Benzoimidazol-2-yl)-4-chloro-phenyl]-piperidin-4-yl}-morpholin-4-yl-methanone;

1-[4-Fluoro-3-(5-methyl-1H-benzoimidazol-2-yl)-phenyl]-piperidine-4-carboxylic acid (3-dimethylamino-propyl)-methyl-amide {1-[4-Fluoro-3-(5-methyl-1H-benzoimidazol-2-yl)-phenyl]-piperidin-4-yl}-(4-methyl-piperazin-1-yl)-methanone;

{1-[4-Fluoro-3-(5-methyl-1H-benzoimidazol-2-yl)-phenyl]-piperidin-4-yl}-(4-pyrrolidin-1-yl-piperidin-1-yl)-methanone;

{1-[4-Fluoro-3-(5-methyl-1H-benzoimidazol-2-yl)-phenyl]-piperidin-4-yl}-morpholin-4-yl-methanone;

{1-[4-Chloro-3-(5-methoxy-1H-benzoimidazol-2-yl)-phenyl]-piperidin-4-yl}-morpholin-4-yl-methanone;

{(R)-1-[3-(1H-Benzoimidazol-2-yl)-4-chloro-phenyl]-piperidin-3-yl}-morpholin-4-yl-methanone;

{(S)-1-[3-(1-Methyl-1H-Benzoimidazol-2-yl)-phenyl]-piperidin-3-yl}-morpholin-4-yl-methanone;

{(R)-1-[3-(1-Methyl-1H-Benzoimidazol-2-yl)-phenyl]-piperidin-3-yl}-morpholin-4-yl-methanone;

{1-[4-Fluoro-3-(5-fluoro-1H-benzoimidazol-2-yl)-phenyl]-piperidin-4-yl}-morpholin-4-yl-methanone;

(3-Dimethylamino.pyrrolidin-1-yl)-{(R)-1-[3-(1-methyl-1H-benzoimidazol-2-yl-)-phenyl]-piperidin-3-yl}-methanone;

{(R)-1-[4-Chloro-3-(5-methyl-1H-benzoimidazol-2-yl)-phenyl]-piperidin-3-yl}-(3-dimethylamino-pyrrolidin-1-yl)-methanone;

{(S)-1-[4-Chloro-3-(5-methyl-1H-benzoimidazol-2-yl)-phenyl]-piperidin-3-yl}-morpholin-4-yl-methanone;

{1-[3-(1H-Benzoimidazol-2-yl)-4-chloro-phenyl]-pyrrolidin-3-yl}-(3-dimethylamino-pyrrolidin-1-yl)-methanone;

(3-Dimethylamino-pyrrolidin-1-yl)-{(S)-1-[3-(1-methyl-1H-benzoimidazol-2-yl)-phenyl]-piperidin-3-yl}-methanone;

(3-Dimethylamino-pyrrolidin-1-yl)-{(R)-1-[3-(1-methyl-1H-benzoimidazol-2-yl)-phenyl]-piperidin-3-yl}-methanone;

{(R)-1-[4-Chloro-3-(5-methyl-1H-benzoimidazol-2-yl)-phenyl]-piperidin-3-yl}-(3-dimethylamino-pyrrolidin-1-yl)-methanone;

{1-[4-Chloro-3-(5-methoxy-1H-benzoimidazol-2-yl)-phenyl]-pyrrolidin-3-yl}-morpholin-4-yl-methanone;

(3-Dimethylamino-pyrrolidin-1-yl)-{1-[3-(1-methyl-1H-benzoimidazol-2-yl)-phenyl]-pyrrolidin-3-yl}-methanone;

{(R)-1-[4-Chloro-3-(5-fluoro-1H-benzoimidazol-2-yl)-phenyl]-piperidin-3-yl}-(3-dimethylamino-pyrrolidin-1-yl)-methanone;

{(R)-1-[3-(1H-Benzoimidazol-2-yl)-4-chloro-phenyl]-piperidin-3-yl}-(3-dimethylamino-pyrrolidin-1-yl)-methanone;

{(R)-1-[4-Chloro-3-(5-methyl-1H-benzoimidazol-2-yl)-phenyl]piperidin-3-yl}-morpholin-4-yl-methanone;
{1-[4-Chloro-3-(5-methyl-1H-benzoimidazol-2-yl)-phenyl]-pyrrolidin-3-yl}-(3-dimethylamino-pyrrolidin-1-yl)-methanone;
{(S)-1-[4-Chloro-3-(5-fluoro-1H-benzoimidazol-2-yl)-phenyl]-piperidin-3-yl}-morpholin-4-yl-methanone;
{(S)-1-[3-(1H-Benzoimidazol-2-yl)-4-chloro-phenyl]-piperidin-3-yl}-(3-dimethylamino-pyrrolidin-1-yl)-methanone;
{1-[4-Chloro-3-(-1H-imidazo[4,5-c]pyridin-2-yl)-phenyl]-piperidin-4-yl}-morpholin-4-yl-methanone;
{(R)-1-[4-Chloro-3-(-1H-imidazo[4,5-c]pyridin-2-yl)-phenyl]-piperidin-3-yl}-morpholin-4-yl-methanone;
{(S)-1-[4-Chloro-3-(-1H-imidazo[4,5-c]pyridin-2-yl)-phenyl]-piperidin-3-yl}-morpholin-4-yl-methanone;
{1-[4-Chloro-3-(-1H-imidazo[4,5-c]pyridin-2-yl)-phenyl]-piperidin-4-yl}-(3-dimethylamino-pyrrolidin-1-yl)-methanone;
{(S)-1-[3-(1H-Benzoimidazol-2-yl)-4-chloro-phenyl]-piperidin-3-yl}-(3-dimethylamino-pyrrolidin-1-yl)-methanone;
{1-[4-Chloro-3-(5-fluoro-1H-benzoimidazol-2-yl)-phenyl]-piperidin-4-yl}-morpholin-4-yl-methanone;
{1-[4-Chloro-3-(5-fluoro-1H-benzoimidazol-2-yl)-phenyl]-piperidin-4-yl}-(3-dimethylamino-pyrrolidin-1-yl)-methanone;
and {1-[4-Chloro-3-(5-methyl-1H-benzoimidazol-2-yl)-phenyl]-piperidin-4-yl}-morpholin-4-yl-methanone The pharmacological activity of a representative group of compounds of formula I was demonstrated using the two in vitro assays described below. According to a further aspect, the invention is therefore directed to a method of treating cancer or osteoporosis which comprises administering to a subject, preferably a human subject in need thereof, an effective amount of a compound of formula I. Types of cancer that may be treated using such method not limitedly include non-small cell lung carcinoma; small-cell lung cancer; breast cancer; ovarian tumours; digestive tract tumours; brain cancers such as medulloblastoma and glioblastoma; prostate cancer; pancreatic cancer; basal cell carcinoma; malignant melanoma; squamous cell carcinomas; multiple myeloma; lymphomas; mesenchymal cancers such as chondrosarcoma, clear cell sarcoma of the kidney and rhabdomyosarcoma; chronic myeloid leukaemia; endometrial carcinoma; hepatocellular carcinomas.

In general, the compounds of formula I can be used to treat any disease, condition or dysfunction that may benefit from the inhibition of the Hedgehog pathway by binding of the compounds to the Smo receptor, and not limitedly including osteoporosis and cancers selected from non-small cell lung carcinoma; small-cell lung cancer; breast cancer; ovarian tumours; digestive tract tumours; brain cancers such as medulloblastoma and glioblastoma; prostate cancer; pancreatic cancer; basal cell carcinoma; malignant melanoma; squamous cell carcinomas; multiple myeloma; lymphomas; mesenchymal cancers such as chondrosarcoma, clear cell sarcoma of the kidney and rhabdomyosarcoma; chronic myeloid leukaemia; endometrial carcinoma; hepatocellular carcinomas.

The dosage of the compounds for use in therapy may vary depending upon, for example, the administration route, the nature and severity of the disease. In general, an acceptable pharmacological effect in humans may be obtained with daily dosages ranging from 0.01 to 200 mg/kg.

In yet a further aspect, the invention refers to a pharmaceutical composition containing one or more compounds of formula I, in association with pharmaceutically acceptable carriers and excipients. The pharmaceutical compositions can be in the form of solid, semi-solid or liquid preparations, preferably in form of solutions, suspensions, powders, granules, tablets, capsules, syrups, suppositories, aerosols or controlled delivery systems. The compositions can be administered by a variety of routes, including oral, transdermal, subcutaneous, intravenous, intramuscular, rectal and intranasal, and are preferably formulated in unit dosage form. Oral unit dosage forms may contain from about 1 mg to about 1000 mg of the compound of the invention.

For those compounds which can be in the form of free bases, this invention also includes their acid addition salts, preferably salts with pharmaceutically acceptable acids. The invention also includes separated isomers and diastereomers of compounds I, or mixtures thereof (e.g. racemic mixtures). The principles and methods for the preparation of pharmaceutical compositions are described for example in Remington's Pharmaceutical Science, Mack Publishing Company, Easton (PA).

The compounds of formula I, their optical isomers or diastereomers can be purified or separated according to well-known procedures, not limitedly including chromatography with a chiral matrix and fractional crystallisation.

Compounds Synthesis and Experimental Procedures

The compounds of the present invention can be prepared using various synthetic routes, including those described by general methods 1-11 and methods A-T below.

Materials and Methods

All reagents and solvents were obtained commercially. Air and moisture sensitive liquid solutions were transferred via syringe. The course of reactions was followed by thin-layer chromatography (TLC) and/or liquid chromatography-mass spectrometry (LC-MS).

All nuclear magnetic resonance spectra were recorded using a Varian Mercury Plus 400 MHz spectrometer equipped with a PFG ATB Broadband probe.

The 10 minute methods were run using a Waters 2795 separation module equipped with a Waters Micromass ZQ (ES ionisation) and Waters PDA 2996, using a Waters XTerra MS $C_{18}$ 3.5 µm 2.1×5 0 mm column.

Preparative HLPC was run using a Waters 2767 system with a binary Gradient Module Waters 2525 pump and coupled to a Waters Micromass ZQ (ES) or Waters 2487 DAD, using a Supelco Discovery HS C18 5.0 m 10×21.2 mm column.

Gradients were run using either method a: 0.1% formic acid/water and 0.1% formic acid/acetonitrile with gradient 5/95 to 95/5 in the run time indicated (flux: 1 mL/min), or method b: 0.1% formic acid/water and 0.1% formic acid/methanol with gradient 5/95 to 80/20 in the run time indicated (flux: 0.8 mL/min). Run time for final compounds is 10 min.

Purifications were performed with a silica gel cartridges isolute flash Si.

All TLC analyses were performed on silica gel (Merck 60 F254) and spots revealed by UV visualisation at 254 nm and $KMnO_4$ or ninhydrin stain.

GENERAL METHOD 1

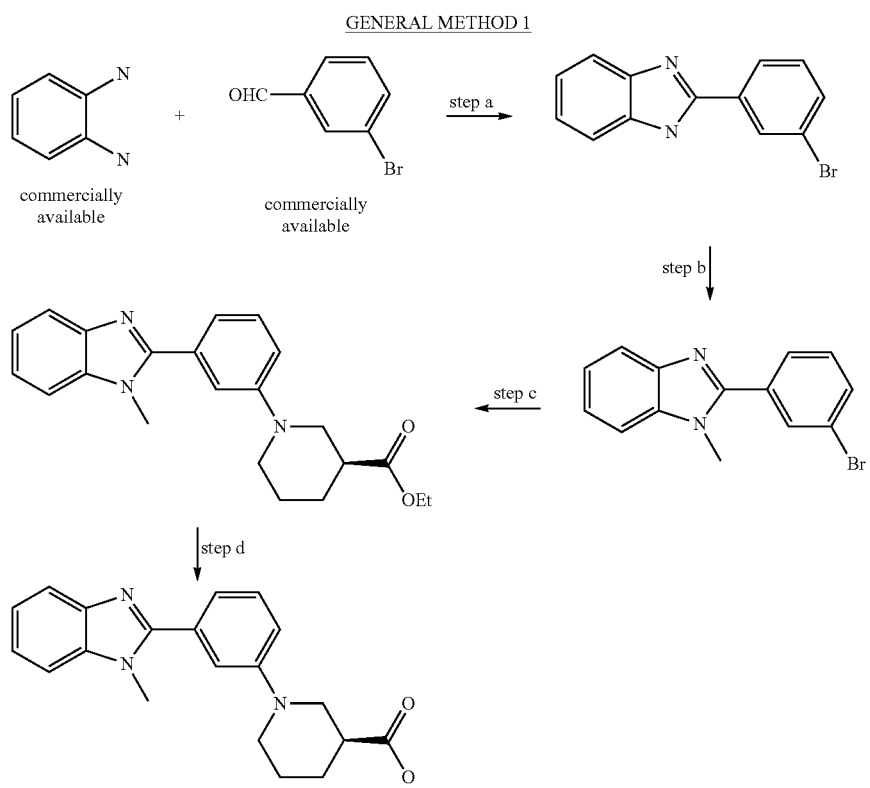

2-(3-bromophenyl)-1H-benzoimidazole

Method 1—Step a O-phenylenediamine (81.8 g, 756.6 mmol) and oxalic acid (3.40 g, 37.8 mmol) were completely dissolved in EtOH—H$_2$O/1:1 (2 L) previously warmed at 80° C. 3-Bromobenzaldehyde (44.10 mL, 378.30 mmol) was then added dropwise to the solution. The reaction mixture was stirred overnight at 70° C. to the open air. The day after solid was filtered off and triturated with MeOH (150 mL) to give the product as a pale yellow solid (27.50 g). 3.8 g were recovered from the mother liquors. Total yield 31.30 g (30%).

$^1$H-NMR (400 MHz DMSO): δ 7.24 (2H, m), 7.54 (2H, m), 7.70 (m, 2H), 8.19 (1H, m), 8.37 (1H, t), 13.2 (1H, s); m/z 273 (M+H)$^+$; retention time (method a)=8.60 (10 min run)

2-(3-Bromo-phenyl)-1-methyl-1H-benzoimidazole

Method 1—Step b—2-(3-bromophenyl)-1H-benzoimidazole (7.8 g, 28.6 mmol) was completely dissolved in dry THF (300 ml), then NaH 60% m/m (1.49 g, 37.2 mmol) was added portionwise to the clear yellow solution. The light brown suspension was stirred 1 h rt, then CH$_3$I (2.5 ml, 40.0 mmol) was added dropwise. The reaction mixture was stirred rt overnight. The reaction was quenched with H$_2$O (300 ml), and extracted with EtOAc (2×450 ml). The organic extracts were dried over MgSO$_4$, filtered and evaporated, to afford the compound as a brown-yellow solid (7.40 g, 70%).

$^1$H-NMR (400 MHz DMSO): δ 3.90 (3H, s), 7.30 (2H, m), 7.55 (1H, t), 7.64 (1H, d), 7.70 (1H, d), 7.77 (1H, m), 7.88 (1H, m), 8.05 (1H, m); m/z=287 [M+H]$^+$, retention time (method a)=7.70 (10 min run)

(S)-1-[3-(1-Methyl-1H-benzoimidazol-2-yl)-phenyl]-piperidine-3-carboxylic acid ethyl ester Method 1—Step c 2-(3-Bromo-phenyl)-1-methyl-1H-benzoimidazole (0.85 g, 2.96 mmol), (S)-(+)-Nipecotic acid ethyl ester (0.60 g, 3.85 mmol) and cesium carbonate (4.82 g, 14.80 mmol) were placed into a dry Schlenk tube under nitrogen. At the same time palladium acetate (0.14 g, 0.60 mmol), and rac-2,2'bis(diphenylphosphino)-1,1'-binaphtyl (BINAP) (0.57 g, 0.90 mmol) were placed into a dry 7 mL vial under nitrogen. Then dry toluene (5 mL) was added and the mixture was stirred 20 minutes under nitrogen before being added to the first flask. The reaction mixture was heated at 80° C. overnight, cooled to room temperature, filtered off, and the insoluble material was washed with EtOAC (3×10 mL). The organic solution was concentrated under reduced pressure and crude was purified by flash chromatography (eluent: cyclohexane:AcOEt gradient from 100% of cyclohexane to cyclohexane 4:AcOEt 1) to afford 0.75 g of the title compound (70%).

$^1$H-NMR (400 MHz, CD3OD): δ 1.25 (3H, t), 1.66-1.88 (3H, m), 1.95-2.03 (1H, m), 2.67-2.74 (1H, m), 2.94-3.01 (1H, m), 3.16-3.22 (1H, m), 3.52-3.57 (1H, m), 3.73-3.77 (1H, m), 4.15 (2H, q), 7.16-7.19 (2H, m), 7.28-7.36 (3H, m), 7.41-7.45 (1H, m), 7.53-7.56 (1H, m), 7.66-7.68 (1H, m).

S-1-[3-(1-Methyl-1H-benzoimidazol-2-yl)-phenyl]-piperidine-3-carboxylic acid hydrochloride Method 1—Step d A mixture of (S)-1-[3-(1-Methyl-1H-benzoimidazol-2-yl)-phenyl]-piperidine-3-carboxylic acid ethyl ester (0.76 g, 2.09 mmol) in 6N HCl (4.0 mL) was heated in microwave at 120° C. for 20 minutes; 3 cycles were needed to complete conversion. Then solvent was removed and the crude triturated with a mixture of acetone/ethyl acetate (1:1), the solid filtered off and dried under vacuum, to obtain 0.60 g of the title compound (86%).

$^1$H-NMR (400 MHz, DMSO): 1.52-1.84 (3H, m), 2.0 (1H, m), 2.65 (1H, m), 3.02 (1H, t), 3.16 (1H, t), 3.64 (1H, d), 3.80

(1H, d), 4.03 (3H, s), 7.35-7.51 (2H, m) 7.51-7.72 (4H, m), 7.83-7.90 (1H, m), 8.01-8.09 (1H, m); m/z 335 (M+H)+, retention time (method a)=1.27 (5 min run)

placed into a dry Schlenk tube under nitrogen. At the same time palladium acetate (0.17 g, 0.74 mmol), and BINAP (0.71 g, 1.11 mmol) were placed into a dry 7 mL vial under nitro-

GENERAL METHOD 2

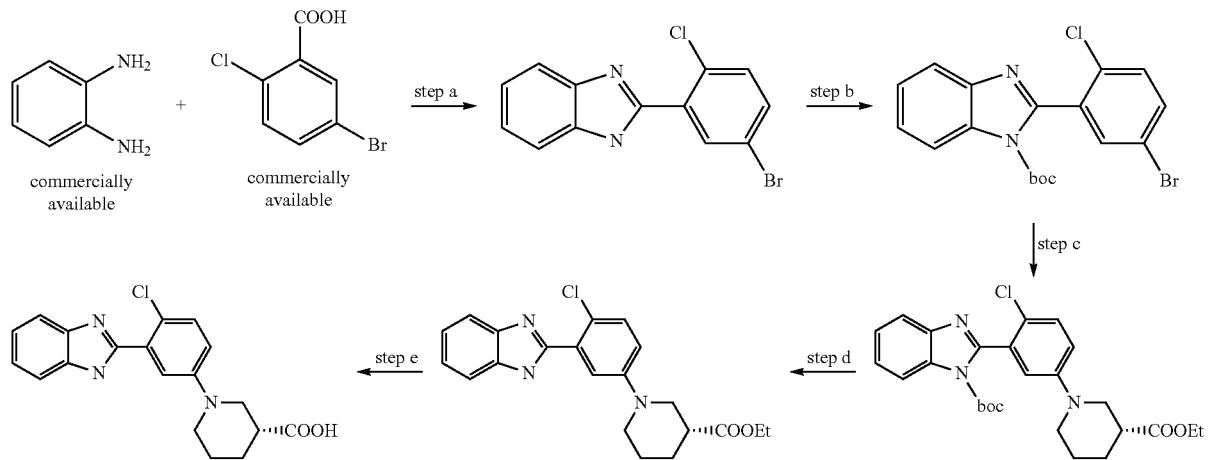

2-(5-bromo-2-chlorophenyl)-1H-benzoimidazole

Method 2—Step a Into a one necked round bottomed flask equipped with a magnetic stirrer, 5-bromo-2-chlorobenzoic acid (70.0 g, 297.3 mmol), o-phenylenediamine (64.3 g, 594.6 mmol) and methansulfonic acid (140 mL) were placed and heated to 170° C. in order to melt the solids. The system was stirred 5 h at this temperature, then left to come rt. The blue solid was treated with NaOH 35% (200 mL) obtaining a violet suspension (pH 5) that was filtered and washed with NaOH 0.5 M (2 L) and H$_2$O (2 L). The product was dried under vacuum (60° C.), to give 61.6 g of a pure violet solid. (67%).

m/z 307/309 (M+H)+; retention time (method a)=8.73 (10 min run)

2-(5-bromo-2-chloro-phenyl)-benzoimidazole-1-carboxylic acid tert-butyl ester Method 2—Step b—Into a three necked round bottomed flask equipped with a magnetic stirrer, 2-(5-bromo-2-chlorophenyl)-1H-benzimidazole (30.7 g, 99.8 mmol) was suspended in THF(1 L). 50% NaOH (72.0 g, 598 mmol) was then added. The suspension was left at r.t. for 1 h under stirring. (BOC)$_2$O (37.0 g, 169.7 mmol) was dissolved in THF (200 mL) and added to the reaction mixture. The reaction was left under stirring overnight. The solvent was evaporated under reduced pressure. The obtained residue was diluted with water (500 mL) filtered and dried under vacuum (60° C.), to give 39.8 g of a brown solid. (98%).

m/z 407/409 (M+H)+; retention time (method a)=9.14 (10 min run)

2-[2-Chloro-5-((R)-3-ethoxycarbonyl-piperidin-1-yl)-phenyl]-benzoimidazole-1-carboxylic acid tert-butyl ester Method 2—Step c 2-(5-bromo-2-chloro-phenyl)-benzoimidazole-1-carboxylic acid tert-butyl ester (1.50 g, 3.69 mmol), (R)-(−)-Nipecotic acid ethyl ester (0.75 g, 4.79 mmol) and cesium carbonate (6.00 g, 18.43 mmol) were gen. Then dry toluene (5 mL) was added and the mixture was stirred 20 minutes under nitrogen before being added to the first flask. The reaction mixture was heated at 80° C. overnight, cooled to room temperature, filtered off, and the insoluble material was washed with EtOAC (3×10 mL). The organic solution was concentrated under reduced pressure and crude was purified by flash chromatography (eluent: cyclohexane:AcOEt gradient from 100% of cyclohexane to cyclohexane 4: AcOEt 1) to afford 1.33 g of the title compound (74%).

$^1$H-NMR (400 MHz, CD3OD): δ 1.23 (3H, t), 1.36 (9H, s), 1.64-1.84 (3H, m), 1.84-2.00 (1H, m), 2.65-2.71 (1H, m), 2.93-2.98 (1H, m), 3.14-3.19 (1H, m), 3.45-3.51 (1H, m), 3.67-3.71 (1H, m), 4.14 (2H, q), 7.11-7.16 (2H, m), 7.35-7.37 (1H, m), 7.40-7.48 (2H, m), 7.71-7.73 (1H, m), 8.13-8.15 (1H, m).

(R)-1-[3-(1H-Benzoimidazol-2-yl)-4-chloro-phenyl]-piperidine-3-carboxylic acid ethyl ester Method 2—Step d To a mixture of 2-[2-Chloro-5-((R)-3-ethoxycarbonyl-piperidin-1-yl)-phenyl]-benzoimidazole-1-carboxylic acid tert-butyl ester (1.30 g, 2.68 mmol) in dichloromethane (2 mL), 2M HCl in Et$_2$O (10 mL) was added and the resulting mixture was stirred overnight at room temperature. The solid was filtered off, then recovered with 10% NaOH (10 mL) and extracted with dichloromethane (3×10 mL). The organic layer was dried over Na$_2$SO$_4$, filtered and concentrated under reduced pressure, to get 0.81 g of the title compound without further purifications (85%).

$^1$H-NMR (400 MHz, CD3OD): δ 1.25 (3H, t), 1.67-1.87 (3H, m), 1.98-2.03 (1H, m), 2.66-2.72 (1H, m), 2.94-3.01 (1H, m), 3.17-3.22 (1H, m), 3.50-3.55 (1H, m), 3.70-3.75 (1H, m), 4.14 (2H, q), 7.10-7.13 (1H, m), 7.26-7.31 (2H, m), 7.40-7.42 (2H, m), 7.62 (2H, bs); m/z=384 [M+H]+, retention time (method a)=1.82 (5 min run)

(R)-1-[3-(1H-Benzoimidazol-2-yl)-4-chloro-phenyl]-piperidine-3-carboxylic acid hydrochloride Method 2—Step e A mixture of (R)-1-[3-(1H-Benzoimidazol-2-yl)-4-chloro-phenyl]-piperidine-3-carboxylic acid ethyl ester (0.81 g, 2.11 mmol) in 6N HCl (4.0 mL) was heated in microwave at 120° C. for 20 minutes; 2 cycles were needed to complete conversion. Then solvent was removed and the crude triturated with a mixture of acetone/ethyl acetate (1:1), the solid filtered off and dried under vacuum, to obtain 0.60 g of the title compound (80%).

$^1$H-NMR (400 MHz, DMSO): δ 1.50-1.725 (2H, m), 1.72 (1H, m), 2.54 (1H, m), 2.93 (1H, t), 3.06 (1H, t), 3.63 (1H, d), 3.80 (1H, dd), 7.31 (1H, dd), 7.54-7.58 (2H, m), 7.60-7.62 (2H, m), 7.86-7.90 (2H, m); m/z 355 (M+H)$^+$, retention time (method a)=1.45 (5 min run)

2-(5-Bromo-2-chloro-phenyl)-5-fluoro-1H-benzoimidazole

Method 3,4—Step b A solution of N-(2-Amino-5-fluoro-phenyl)-5-bromo-2-chloro-benzamide (6.90 g, 20.12 mmol) in acetic acid (40 mL) was stirred at 80° C. overnight, solvent was then removed under reduced pressure and the crude purified by precipitation from diethylether to obtain 6.00 g of the title compound (92%).

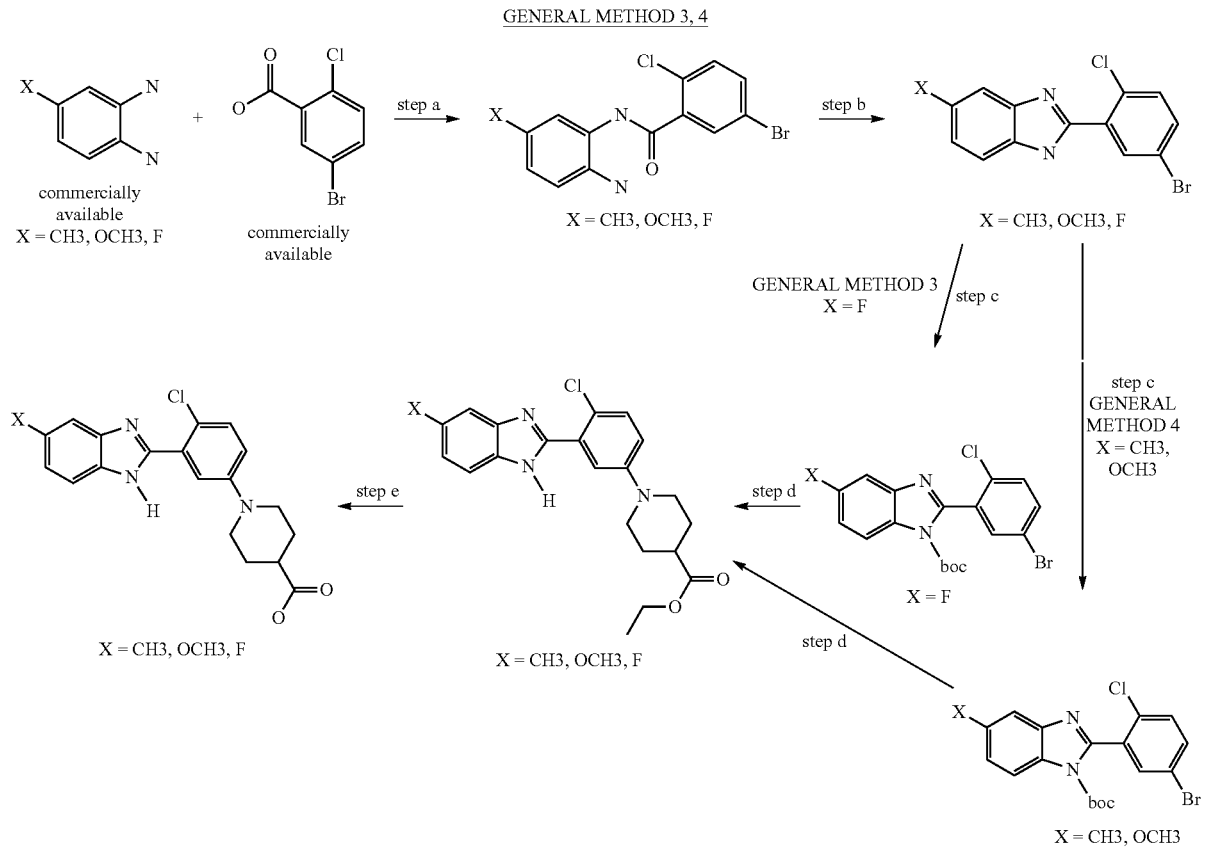

GENERAL METHOD 3, 4

N-(2-Amino-5-fluoro-phenyl)-5-bromo-2-chloro-benzamide

Method 3,4—Step a To a mixture of the solids 5-Bromo-2-chlorobenzoic acid (7.00 g, 29.79 mmol), 4-Fluoro-benzene-1,2-diamine (4.65 g, 36.94 mmol) and O-(7-Azabenzotriazol-1-yl)-N,N,N',N'-tetramethyluronium hexafluorophosphate (HATU) (11.89 g, 31.28 mmol), triethylamine (TEA) (4.60 mL, 32.77 mmol), dichloromethane (120 mL) and dimethylformamide (DMF) (30 mL) were added. The reaction mixture was stirred at room temperature overnight, water was added (30 mL) and stirred until the formation of a precipitate. The precipitate was filtered off, washed with dichloromethane (3×10 mL) and dried to afford 6.90 g of the title compound (69%).

$^1$H-NMR (400 MHz, DMSO-d$_6$): δ 5.27 (2H, s), 6.34 (1H, td), 6.50 (1H, dd), 7.17 (1H, dd), 7.50 (1H, d), 7.67 (1H, dd), 7.97 (1H, d), 9.72 (1H, s); m/z 345 (M+2)$^+$ $^1$H-NMR (400 MHz, DMSO-d$_6$): δ 7.10 (1H, m), 7.35-7.50 (1H, 7.56 and 7.70 (1H, m), 7.61 (1H, m), 7.73 (1H, m), 8.08 (1H, m), 12.92 (1H, s). m/z 327 (M+2)$^+$

2-(5-Bromo-2-chloro-phenyl)-5-fluoro-benzoimidazole-1-carboxylic acid tert-butyl ester Method 3—Step c To a flask with 2-(5-Bromo-2-chloro-phenyl)-5-fluoro-1H-benzoimidazole (6.00 g, 18.46 mmol), 4-dimethylaminopyridine (DMAP) (0.23 g, 1.85 mmol), di-tert-butyl dicarbonate (Boc$_2$O) (5.23 g, 24.00 mmol) and dichloromethane (90 mL) were added. The reaction mixture was stirred at room temperature overnight, solvent was removed under reduced pressure and the crude precipitated from a mixture of cyclohexane:AcOEt/10:1 to get 4.60 g of the title compound (59%).

$^1$H-NMR (400 MHz, CDCl$_3$): δ 1.40 (9H, s), 7.10-7.22 (1H, m), 7.34 (1H, dd), 7.47 and 7.83 (1H, m), 7.55-7.59 (1H, m), 7.71 (1H, m), 7.74 and 8.06 (1H, m); m/z 427 (M+2)$^+$

2-(5-Bromo-2-chloro-phenyl)-5-methoxy-benzoimidazole-1-carboxylic acid tert-butyl ester Method 4—Step c To a flask with 2-(5-Bromo-2-chloro-phenyl)-5-methoxy-1H-benzoimidazole (6.50 g, 19.29 mmol), DMAP (0.23 g, 1.93 mmol), Boc$_2$O (5.47 g, 25.07 mmol) and dichloromethane (100 mL) were added. The reaction mixture was stirred at room temperature overnight and solvent was removed under reduced pressure. The crude was purified by flash chromatography (eluent gradient: from cyclohexane:AcOEt/5:1 to 1:2), get 4.70 g of the title compound (56%).

$^1$H-NMR (400 MHz, DMSO): δ 1.32 (9H, s), 3.82 (3H, d), 7.04 (1H, m), 7.29 and 7.65 (1H, m), 7.56 (2H, m), 7.75 (1H, m), 7.88 (1H, m); m/z 438 (M+H)$^+$, retention time (method 7.47 (10 min run).

2-[2-Chloro-5-(4-ethoxycarbonyl-piperidin-1-yl)-phenyl]-5-fluoro benzoimidazole-1-carboxylic acid tert-butyl ester Method 3,4—Step d 2-(5-Bromo-2-chloro-phenyl)-5-fluoro-benzoimidazole-1-carboxylic acid tert-butyl ester (1.04 g, 2.46 mmol), piperidine-4-carboxylic acid ethyl ester (0.49 mL, 3.19 mmol) and cesium carbonate (3.99 g, 12.29 mmol) were placed into a dry Schlenk tube under nitrogen. At the same time palladium acetate (0.11 g, 0.49 mmol), and BINAP (0.46 g, 0.74 mmol) were placed into a dry 7 mL vial under nitrogen. Then dry toluene (4 mL) was added and the mixture was stirred 20 minutes under nitrogen before being added to the first flask. The reaction mixture was heated at 80° C. overnight, cooled to room temperature, salts were filtered off, the organic solution was concentrated under reduced pressure and crude was purified by flash chromatography (eluent: cyclohexane:AcOEt gradient from cyclohexane:AcOEt/5:1 to 1:2) to afford 0.84 g of the title compound (68%).

$^1$H-NMR (400 MHz, CD$_3$OD): δ 1.35 (3H, t), 1.45 (9H, s), 1.80 (2H, m), 1.99 (2H, m), 2.52 (1H, m), 2.88 (2H, m), 3.72 (2H, m), 4.13 (2H, q), 7.10-7.28 (3H, m), 7.35 (1H, d), 7.43 and 7.86 (1H, m), 7.71 and 8.14 (1H, dd); m/z 502 (M+H)$^+$, retention time (method 3.10 (5 min run)

1-[4-Chloro-3-(5-fluoro-1H-benzoimidazol-2-yl)-phenyl]-piperidine-4-carboxylic acid hydrochloride Method 3,4—Step e A mixture of 2-[2-Chloro-5-(4-ethoxycarbonyl-piperidin-1-yl)-phenyl]-5-fluoro-benzoimidazole-1-carboxylic acid tert-butyl ester (0.42 g, 0.84 mmol) in 6N HCl (4 mL) was stirred at room temperature for few minutes and then heated in microwave at 120° C. for 15 minutes. Solvent was removed under vacuum to obtain the title compound in quantitative yield.

$^1$H-NMR (400 MHz, CD$_3$OD): δ 1.95 (2H, m), 2.13 (2H, m), 2.65 (1H, m), 3.20 (2H, m), 3.83 (2H, m), 7.53 (2H, m), 7.69 (3H, m), 7.91 (1H, m); m/z 374 (M+H)$^+$, retention time (method a)=1.65 (5 min run).

GENERAL METHOD 5

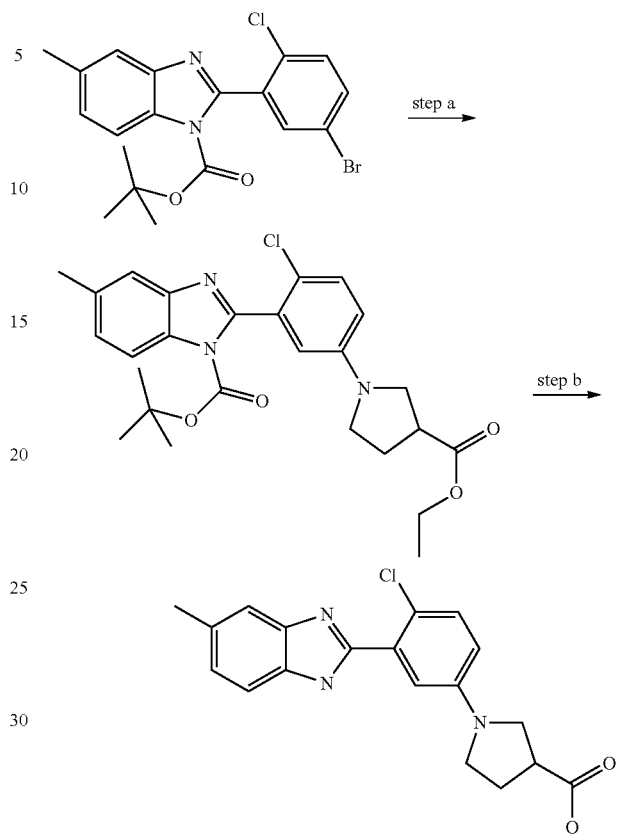

2-[2-Chloro-5-(3-ethoxycarbonyl-pyrrolidin-1-yl)-phenyl]-5-methyl-benzoimidazole-1-carboxylic acid tert-butyl ester Method 5—Step a 2-(5-Bromo-2-chloro-phenyl)-5-methyl-benzoimidazole-1-carboxylic acid tert-butyl ester (obtained as described in general method 4, step c) (1.80 g, 4.28 mmol), pyrrolidine-3-carboxylic acid methyl ester (0.92 g, 5.56 mmol) and cesium carbonate (6.95 g, 21.38 mmol) were to a dry flask under nitrogen containing palladium acetate (0.19 g, 0.86 mmol) and BINAP (0.80 g, 1.28 mmol) in dry toluene (11 mL) and previously stirred for 20 minutes under nitrogen. The reaction mixture was heated at 80° C. overnight, cooled to room temperature, diluted with AcOEt (40 mL), salts were filtered off, the organic layer washed with water (1×30 mL) and brine (1×20 mL), dried over Na$_2$SO$_4$ and then concentrated under reduced pressure. To the crude a mixture of solvents cyclohexane:AcOEt/4:1 (15 mL) was added and filtered through a column with Na$_2$SO$_4$ to remove all the salts, washed with the mixture of solvents and the organic layer purified by flash chromatography (eluent: cyclohexane:AcOEt/4:1) to afford 1.71 g of the title compound (86%).

$^1$H-NMR (400 MHz, DMSO-d$_6$): δ 1.30 (9H, s), 1.38 (3H, s), 2.20 (2H, m), 3.24-3.51 (5H, m), 3.63 (3H, s), 6.68 (1H, m), 6.74 (1H, m), 7.23 (1H, m), 7.30 (1H, m), 7.54 and 7.82 (1H, m), 7.62 and 7.86 (1H, m); m/z 470 (M+H)$^+$, retention time (method a)=5.12 (10 min run)

1-[4-Chloro-3-(5-methyl-1H-benzoimidazol-2-yl)-phenyl]-pyrrolidine-3-carboxylic acid Method 5—Step b As described in general method 3,4 step e, starting from 2-[2-Chloro-5-(3-ethoxycarbonyl-pyrrolidin-1-yl)-phenyl]-5-methyl-benzoimidazole-1-carboxylic acid tert-butyl ester to get the title compound in quantitative yield.

and washed with saturated NaHCO$_3$ solution (3×5 mL), the organic layer recovered by filtration through phase separator, and the solvent removed under reduced pressure to obtain 0.86 g of the title compound (63%).

$^1$H-NMR (400 MHz, DMSO-d$^6$): δ 3.79 (3H, s), 6.86 (1H, d), 7.04 (1H, bs), 7.41 (1H, dd), 7.55 (1H, bs), 7.69 (1H, m), 8.30 (1H, m), 11.93 (1H, s).

GENERAL METHOD 6

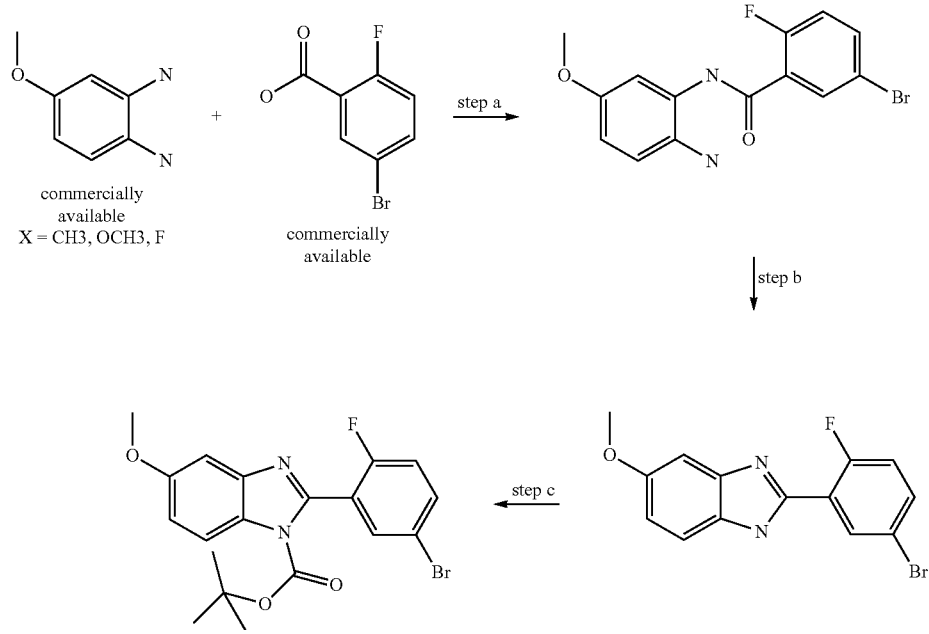

commercially available
X = CH3, OCH3, F commercially available

N-(2-Amino-5-methoxy-phenyl)-5-bromo-2-fluoro-benzamide 2-(5-Bromo-2-fluoro-phenyl)-5-methoxy-benzoimidazole-1-carboxylic acid tert-butyl ester Method 6—Step a A mixture of 5-Bromo-2-fluoro-benzoic acid (1.50 g, 6.85 mmol), 4-methoxy-benzene-1,2-diamine dihydrochloride (1.77 g, 8.49 mmol), HATU (2.73 g, 7.19 mmol) and TEA (2.88 mL, 20.76 mmol) in dichloromethane (20 mL) and DMF (5 mL) was stirred at room temperature overnight, then water was added (50 mL), mixture was stirred for 2 h and left standing at room temperature overnight. The precipitate obtained was filtered off and dried to afford 1.45 g of the title compound (50%).

$^1$H-NMR (400 MHz, DMSO-d$^6$): δ 3.65 (3H, s), 4.96 (2H, bs), 6.15 (1H, dd), 6.31 (1H, s), 7.05 (1H, d), 7.31 (1H, m), 7.71 (1H, m), 7.91 (1H, d), 9.50 (1H, s).

2-(5-Bromo-2-fluoro-phenyl)-5-methoxy-1H-benzoimidazole

Method 6—Step b A mixture of N-(2-Amino-5-methoxy-phenyl)-5-bromo-2-fluoro-benzamide (1.45 g, 4.28 mmol) in acetic acid (15 mL) was heated at 80° C. overnight. Solvent was removed under reduced pressure and the crude purified by precipitation from AcOEt (20 mL), dried, recovered with a mixture of dichloromethane (20 mL) and methanol (1 mL)

Method 6—Step c To a stirred mixture of 2-(5-Bromo-2-fluoro-phenyl)-5-methoxy-1H-benzoimidazole (0.87 g, 2.70 mmol) in dcm (10 mL), Boc$_2$O (0.76 g, 3.50 mmol) and DMAP (0.03 g, 0.27 mmol) were added and the reaction mixture was left stirring at room temperature for a week end. Then dichloromethane (20 mL) was added and the reaction mixture was washed with saturated NaHCO$_3$ solution (4 mL), citric acid (10% solution), the organic layer recovered by filtration through phase separator, and the solvent removed under reduced pressure. The crude was then purified by flash chromatography (eluent cyclohexane:ethyl acetate/10:1) to obtain 0.82 g of the title compound as mixture of two diastereoisomers (72%).

$^1$H-NMR (400 MHz, CDCl$_3$): δ 1.45 (9H, s), 1.47 (9H, s), 3.88 (3H, s), 3.90 (3H, s), 6.98-7.06 (4H, m), 7.25-7.27 and 7.80-7.83 (3H, m), 7.54-7.61 (3H, m), 7.93 (1H, m); m/z 423 (M+2H)$^+$, retention time (method a)=3.02 (5 min run).

GENERAL METHOD 7

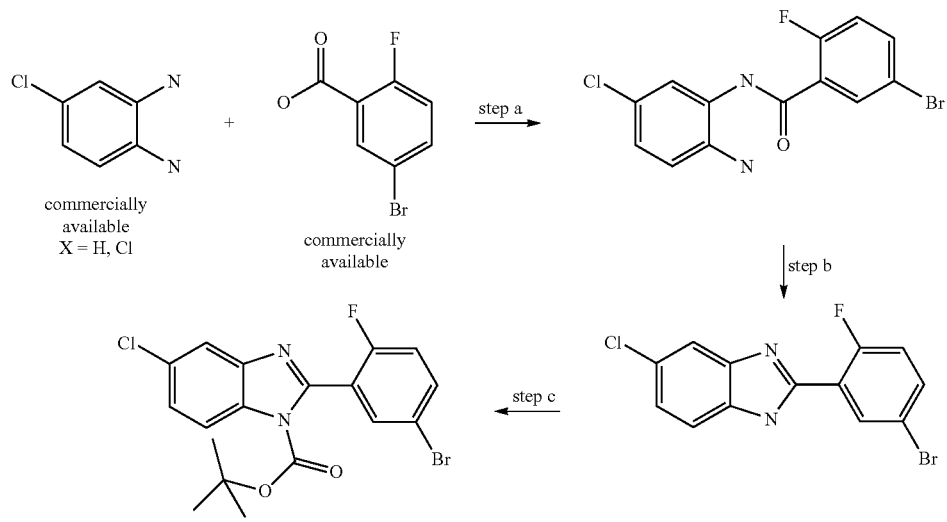

N-(2-Amino-5-chloro-phenyl)-5-bromo-2-fluoro-benzamide

Method 7—Step a A mixture of 5-Bromo-2-fluoro-benzoic acid (3.00 g, 13.70 mmol), 4-chloro-benzene-1,2-diamine (2.42 g, 16.99 mmol), HATU (5.47 g, 14.38 mmol) and TEA (1.91 mL, 13.83 mmol) in dichloromethane (70 mL) and DMF (16 mL) was stirred at room temperature overnight, then water was added (80 mL) and left standing at room temperature overnight. The organic layer was divided and solvent removed under reduced pressure and the crude oil obtained was crystallized from the mixture of solvents dichloromethane:cyclohexane/3:1 (30 mL) to afford 2.19 g of the title compound (52%).

m/z 344 (M+H)$^+$, retention time=5.33(10 min run)$^a$

2-(5-Bromo-2-fluoro-phenyl)-5-chloro-1H-benzoimidazole

Method 7—Step b A mixture of N-(2-Amino-5-chloro-phenyl)-5-bromo-2-fluoro-benzamide (1.60 g, 4.67 mmol) in acetic acid (10 mL) was heated at 85° C. overnight. Solvent was removed under reduced pressure and the solid obtained was washed with dichloromethane and dried to obtain 1.40 g of the title compound (93%).

$^1$H-NMR (400 MHz, CD3OD): δ 7.27-7.33 (2H, m), 7.60-7.64 (2H, m), 7.69 (1H, m), 8.33 (1H, dd).

2-(5-Bromo-2-fluoro-phenyl)-5-chloro-benzoimidazole-1-carboxylic acid tert-butyl ester Method 7—Step c To a stirred mixture of 2-(5-Bromo-2-fluoro-phenyl)-5-chloro-1H-benzoimidazole (1.41 g, 4.33 mmol) in dcm (28 mL), Boc$_2$O (1.23 g, 5.63 mmol) and DMAP (0.05 g, 0.43 mmol) were added and the reaction mixture was left stirring at room temperature overnight. The reaction mixture was washed with saturated NaH$_4$Cl solution (2×5 mL), and the crude was then purified by flash chromatography (eluent gradient: cyclohexane:EtOAc from 8:1 to 5:1), to obtain 1.31 g of the title compound (71%) as mixture of two regioisomers.

$^1$H-NMR (400 MHz, CDCl$_3$): δ 1.45 (9H, 2s), 7.05 (1H, m), 7.39 (1H, m), 7.60 (1H, m), 7.71 (0.5H, d), 7.78 (0.5H, d), 7.83 (1H, m), 7.99 (0.5H, d), 8.10 (0.5H, d).

GENERAL METHOD 8

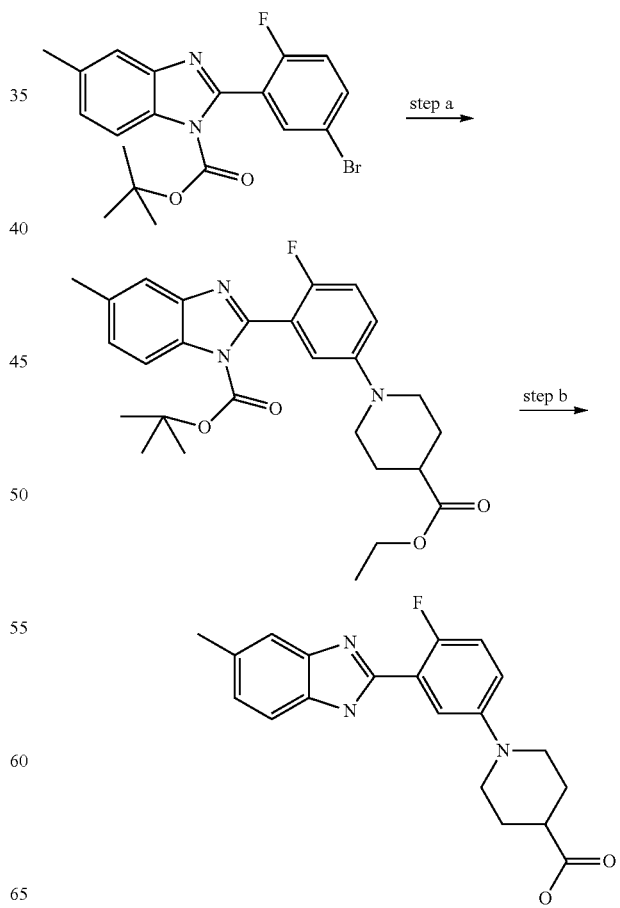

2-[5-(4-Ethoxycarbonyl-piperidin-1-yl)-2-fluoro-phenyl]-5-methyl-benzoimidazole-1-carboxylic acid tert-butyl ester Method 8—Step a 2-(5-Bromo-2-fluoro-phenyl)-5-methyl-benzoimidazole-1-carboxylic acid tert-butyl ester (obtained as described in general method 6, step c) (0.94 g, 2.40 mmol), piperidine-4-carboxylic acid ethyl ester (0.48 g, 3.12 mmol) and cesium carbonate (3.90 g, 12.01 mmol) were placed into a dried schlenk tube and 3 cycles of vacuum/nitrogen were performed, then dry toluene (4 mL) was added. At the same time palladium(II)acetate (0.82 g, 0.36 mmol), and BINAP (0.45 g, 0.72 mmol) were placed into a dried schlenk tube under nitrogen and 3 cycles of vacuum/nitrogen were performed. Then dry toluene (2 mL) was added, at room temperature under nitrogen, and the mixture was added to the first schlenk. The reaction mixture was heated at 80° C. overnight, water (5 mL) was added, the organic layer was filtered over $Na_2SO_4$ and then purified by flash chromatography (eluent: cyclohexane:EtOAc 8:2) to obtain 1.15 g of the title compound in quantitative yield.

$^1$H-NMR (400 MHz, $CDCl_3$): δ 1.27 (3H, t), 1.43 (9H, s), 1.89 (2H, m), 2.02 (2H, m), 2.41 (1H, m), 2.50 (3H, s), 2.80 (2H, m), 3.59 (2H, m), 4.16 (2H, q), 7.01 (2H, m), 7.21 (2H, m), 7.66 (1H, d), 7.91 (1H, d).

1-[4-(Fluoro-3-(5-methyl-1H-benzoimidazol-2-yl)-phenyl]-piperidine-4-carboxylic acid hydrochloride.

Method 8—Step b A mixture of 2-[5-(4-Ethoxycarbonyl-piperidin-1-yl)-2-fluoro-phenyl]-5-methyl-benzoimidazole-1-carboxylic acid tert-butyl ester (1.15 g, 2.39 mmol) in 6N HCl (10 mL) was heated in microwave at 120° C. for 15 minutes (2 runs were needed). Solvent was removed under vacuum to obtain the title compound in quantitative yield.

$^1$H-NMR (400 MHz, DMSO-$d_6$): δ 2.19 (2H, m), 2.34 (2H, m), 2.59 (3H, s), 2.80 (1H, m), 3.55 (2H, m), 3.85 (2H, m), 7.53 (1H, d), 7.63-7.70 (2H, m), 7.78 (1H, d), 7.91-7.96 (1H, m), 8.27-8.33 (1H, m).

GENERAL METHOD 9

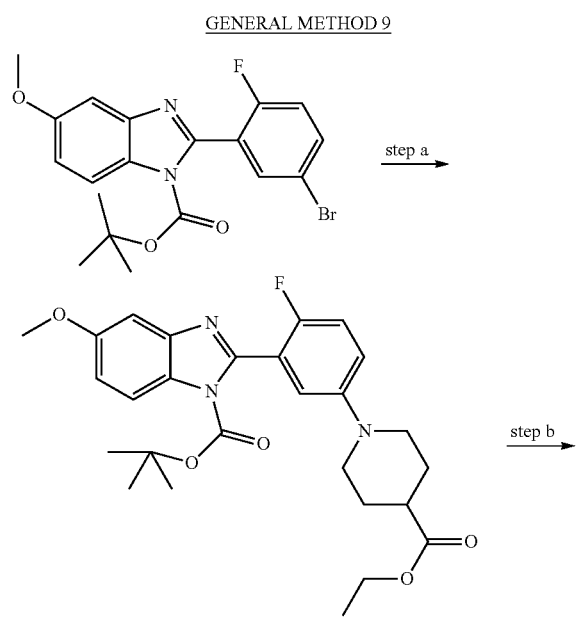

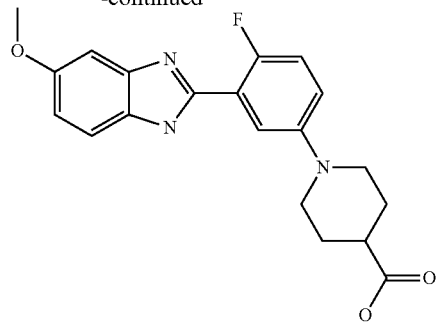

2-[5-(4-Ethoxycarbonyl-piperidin-1-yl)-2-fluoro-phenyl]-5-methoxy-benzoimidazole-1-carboxylic acid tert-butyl ester Method 9—Step a 2-(5-Bromo-2-fluoro-phenyl)-5-methoxy-benzoimidazole-1-carboxylic acid tert-butyl ester (obtained as described in general method 6, step c) (1.05 g, 2.50 mmol), piperidine-4-carboxylic acid ethyl ester (0.51 g, 3.25 mmol) and cesium carbonate (4.07 g, 12.50 mmol) were placed into a dried schlenk tube and 3 cycles of vacuum/nitrogen were performed, then dry toluene (4 mL) was added. At the same time palladium(II)acetate (0.11 g, 0.50 mmol), and BINAP (0.48 g, 0.75 mmol) were placed into a dried schlenk tube under nitrogen and 3 cycles of vacuum/nitrogen were performed. Then dry toluene (2 mL) was added, at room temperature under nitrogen, and the mixture was added to the first schlenk. The reaction mixture was heated at 80° C. overnight, cooled to room temperature, EtOAC (20 mL) was added and the mixture filtered off. Solvent was removed and the crude was purified by flash chromatography (eluent gradient: cyclohexane:EtOAc from 4:1 to 3:1), to obtain 0.82 g of the title compound (69%).

$^1$H-NMR (400 MHz, $CD_3OD$, two regioisomers): δ 1.25 (6H, t), 1.40 (18H, s), 1.76-1.88 (4H, m), 1.96-2.04 (4H, m), 2.42-2.51 (2H, m), 2.80 (4H, t), 3.58-3.65 (4H, m); 3.85 (3H, s); 3.87 (3H, s); 4.13 (4H, q); 6.99-7.06 (2H, m), 7.07-7.18 (4H, m), 7.19-7.23 (3H, m), 7.58 (1H, d), 7.62 (1H, d); 7.94 (1H, d); m/z 498 (M+H)$^+$ 1-[4-(Fluoro-3-(5-methoxy-1H-benzoimidazol-2-yl)-phenyl]-piperidine-4-carboxylic acid hydrochloride Method 9—Step b A mixture of 2-[5-(4-Ethoxycarbonyl-piperidin-1-yl)-2-fluoro-phenyl]-5-methoxy-benzoimidazole-1-carboxylic acid tert-butyl ester (0.92 g, 1.91 mmol) in 6N HCl (4 mL) was stirred at room temperature for 1 h and then heated in microwave at 120° C. for 15 minutes. Solvent was removed under vacuum, then taken with a mixture of acetone:diethyl ether 1:1 (20 mL), the solid was filtered, washed with diethyl ether and dried to obtain 0.22 g of the title compound (29%).

$^1$H-NMR (400 MHz, $CD_3OD$,): δ 1.98-2.10 (2H, m), 2.18-2.26 (2H, m), 2.63-2.71 (1H, m), 3.24-3.32 (2H, m), 3.77-3.84 (2H, m); 3.95 (3H, s); 7.26-7.31 (2H, m), 7.54 (1H, dd), 7.65-7.71 (1H, m), 7.75 (1H, dd), 7.92-7.98 (1H, m); m/z 370 (M+H)$^+$

GENERAL METHOD 10

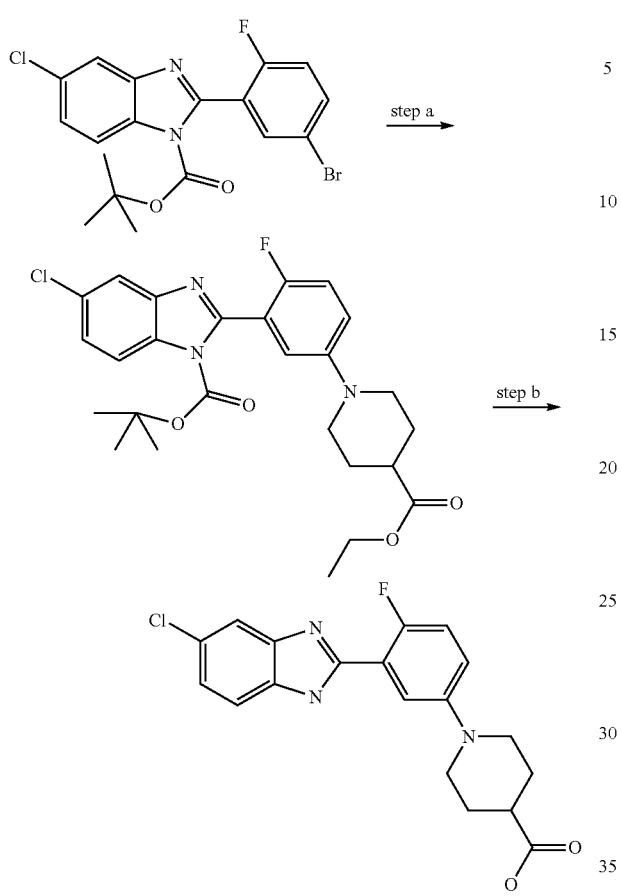

5-Chloro-2-[5-(4-ethoxycarbonyl-piperidin-1-yl)-2-fluoro-phenyl]-benzoimidazole-1-carboxylic acid tert-butyl ester Method 10—Step a 2-(5-Bromo-2-fluoro-phenyl)-5-chloro-benzoimidazole-1-carboxylic acid tert-butyl ester (obtained as described in general method 7, step c) (1.06 g, 2.50 mmol), Pd$_2$(dba)$_3$ (0.36 g, 0.50 mmol), 2-di-t-butylphosphino-2',4',6'-tri-1-propyl-1,1'biphenyl (t-BuXphos) (0.32 g, 0.75 mmol) and sodium tert-butoxide (0.48 g, 5.00 mmol) were placed into a dried vial and few cycles of vacuum/nitrogen were performed. Then dry toluene (5 mL) and piperidine-4-carboxylic acid ethyl ester (0.50 mL, 3.25 mmol) were added, the reaction mixture was heated at 85° C. overnight, and washed with saturated Na$_2$CO$_3$ solution (3×5 mL) and water (3×3 mL). The organic layer was dried over Na$_2$SO$_4$, filtered and concentrated under reduced pressure, and the crude was purified by flash chromatography (eluent: gradient from EtOAc:cyclohexane/1:5 to 1:2) to obtain 0.30 g of the title compound (24%).

$^1$H-NMR (400 MHz, CDCl$_3$): δ 1.26 (3H, t), 1.43 (9H, s), 1.60 (2H, m), 1.90 (2H, m), 2.42 (1H, m), 2.81 (2H, m), 3.60 (2H, m), 4.16 (2H, q), 7.05 (2H, m), 7.36 (2H, m), 7.69 (1H, d), 8.09 (1H, s).

1-[3-(5-Chloro-1H-benzoimidazol-2-yl)-4-fluoro-phenyl]piperidine-4-carboxylic acid hydrochloride Method 10—Step b A mixture of 5-Chloro-2-[5-(4-ethoxycarbonyl-piperidin-1-yl)-2-fluoro-phenyl]-benzoimidazole-1-carboxylic acid tert-butyl ester (0.30 g, 0.60 mmol) in 6N HCl (10 mL) was heated in microwave at 120° C. for 15 minutes, two cycles were needed. Solvent was removed under vacuum, then the solid was filtered and washed with diethyl ether and dried to obtain 0.17 g of the title compound (70%).

GENERAL METHOD 11

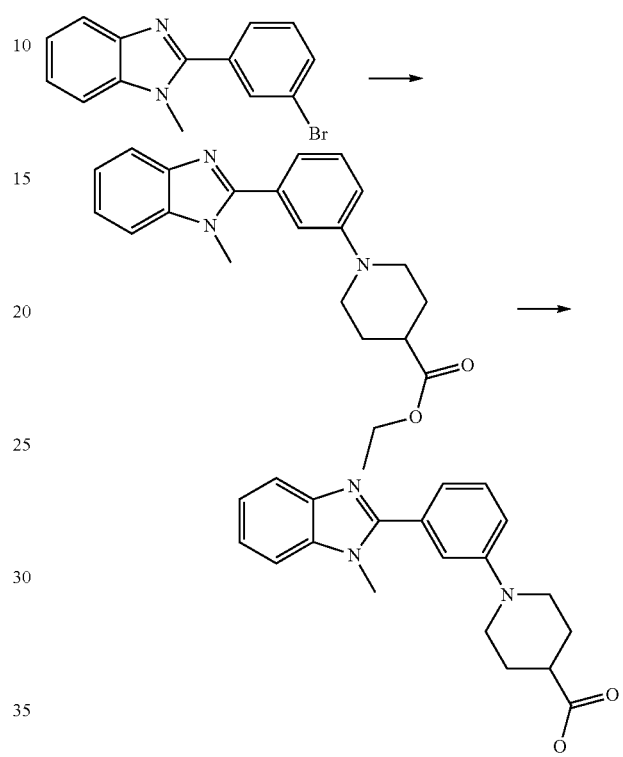

1-[3-(1-Methyl-1H-benzoimidazol-2-yl)-phenyl]-piperidine-4-carboxylic acid ethyl ester Method 11—Step a 2-(3-Bromo-phenyl)-1-methyl-1H-benzoimidazole (obtained as described in general method 1, step b) (5.00 g, 17.40 mmol), piperidine-4-carboxylic acid esthyl ester (3.56 g, 22.62 mmol) and cesium carbonate (28.34 g, 87 mmol) were placed into a round bottom flask under nitrogen. At the same time palladium acetate (0.79 g, 3.48 mmol), and BINAP (3.33 g, 5.22 mmol) were placed into a flask under nitrogen. Then dry toluene (18 mL) was added and the mixture was stirred 20 minutes under nitrogen before being added to the first flask. The reaction mixture was heated at 80° C. for two days, then diluted with ethyl acetate (100 mL), filtered through Na$_2$SO$_4$, and washed with water (2×50 mL) and brine (1×50 mL). The organic solution was concentrated under reduced pressure and crude was purified by flash chromatography (eluent: cyclohexane:AcOEt/4:1) to afford 3.45 g of the title compound (55%).

$^1$H-NMR (400 MHz, DMSO-d6): δ 1.19 (3H, t), 1.68 (2H, qd), 1.93 (2H, dd), 2.49-2.58 (1H, m), 2.86 (2H, td); 3.75 (2H, dt); 3.86 (3H, s); 4.09 (2H, q), 7.10-7.42 (6H, m), 7.59 (1H, d), 7.67 (1H, d).

1-[3-(1-Methyl-1H-benzoimidazol-2-yl)-phenyl]-piperidine-4-carboxylic acid hydrochloride Method 11—Step b A mixture of 1-[3-(1-Methyl-1H-benzoimidazol-2-yl)-phenyl]-piperidine-4-carboxylic acid ethyl ester (3.10 g, 8.54 mmol) in 6N HCl (25.0 mL) was heated in microwave at 120° C. for 20 minutes. Then solvent was removed to obtain the title compound in quantitative yield.

¹H-NMR (400 MHz, MeOD): δ 1.65-1.85 (2H, m), 1.94 (2H, d), 2.48-2.57 (1H, m), 3.04 (2H, t), 3.79 (2H, d), 4.05 (3H, s), 7.37-7.54 (2H, m), 7.55-7.71 (4H, m), 7.84-7.91 (1H, m), 8.03-8.09 (1H, m); m/z 333 (M+H)$^+$, retention time (method b)=1.95 (10 min run)

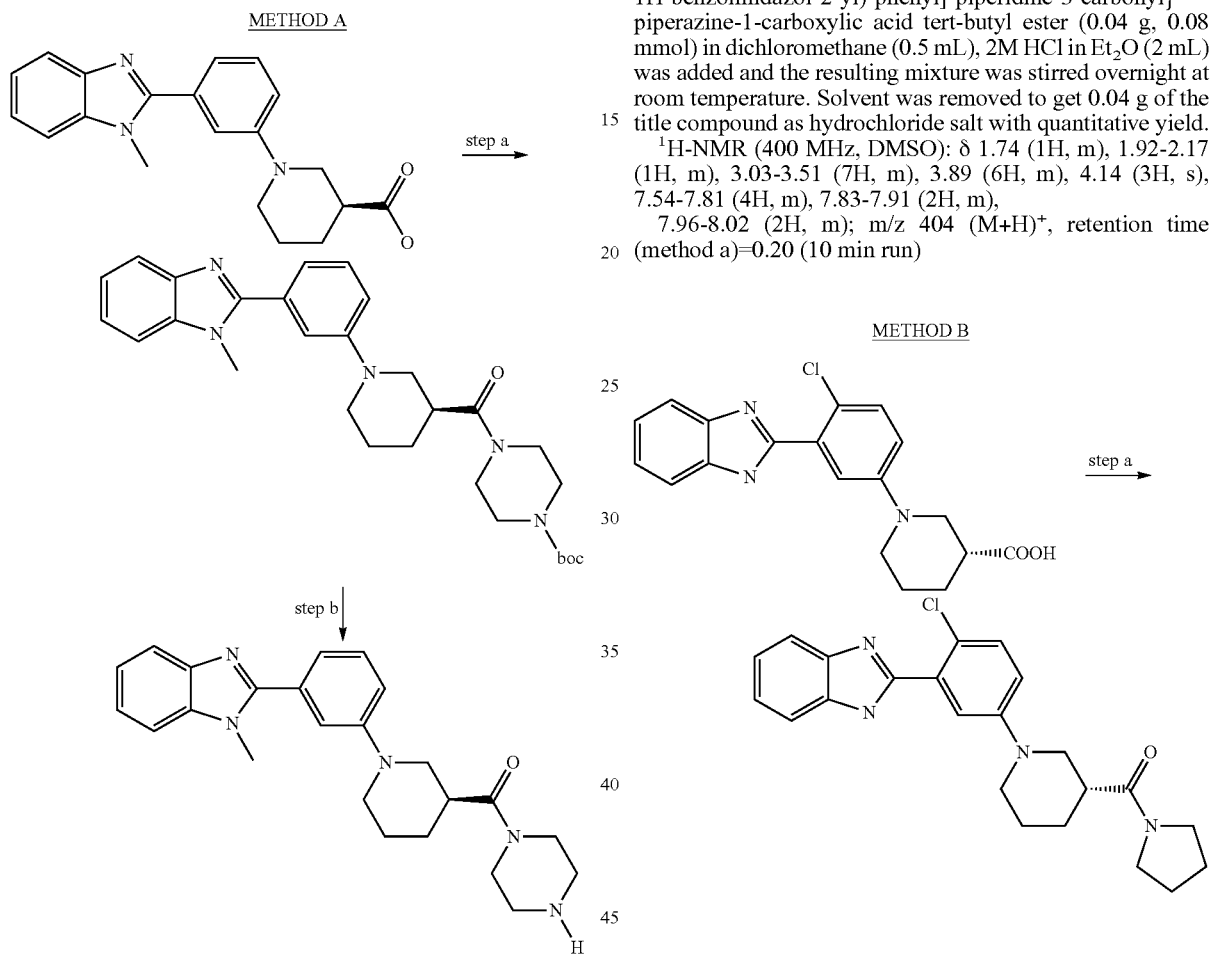

Example 1

{(S)-1-[3-(1-Methyl-1H-benzoimidazol-2-yl)-phenyl]-piperidin-3-yl}-piperazin-1-yl-methanone hydrochloride 4-{(S)-1-[3-(1-Methyl-1H-benzoimidazol-2-yl)-phenyl]-piperidine-3-carbonyl}-piperazine-1-carboxylic acid tert-butyl ester Method A—Step a To a vial with (S)-1-[3-(1-Methyl-1H-benzoimidazol-2-yl)-phenyl]-piperidine-3-carboxylic acid (0.10 g, 0.30 mmol) (obtained as described in general method 1, step d), HATU (0.12 g, 0.31 mmol), TEA (0.09 mL, 0.66 mmol) and tert-Butyl-1-piperazinecarboxylate (0.07 g, 0.37 mmol) dichloromethane (2 mL) was added and the reaction mixture was heated at 35° C. overnight. Reaction was cooled to room temperature, solvent removed and the crude purified by preparative HPLC and NH2 column filtration, to obtain 0.04 g of the title compound (27%).

m/z 503 (M+H)$^+$, retention time (method a)=2.52 (10 min run)

{(S)-1-[3-(1-Methyl-1H-benzoimidazol-2-yl)-phenyl]-piperidin-3-yl}-piperazin-1-yl-methanone hydrochloride Method A—Step b To a mixture of 4-{(S)-1-[3-(1-Methyl-1H-benzoimidazol-2-yl)-phenyl]-piperidine-3-carbonyl}-piperazine-1-carboxylic acid tert-butyl ester (0.04 g, 0.08 mmol) in dichloromethane (0.5 mL), 2M HCl in Et$_2$O (2 mL) was added and the resulting mixture was stirred overnight at room temperature. Solvent was removed to get 0.04 g of the title compound as hydrochloride salt with quantitative yield.

¹H-NMR (400 MHz, DMSO): δ 1.74 (1H, m), 1.92-2.17 (1H, m), 3.03-3.51 (7H, m), 3.89 (6H, m), 4.14 (3H, s), 7.54-7.81 (4H, m), 7.83-7.91 (2H, m), 7.96-8.02 (2H, m); m/z 404 (M+H)$^+$, retention time (method a)=0.20 (10 min run)

Example 2

{(R)-1-[3-(1H-Benzoimidazol-2-yl)-4-chloro-phenyl]-piperidin-3-yl}-pyrrolidin-1-yl-methanone Method B—Step a To a vial with (R)-1-[3-(1H-Benzoimidazol-2-yl)-4-chloro-phenyl]-piperidine-3-carboxylic acid hydrochloride (obtained as described in general method 2, step e) (0.10 g, 0.28 mmol) (obtained as described in general method 2), HATU (0.11 g, 0.30 mmol), triethylamine (TEA) (0.09 mL, 0.66 mmol) and tert-Butyl-1-piperazinecarboxylate (0.08 g, 0.62 mmol) dichloromethane (2 L) was added and the reaction mixture was heated at 35° C. overnight. Reaction was cooled to room temperature, solvent removed and the crude purified by preparative HPLC and NH2 column filtration, to obtain 0.06 g of the title compound (55%).

¹H-NMR (400 MHz, DMSO): δ 1.59-2.06 (8H, m), 2.75-2.89 (2H, m), 2.94 (2H, t), 3.35-3.48 (2H, m), 3.84 (2H, t), 7.12 (1H, dd), 7.24-7.32 (2H, m), 7.37-7.44 (2H, m), 7.55-7.72 (1H, bs); m/z 409 (M+H)$^+$, retention time (method a)=2.27 (10 min run)

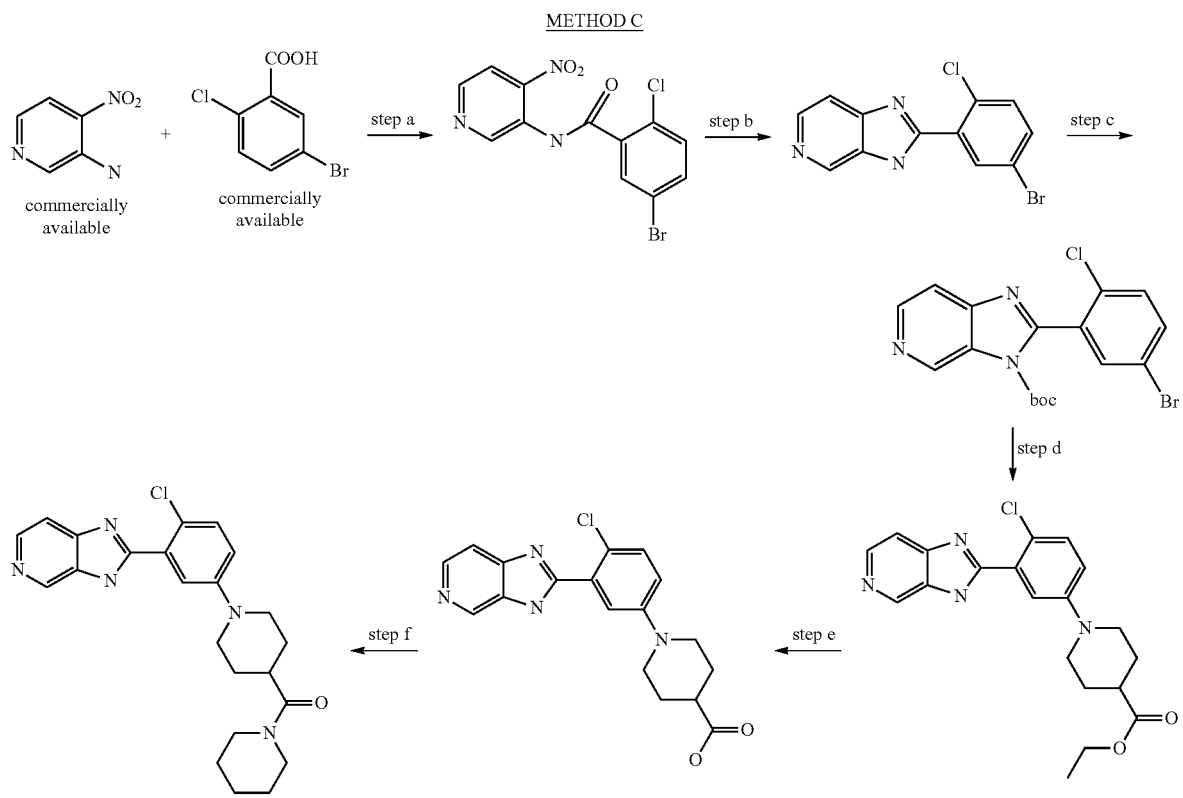

METHOD C

Example 3

{1-[4-Chloro-3-(3H-imidazo[4,5-c]pyridin-2-yl)-phenyl]-piperidin-4-yl}-piperidin-1-yl-methanone

5-Bromo-2-chloro-N-(4-nitro-pyridin-3-yl)-benzamide

Method C—Step a To a mixture of 5-Bromo-2-chlorobenzoic acid (5.00 g, 21.23 mmol) in DMF (40 mL), HATU (8.48 g, 22.29 mmol) and triethylamine (2.97 mL, 21.44 mmol) were added. After 30 min stirring at room temperature 4-nitro-pyridin-3ylamine (2.36 g, 16.99 mmol) was added, the reaction mixture stirred at 40° C. overnight and solvent removed. The crude was then diluted with EtOAc (40 mL) and washed first with saturated $Na_2CO_3$ solution (6×30 mL) then 1N HCl (3×30 mL). The organic layer was dried over $Na_2SO_4$, filtered and left standing. The precipitate obtained was filtered to get 4.75 g of the title compound (63%).

$^1$H-NMR (400 MHz, DMSO): δ 7.56 (1H, d), 7.77-7.92 (3H, m), 8.82 (1H, d), 9.14 (1H, s), 11.35 (1H, s); m/z 355 $(M+H)^+$, retention time (method a)=2.32 (5 min run)

2-(5-Bromo-2-chloro-phenyl)-3H-imidazo[4,5-c]pyridine

Method C—Step b To a mixture of 5-Bromo-2-chloro-N-(4-nitro-pyridin-3-yl)-phenylamine (0.50 g, 1.47 mmol) in acetic acid (6 mL), iron (0.16 g, 2.94 mmol) was added, and the reaction heated at 80° C. for 1.5 h. Then the reaction mixture was cooled to room temperature. Water was added (30 mL) and extractions with dcm (20 mL) were done to removed the non reacted starting material. Then to the acqueous layer saturated Rochelle salt solution (50 mL) and saturated $Na_2CO_3$ solution (30 mL) were added, and then extractions were done with dcm (20 mL). The organic layer was dried over $Na_2SO_4$, filtered and evaporated under reduced pressure to obtain 0.28 g of the title compound (65%) without further purifications.

$^1$H-NMR (400 MHz, MeOD): δ 7.45 (1H, d), 7.59-7.68 (2H, m), 7.98 (1H, d), 8.26 (1H, d), 8.87 (1H, s); m/z 309 $(M+H)^+$, retention time (method a)=1.13 (5 min run)

2-(5-Bromo-2-chloro-phenyl)-imidazo[4,5-c]pyridine-3-carboxylic acid tert-butyl ester Method C—Step c To a mixture of 2-(5-Bromo-2-chlorophenyl)-3H-imidazo[4,5-c]pyridine in dcm (50 mL), $Boc_2O$ (0.36 g, 16.36 mmol) and DMAP (0.20 g, 1.63 mmol) were added and the reaction mixture was left stirring at room temperature overnight. The solvent was then removed under reduced pressure and the crude was purified by filtration through a Si column (ethyl acetate as eluent) to obtain 4.80 g of the title compound (80%).

$^1$H-NMR (400 MHz, MeOD): δ 1.41 (18H, d), 7.52 (2H, dd), 7.73-7.87 (5H, m), 8.15 (1H, dd), 8.56 (2H, t), 9.02 (1H, s), 9.38 (1H, s); m/z 409 $(M+H)^+$, retention time (method b)=2.03 (5 min run)

1-[4-Chloro-3-(3H-imidazo[4,5-c]pyridin-2-yl)-phenyl]-piperidine-4-carboxylic acid ethyl ester Method C—Step d 2-(5-Bromo-2-chloro-phenyl)-imidazo[4,5-c]pyridine-3-carboxylic acid tert-butyl ester (0.50 g, 1.23 mmol), tris(dibenzylideneacetone) dipalladium(0) ($Pd_2 dba_3$) (0.13 g, 0.18 mmol), 2-dicyclohexylphosphino-2',4',6'-triisopropylbiphenyl (Xphos) (0.17 g, 0.37 mmol) and cesium carbonate (1.20 g, 3.68 mmol) were placed into a dried schlenk and few cycles of vacuum/nitrogen were performed. Then dry dioxane (2.00 mL) and piperidine-4-carboxylic acid ethyl ester (0.38 mL, 2.45 mmol) were added, the reaction mixture was heated at 80° C. for 4 h, left cooling to room temperature and filtered through sodium sulphate (Na$_2$SO$_4$). The crude was purified by flash chromatography (eluent gradient: EtOAc 100% to EtOAc:MeOH/95:5), to obtain 0.60 g of a mixture of the title compound and the starting material deprotected (7:3). The mixture was used for the next step.

$^1$H-NMR (400 MHz, MeOD): δ 1.26 (3H, t), 1.71-1.92 (2H, m), 1.92-1.94 (2H, m), 2.45-2.59 (1H, m), 2.88 (2H, t), 3.71-3.80 (2H, m), 4.06-4.22 (2H, q), 7.11-7.18 (dd, 1H), 7.42 (2H, q), 7.67 (1H, d), 8.35 (1H, d), 8.94 (1H, s); m/z 384 (M+H)$^+$, retention time (method b)=2.42 (5 min run)

1-[4-Cloro-3-(3H-imidazo[4,5-c]pyridin-2-yl)-phenyl]-piperidine-4-carboxylic acid hydrochloride Method C—Step e A mixture of 1-[4-Chloro-3-(3H-imidazo[4,5-c]pyridin-2-yl)-phenyl]piperidine-4-carboxylic acid ethyl ester (0.60 g, 1.56 mmol) in 6N HCl (15 mL) was heated in microwave at 120° C. for 20 minutes; 2 cycles were needed to complete conversion. Then solvent was removed under vacuum to obtain 0.61 g of a mixture of the title compound and 2-(5-Bromo-2-chloro-phenyl)-3H-imidazo[4,5-c]pyridine (coming from the previous step), with a ratio of 7:3.

$^1$H-NMR (400 MHz, CD3OD): δ 2.27-2.38 (4H, m), 2.90 (1H, m), 3.80-3.87 (4H, m), 7.63 (1H, dd), 7.91 (1H, m), 8.25 (1H, d), 8.37 (1H, m), 8.64 (1H, d), 9.43 (1H, s).

{1-[4-Chloro-3-(3H-imidazo[4,5-c]pyridin-2-yl)-phenyl]-piperidin-4-yl}-piperidin-1-yl-methanone Method C—Step f A mixture of 1-[4-Cloro-3-(3H-imidazo [4,5-c]pyridin-2-yl)-phenyl]-piperidine-4-carboxylic acid hydrochloride (0.09 g, 0.25 mmol), HATU (0.10 g, 0.26 mmol), triethylamine (TEA) (0.08 mL, 0.55 mmol), piperidine (0.03 g, 0.31 mmol) and dichloromethane (2 mL) was heated at 35° C. overnight. Reaction was cooled to room temperature, washed with ammonium chloride solution (3 mL) and the crude was purified by SCX (eluent: NH3 2N in MeOH) and flash chromatography (eluent: AcOEt:MeOH, 9:1), to obtain 0.04 g of the title compound (37%).

$^1$H-NMR (400 MHz, CD3OD): δ 1.54-1.70 (6H, m), 1.79-1.91 (4H, m), 2.83-2.92 (3H, m), 3.53-3.59 (4H, m), 3.86 (2H, d), 7.16 (1H, dd), 7.43 (2H, m), 7.69 (1H, d), 8.36 (1H, d), 8.94 (1H, s); m/z 424 (M+H)$^+$, retention time (method b)=3.38 (10 min run)

Example 4

(3-Dimethylamino-pyrrolidin-1-yl)-{(S)-1-[3-(1-methyl-1H-benzoimidazol-2-O-phenyl]-piperidin-3-yl}-methanone Method D—Step a To a vial with (S)-1-[3-(1-Methyl-1H-benzoimidazol-2-yl)-phenyl]-piperidine-3-carboxylic acid hydrochloride (obtained as described in general method 1, step d) (0.10 g, 0.27 mmol) (obtained as described in method A, step d) and HATU (0.11 g, 0.28 mmol), TEA (0.08 mL, 0.59 mmol) and dichloromethane (2 mL) were added, then dimethyl-pyrrolidin-3-yl-amine (0.04 mL, 0.33 mmol) was added. The reaction mixture was heated at 35° C. overnight, then ammonium chloride solution (2 mL) was added and the biphase solution stirred for some minutes. The organic layer was recovered and the crude was purified by SCX column (eluent from dcm:MeOH 1:1 to 2N NH3 in MeOH), and PrepHPLC to obtain 0.07 g of the diastereoisomeric mixture of title compound as formiate salt (65%).

$^1$H-NMR (400 MHz, CD$_3$OD): 1.62-2.11 (m, 10H); 2.66-2.39 (m, 2H); 2.53 (d, J=2.3 Hz, 6H); 2.61 (d, J=2.3 Hz, 6H); 2.78-2.99 (m, 6H), 3.35 (m, 4H), 3.50 (m, 1H); 3.62-3.73 (m, 2H); 3.82-3.90 (m, 12H); 4.02 (m, 1H), 7.19 (m, 4H); 7.32 (m, 6H); 7.44 (m, 2H); 7.56 (m, 2H); 7.68 (m, 2H) 8.33 (s, 2H); m/z 432 (M+H)$^+$, retention time (method a)=0.70 (10 min run)

METHOD D

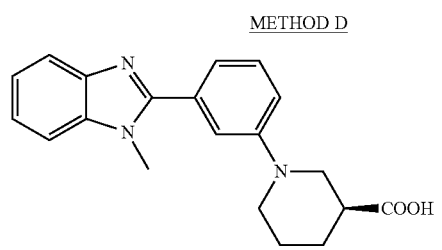

step a →

METHOD E

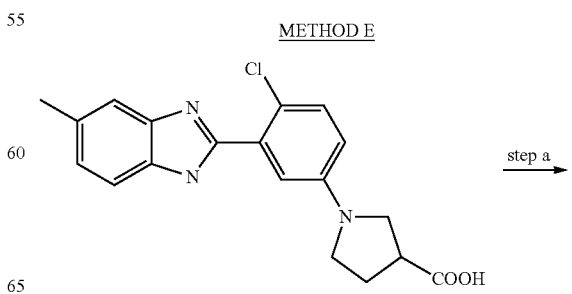

step a →

-continued

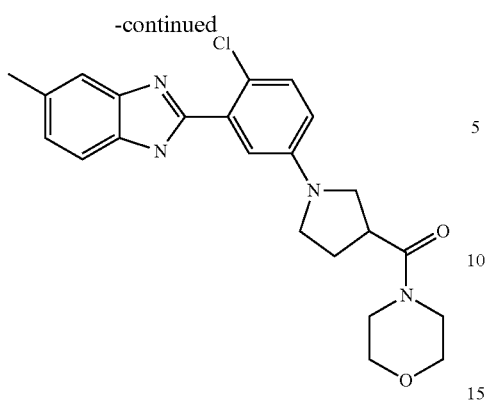

Example 5

{1-[4-Chloro-3-(5-methyl-1H-benzoimidazol-2-yl)-phenyl]-pyrrolidin-3-yl}-morpholin-4-yl-methanone Method E—Step a To a vial with 1-[4-Chloro-3-(5-methyl-1H-benzoimidazol-2-yl)-phenyl]-pyrrolidine-3-carboxylic acid (obtained as described in general method 5, step b) (0.09 g, 0.25 mmol), HATU (0.10 g, 0.26 mmol), TEA (0.07 mL, 0.53 mmol) and morpholine (0.03 mL, 0.33 mmol) dichloromethane (2 mL) was added and the reaction mixture was heated at 35° C. overnight. Reaction was cooled to room temperature, saturated $NaHCO_3$ solution (2 mL) was added with stirring, the organic layer recovered by filtration through phase separator, and the solvent removed under reduced pressure. The crude was purified by NH2 column (eluent: dichloromethane:MeOH from 10:0 to 5:5), and SCX to obtain 0.05 g of the title compound (46%).

$^1$H-NMR (400 MHz, $CD_3OD$): δ 2.20-2.32 (2H, m), 2.48 (3H, s), 3.34-3.52 (3H, m), 3.53-3.63 (4H, m), 3.64-3.72 (6H, m), 6.71 (1H, dd), 7.01 (1H, d), 7.12 (1H, d), 7.34 (1H, d), 7.41 (1H, s), 7.50 (1H, d); m/z 425 (M+H)$^+$, retention time (method a)=2.13 (10 min run)

METHOD F

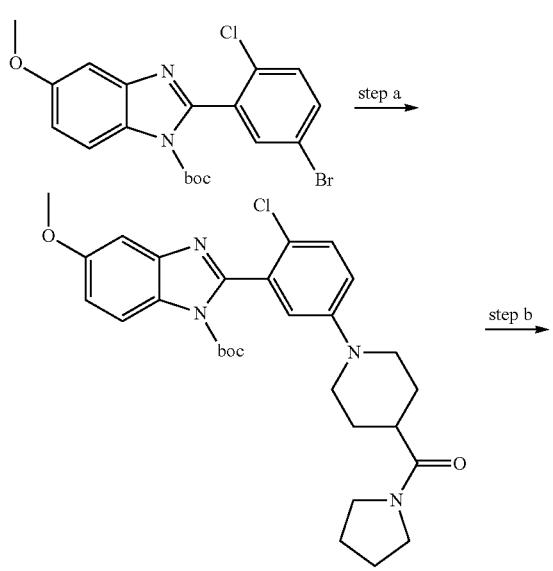

-continued

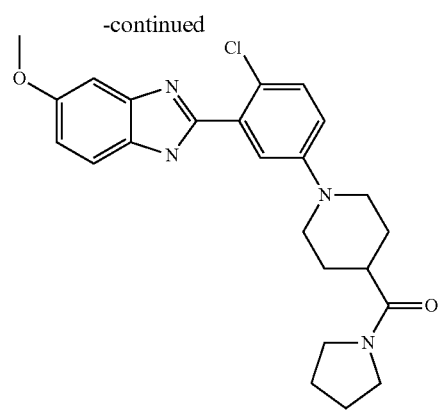

Example 6

{1-[4-Chloro-3-(5-methyoxy-1H-benzoimidazol-2-yl)-phenyl]-pyrrolidin-4-yl}-pyrrolidin-1-yl-methanone formate 2-{2-Chloro-5-[4-(pyrrolidine-1-carbonyl)-piperidin-1-yl]-phenyl}-5-methoxy-benzoimidazole-1-carboxylic acid tert-butyl ester Method F—Step a 2-(5-Bromo-2-chloro-phenyl)-5-methoxy-benzoimidazole-1-carboxylic acid tert-butyl ester (obtained as described in general method 4, step c) (0.10 g, 0.23 mmol), piperidin-4-yl-pyrrolidin-1-yl-methanone (0.05 g, 0.30 mmol) and cesium carbonate (0.37 g, 1.14 mmol) were placed into a dried vial and 3 cycles of vacuum/nitrogen were performed, then dry toluene (0.20 mL) was added. At the same time palladium acetate (0.01 g, 0.05 mmol), and BINAP (0.04 g, 0.07 mmol) were placed into a dried 4 mL vial under nitrogen and 3 cycles of vacuum/nitrogen were performed. Then dry toluene (0.40 mL) was added, at room temperature under nitrogen, and the mixture was added to the first vial. The reaction mixture was heated at 80° C. overnight, cooled to room temperature, EtOAC (3 mL) was added and the mixture filtered off. Solvent was removed and the crude recovered with EtOAc (3.5 mL) and filtered through a 2 g silica column (eluent EtOAc) to afford 0.10 g of the title compound (82%) without further purifications.

{1-[4-Chloro-3-(5-methyoxy-1H-benzoimidazol-2-yl)-phenyl]-pyrrolidin-4-yl}-pyrrolidin-1-yl-methanone formate Method F—Step b To a mixture of 2-{2-Chloro-5-[4-(pyrrolidine-1-carbonyl)-piperidin-1-yl]-phenyl}-5-methoxy-benzoimidazole-1-carboxylic acid tert-butyl ester (0.10 g, 0.19 mmol) in 2M HCl in $Et_2O$ (2 mL), few drops of dichloromethane and methanol were added to improve the solubility of the starting material. The resulting mixture was stirred overnight at room temperature, Et2O was added (5 mL), the precipitate was filtered off and then purified by PrepHPLC to get 0.03 g of the title compound as hydrochloride salt, with quantitative yield.

$^1$H-NMR (400 MHz, $CD_3OD$): δ 1.83-1.93 (6H, m), 1.95-2.04 (2H, m), 2.65-2.74 (1H, m), 2.79-2.90 (2H, m), 3.41 (2H, t), 3.60 (2H, t), 3.81-3.88 (2H, m), 3.86 (3H, s), 6.92 (1H, dd), 7.07-7.14 (2H, m), 7.37-7.41 (2H, 7.51 (1H, d); m/z 439 (M+H)$^+$, retention time (method a)=2.23 (10 min run)

METHOD G

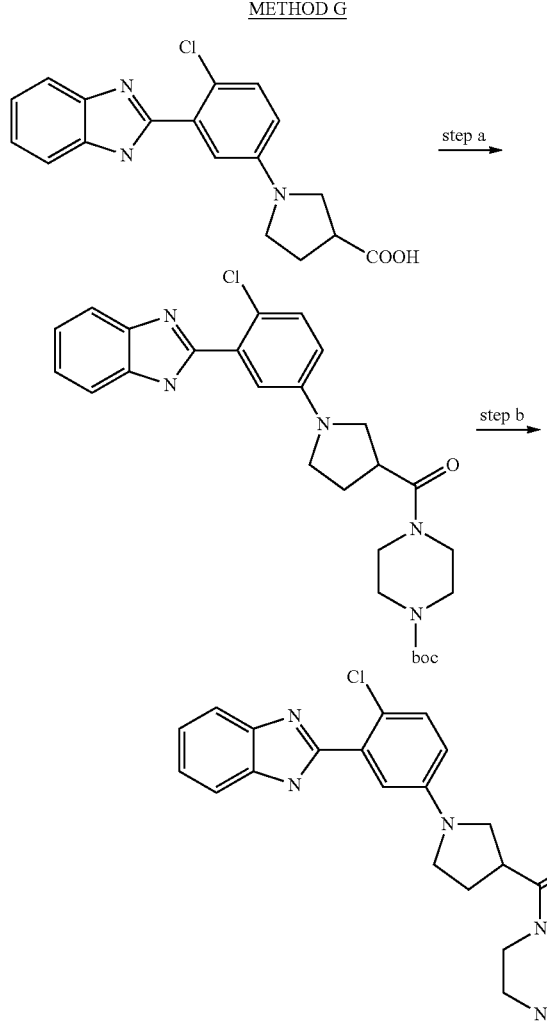

Example 7

{1-[3-(1H-Benzoimidazol-2-yl)-4-chloro-phenyl]-pyrrolidin-3-yl}-piperazin-1-yl-methanone 4-{1-[3-(1H-Benzoimidazol-2-yl)-4-chloro-phenyl]-pyrrolidine-3-carbonyl}-piperazine-1-carboxylic acid tert-butyl ester Method G—Step a To a mixture of 1-[3-(1H-Benzoimidazol-2-yl)-4-chloro-phenyl]-pyrrolidine-3-carboxylic acid (obtained as described in general method 2, step e) (0.01 g, 0.26 mmol) in dcm (4 mL), HATU (0.10 g, 0.29 mmol), diisopropylethylamine (DIPEA) (0.14 mL, 0.76 mmol) and tert-butyl-1-piperazine carboxylate (0.06 g, 0.32 mmol) were added. The reaction mixture was heated at 35° C. overnight, cooled to room temperature and washed with water (2×5 mL) and saturated Na$_2$CO$_3$ solution (2×5 mL). The organic layer was dried over Na$_2$SO$_4$, filtered and evaporated under reduced pressure to obtain a crude that was triturated with diethylether (3 mL), filtered and dried. The precipitate was then purified by flash chromatography (eluent gradient: EtOAc 100% to EtOAc:NH3 in MeOH (2M)/4:0.8), and then a filtration on an SCX cartridge was run (eluent gradient: DCM:MeOH/1:1 to NH3 in MeOH), to obtain 0.11 g of the title compound (67%).

{1-[3-(1H-Benzoimidazol-2-yl)-4-chloro-phenyl]-pyrrolidin-3-yl}-piperazin-1-yl-methanone Method G—Step b To a mixture of 4-{1-[3-(1H-Benzoimidazol-2-yl)-4-chloro-phenyl]-pyrrolidine-3-carbonyl}-piperazine-1-carboxylic acid tert-butyl ester (0.11 g, 0.21 mmol) in dcm (1 mL), 2M HCl in Et$_2$O (4 mL) was added. The mixture was stirred at room temperature overnight, the precipitate obtained was filtered off, and washed with Et$_2$O. The precipitate was then recovered in saturated NaHCO$_3$ solution (3 mL), extracted with dcm (2×3 mL), solvent removed and the crude filtered through an SCX cartridge, to obtain 0.05 g of the title compound (57%).

$^1$H-NMR (400 MHz, CD3OD): δ 2.09-2.23 (2H, m), 2.69-2.78 (4H, m), 3.28-3.44 (3H, m), 3.47-3.56 (6H, m), 6.61-6.64 (1H, m), 6.92-6.93 (1H, m), 7.16-7.20 (2H, m), 7.24-7.27 (1H, m), 7.53 (2H, bs); m/z 410 (M+H)$^+$, retention time (method b)=0.88 (10 min run)

METHOD H

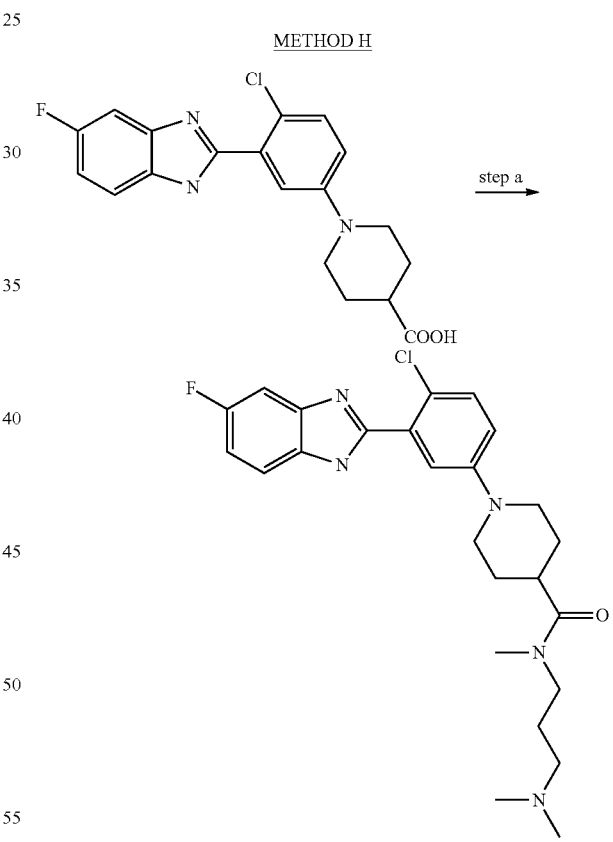

Example 8

1-[4-Chloro-3-(5-fluoro-1H-benzoimidazol-2-yl)-phenyl]-piperidine-4-carboxylic acid (3-dimethylamino-propyl)-methyl-amide Method H—Step a To a vial with 1-[4-Chloro-3-(5-fluoro-1H-benzoimidazol-2-yl)-phenyl]-piperidine-4-carboxylic acid (obtained as described in general method 3,4, step e) (0.10 g, 0.26 mmol) and HATU (0.10 g, 0.27 mmol) in dichloromethane (2 mL), TEA (0.07 mL, 0.54 mmol) and N,N,N'-trimethyl-1,3-propanediamine (0.32 mmol, 0.05 mL) were added. The reaction mixture was heated at 35° C. overnight, solvent was removed and the crude was purified by PrepHPLC and SCX column to obtain 0.06 g of the title compound (49%).

$^1$H-NMR (400 MHz, DMSO): δ 1.50-1.72 (6H, m), 2.15 (8H, m), 2.80 (4H, m), 3.02 (2H, s), 3.30 (2H, m), 3.70 (2H, m), 7.06 (2H, m), 7.28-7.56 (3H, m), 7.69 (1H, m), 12.74 (1H, s); m/z 472 (M+H)$^+$, retention time (method a)=1.68 (10 min run)

METHOD I

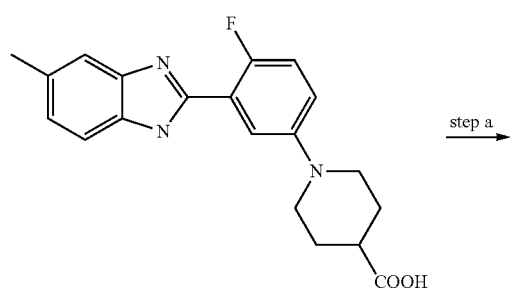

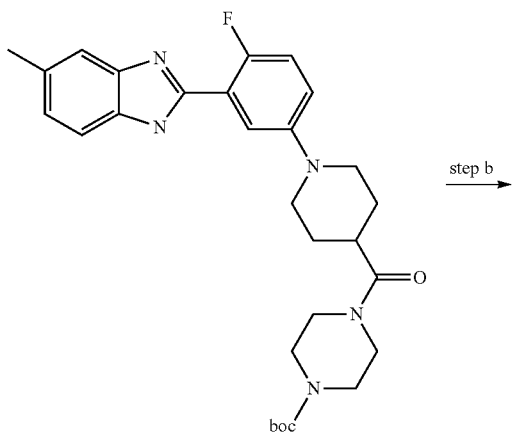

Example 9

{1-[4-Fluoro-3-(5-methyl-1H-benzoimidazol-2-yl)-phenyl]-piperidin-4-yl}-piperazin-1-yl-methanone 4-{1-[4-Fluoro-3-(5-methyl-1H-benzoimidazol-2-yl)-phenyl]-piperidine-4-carbonyl}-piperazine-1-carboxylic acid tert-butyl ester Method I—Step a To a vial with [1-[4-Fluoro-3-(5-methyl-1H-benzoimidazol-2-yl)-phenyl]-piperidine-4-carboxylic acid hydrochloride (obtained as described in general method 8, step b) (0.10 g, 0.26 mmol) and HATU (0.10 g, 0.27 mmol) in dichloromethane (2 mL), TEA (0.08 mL, 0.56 mmol) and tert-butyl-1-piperazinecarboxylate (0.32 mmol, 0.06 g) were added. The reaction mixture was heated at 35° C. overnight, washed with water (3×2 mL) and saturated Na$_2$CO$_3$ solution (3×2 mL). The crude was then purified by flash chromatography (eluent: EtOAc), and then a filtration on an NH2 cartridge was run (eluent EtOAc), to obtain 0.02 g of the title compound (15%).

{1-[4-Fluoro-3-(5-methyl-1H-benzoimidazol-2-yl)-phenyl]-piperidin-4-yl}-piperazin-1-yl-methanone Method I—Step b A mixture of 4-{1-[4-Fluoro-3-(5-methyl-1H-benzoimidazol-2-yl)-phenyl]-piperidine-4-carbonyl}-piperazine-1-carboxylic acid tert-butyl ester (0.02 g, 0.04 mmol) in 2M HCl in Et$_2$O (3 mL) was stirred for 2 days at room temperature, then solvent was removed and the crude filtered through an NH2 cartridge (eluent EtOAc), to obtain 0.02 g of the title compound with quantitative yield.

$^1$H-NMR (400 MHz, CDCl$_3$): δ 1.83 (2H, m), 1.96-2.07 (2H, m), 2.50 (3H, s), 2.56-2.63 (1H, m), 2.77-2.93 (6H, m), 3.58 (4H, d), 3.79 (2H, d), 6.98 (1H, m), 7.10 (2H, m), 7.29-7.39 (1H, m), 7.62-7.72 (1H, m), 8.00 (1H, dd), 9.78 (1H, bs); m/z 421 (M+H)$^+$, retention time (method a)=1.37 (10 min run)

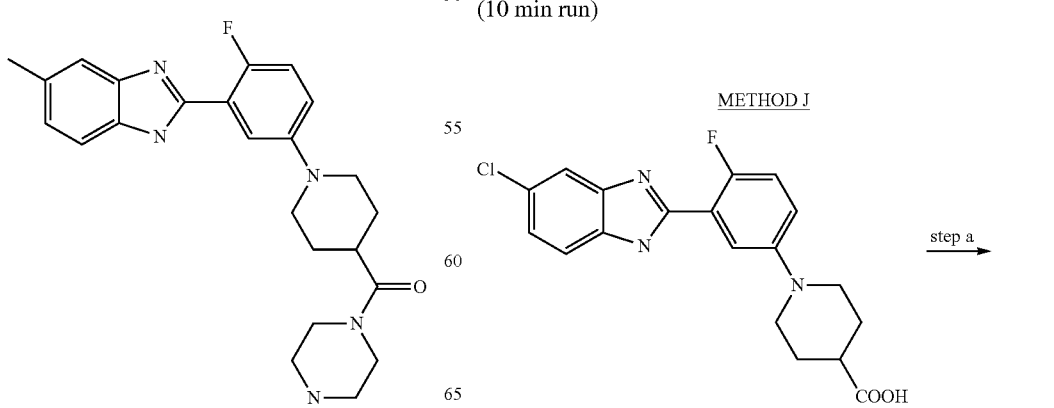

METHOD J

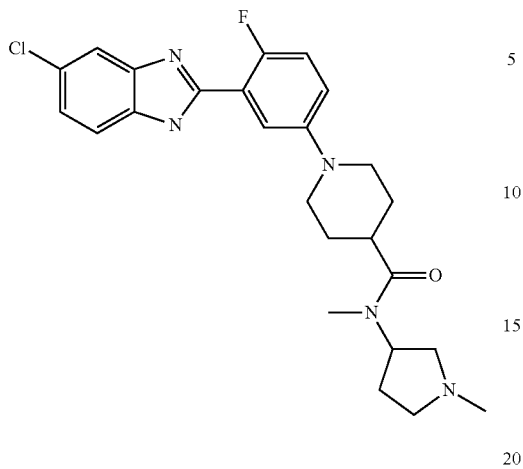

Example 10

1-[3-(5-Chloro-1H-benzoimidazol-2-yl)-4-fluoro-phenyl]piperidine-4-carboxylic acid methyl-(1-methyl-pyrrolidin-3-yl) amide Method J—Step a To a mixture of 1-[3-(5-Chloro-1H-benzoimidazol-2-yl)-4-fluoro-phenyl]-piperidine-4-carboxylic acid hydrochloride (obtained as described in general method 10, step b) (0.01 g, 0.25 mmol) in dcm (2 mL), HATU (0.10 g, 0.26 mmol), TEA (0.07 mL, 0.55 mmol) and N,N'-dimethyl-3-aminopyrrolidine (0.04 g, 0.31 mmol) were added. The reaction mixture was heated at 35° C. overnight, cooled to room temperature and washed with ammonium chloride solution (2 mL), saturated $Na_2CO_3$ solution (2 mL) and water (2 mL). The organic layer was then filtrated on an NH2 cartridge and further purified by flash chromatography (eluent: EtOAc:NH3 2N in MeOH/9:1) to obtain 0.03 g of the title compound (30%).

$^1$H-NMR (400 MHz, CD3OD): δ 1.79-1.94 (5H, m), 2.08-2.30 (2H, m), 2.37 (3H, s), 2.46-2.54 (2H, m), 2.62-2.69 (2H, m), 2.72-2.92 (2H, m), 3.10 (3H, s), 3.79 (2H, d), 5.16 (1H, m), 7.14-7.20 (2H, m), 7.26 (1H, dd), 7.58-7.63 (2H, m), 7.73 (1H, dd); m/z 470 (M+H)$^+$, retention time (method b)=1.80 (10 min run)

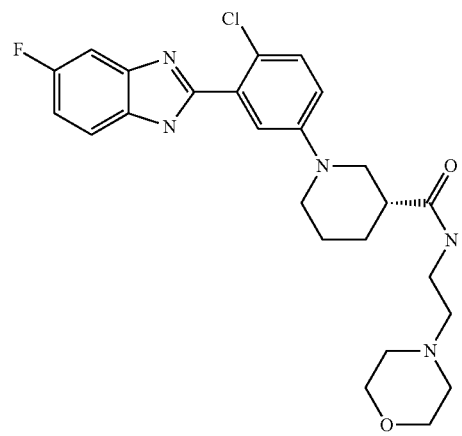

Example 11

(R)-1-[4-Chloro-3-(5-fluoro-1H-benzoimidazol-2-yl)-phenyl]-piperidine-3-carboxylic acid (2-morpholin-4-yl-ethyl)-amide Method K—Step a To a mixture of (R)-1-[4-Chloro-3-(5-fluoro-1H-benzoimidazol-2-yl)-phenyl]-piperidine-3-carboxylic acid hydrochloride (obtained as described in general method 3,4, step e) (0.01 g, 0.27 mmol) in dcm (2 mL), HATU (0.10 g, 0.28 mmol), TEA (0.08 mL, 0.56 mmol) and 2-morpholinoethylamine (0.04 g, 0.33 mmol) were added. The reaction mixture was stirred at room temperature overnight, washed with ammonium chloride solution (2 mL), filtered through a phase separator and organic solvent was removed. The crude was then purified by SCX column and flash chromatography (eluent: gradient from EtOAc to EtOAc:NH3 in MeOH (2M)/10:1) to obtain 0.05 g of the title compound (40%).

$^1$H-NMR (400 MHz, CD$_3$OD): δ 1.66-1.98 (4H, m), 2.40-2.64 (7H, m), 2.94 (1H, m), 3.06 (1H, dd), 3.36 (2H, m), 3.57-3.80 (6H, m), 7.04-7.16 (2H, m), 7.33 (13H, bs), 7.42 (2H, m), 7.62 (1H, bs); m/z 486 (M+H)$^+$, retention time (method b)=2.97 (10 min run)

METHOD K

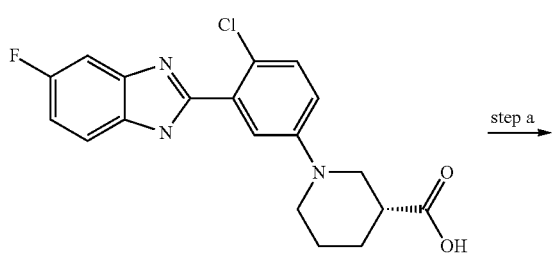

step a

METHOD L

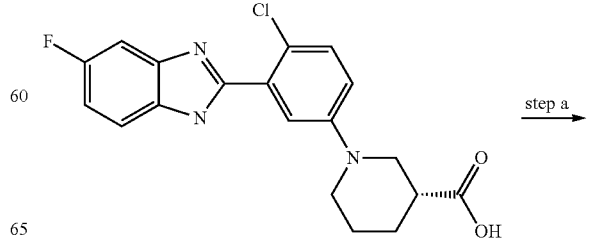

step a

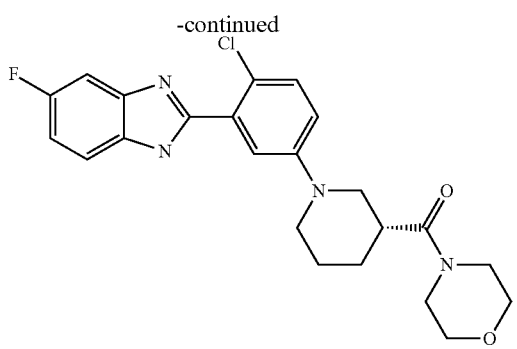

Example 12

{(R)-1-[4-Chloro-3-(5-fluoro-1H-benzoimidazol-2-yl)-phenyl]-piperidin-3-yl}-morpholin-4-yl-methanone Method L—Step a To a mixture of (R)-1-[4-Chloro-3-(5-fluoro-1H-benzoimidazol-2-yl)-phenyl]-piperidine-3-carboxylic acid hydrochloride (obtained as described in general method 3,4, step e) (0.01 g, 0.27 mmol) in dcm (2 mL), HATU (0.10 g, 0.28 mmol), TEA (0.08 mL, 0.56 mmol) and 2-morpholinoethylamine (0.04 g, 0.33 mmol) were added. The reaction mixture was stirred at room temperature overnight, washed with ammonium chloride solution (2 mL), filtered through a phase separator and organic solvent was removed. The crude was then purified by SCX column and flash chromatography (eluent: gradient from cyclohexane:EtOAc/1:1 to 0:1 to EtOAc:NH3 in MeOH (2M)/10:1). A further purification by preparative HPLC was done to obtain 0.03 g of the title compound (29%).

$^1$H-NMR (400 MHz, CD$_3$OD): δ 1.57-1.88 (3H, m), 1.95 (1H, m), 2.81 (1H, td), 2.98 (2H, m), 3.50-3.85 (10H, m), 7.10 (2H, m), 7.32 (1H, m), 7.40 (2H, m), 7.60 (1H, m); m/z 443 (M+H)$^+$, retention time (method b)=4.98 (10 min run)

METHOD M

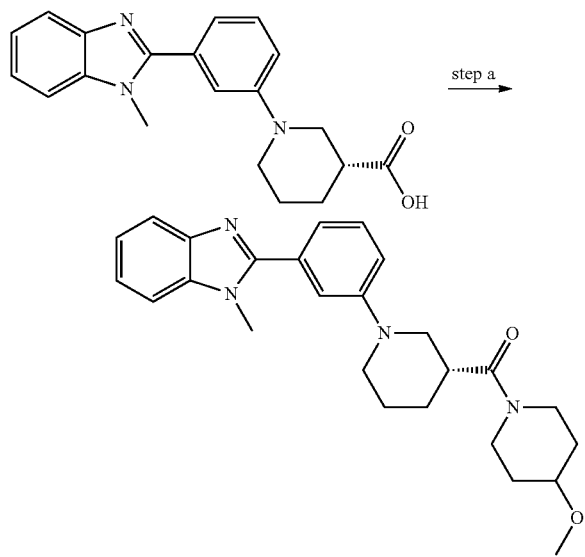

step a

Example 13

(4-Methoxy-piperidin-1-yl)-{(R)-1-[3-(1-methyl-1H-benzoimidazol-2-yl)-phenyl]-piperidin-3-yl}-methanone Method M—Step a To a mixture of (R)-1-[3-(1-methyl-1H-benzoimidazol-2-yl)-phenyl]-piperidine-3-carboxylic acid hydrochloride (obtained as described in general method 1, step d) (0.01 g, 0.30 mmol) (obtained as described in method A, step d) in dcm (2.5 mL), HATU (0.12 g, 0.33 mmol), TEA (0.09 mL, 0.63 mmol) and 4-methoxypiperidine (0.04 g, 0.33 mmol) were added. The reaction mixture was heated at 35° C. overnight, cooled to room temperature, washed with ammonium chloride solution (3 mL), filtered through a phase separator and organic solvent was removed. The crude was then purified by SCX column (eluent: first dcm:MeOH/1:1 then NH3 in MeOH (2N)) and flash chromatography (eluent: gradient from EtOAc:cyclohexane/10:0 to 0:10) to obtain 0.05 g of the title compound (38%).

$^1$H-NMR (400 MHz, CD3OD): δ 1.42-1.69 (3H, m), 1.73-1.96 (5H, m), 2.78-2.93 (1H, m), 2.93-3.07 (2H, m), 3.25-3.50 (6H, m), 3.79-3.94 (7H, m), 7.16-7.19 (2H, m), 7.28-7.36 (3H, m), 7.42-7.46 (1H, m), 7.54-7.56 (1H, m), 7.66-7.68 (1H, m); m/z 433 (M+H)$^+$, retention time (method b)=3.63 (10 min run)

METHOD N

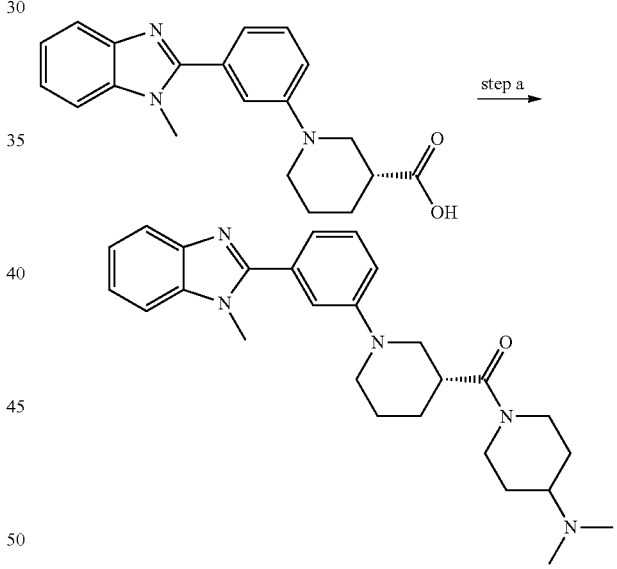

step a

Example 14

(4-Dimethylamino-piperidin-1-yl)-{(R)-1-[3-(1-methyl-1H-benzoimidazol-2-yl)-phenyl]-piperidin-3-yl}-methanone Method N—Step a To a mixture of (R)-1-[3-(1-methyl-1H-benzoimidazol-2-yl)-phenyl]-piperidine-3-carboxylic acid hydrochloride (obtained as described in general method 1, step d) (0.01 g, 0.30 mmol) (obtained as described in method A, step d) in dcm (2.5 mL), HATU (0.12 g, 0.33 mmol), TEA (0.09 mL, 0.63 mmol) and 4-(N,N-dimethylamino)piperidine (0.04 g, 0.35 mmol) were added. The reaction mixture was heated at 35° C. overnight, cooled to room temperature, washed with ammonium chloride solution (3 mL), filtered through a phase separator and organic solvent was removed. The crude was then purified by SCX column (eluent: first dcm:MeOH/1:1 then NH3 in MeOH (2N)) and flash chromatography (eluent: gradient from EtOAc:NH3 in MeOH (2N)/ 10:0 to 9:1) to obtain 0.05 g of the title compound (37%).

¹H-NMR (400 MHz, CD3OD): δ 1.26-1.43 (2H, m), 1.59-2.00 (6H, m), 2.26-2.31 (6H, m), 2.43-2.49 (1H, m), 2.57-2.64 (1H, m), 2.79-3.18 (4H, m), 3.79-3.86 (2H, m), 3.89 (3H, s), 4.12-4.16 (1H, m), 4.58-4.61 (1H, m), 7.16-7.20 (2H, m), 7.28-7.37 (3H, m), 7.42-7.46 (1H, m), 7.54-7.56 (1H, m), 7.66-7.68 (1H, m); m/z 446 (M+H)⁺, retention time (method b)=1.63 (10 min run)

¹H-NMR (400 MHz, CD3OD): δ 1.66-1.97 (4H, m), 2.42-2.50 (6H, m), 2.48 (3H, s), 2.55-2.62 (1H, m), 2.89-2.97 (1H, m), 3.06 (1H, dd), 3.28-3.41 (2H, m), 3.60 (4H, dd), 3.63-3.69 (1H, m), 3.71-3.77 (1H, m), 7.09-7.15 (2H, m), 7.38-7.54 (4H, m); m/z 482 (M+H)⁺, retention time (method b)=2.57 (10 min run)

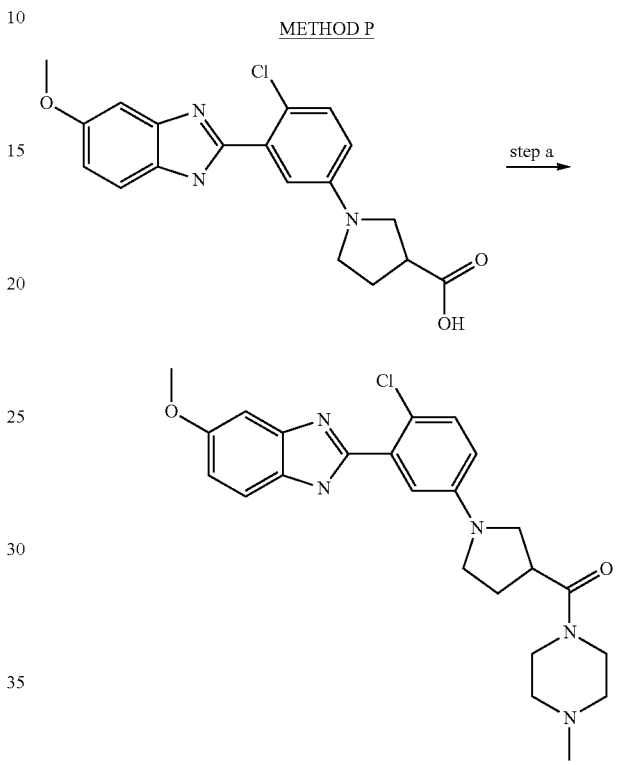

METHOD P

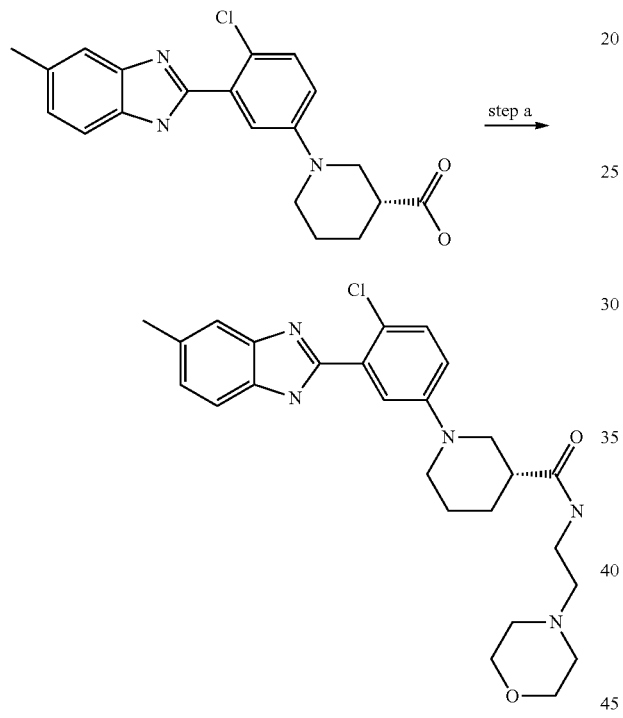

METHOD O

Example 15

(R)-1-[4-Chloro-3-(5-methyl-1H-benzoimidazol-2-yl)-phenyl]-piperidine-3-carboxylic acid (2-morpholin-4-yl-ethyl)-amide Method O—Step a To a vial with (R)-1-[4-Chloro-3-(5-methyl-1H-benzoimidazol-2-yl)-phenyl]-piperidine-3-carboxylic acid hydrochloride (obtained as described in general method 3,4, step e) (0.10 g, 0.25 mmol), HATU (0.10 g, 0.26 mmol), TEA (0.07 mL, 0.53 mmol) and 2-morpholin-4-yl-ethylamine (0.04 mL, 0.33 mmol), dichloromethane (2 mL) was added and the reaction mixture was heated at 35° C. overnight. Reaction was cooled to room temperature, saturated NaHCO3 solution (2 mL) was added with stirring, the organic layer recovered by filtration through phase separator, and the solvent removed under reduced pressure. The crude was purified by SCX and flash chromatography (eluent; gradient cyclohexane:ethylacetate from 100:0 to 3:1) to obtain 0.05 g of the title compound (42%).

Example 16

{1-[4-Chloro-3-(5-methoxy-1H-benzoimidazol-2-yl)-phenyl]-pyrrolidin-3-yl}-(4-methyl-piperazin-1-yl)-methanone Method P—Step a To a vial with 1-[4-Chloro-3-(5-methoxy-1H-benzoimidazol-2-yl)-phenyl]-pyrrolidine-3-carboxylic acid hydrochloride (obtained as described in general method 3,4, step e) (0.10 g, 0.25 mmol), HATU (0.10 g, 0.26 mmol), TEA (0.07 mL, 0.53 mmol) and 1-methyl-piperazine (0.04 mL, 0.33 mmol), dichloromethane (2 mL) was added and the reaction mixture was heated at 35° C. overnight. Reaction was cooled to room temperature, saturated NaHCO3 solution (2 mL) was added with stirring, the organic layer recovered by filtration through phase separator, and the solvent removed under reduced pressure. The crude was purified by SCX, trituration from diethyl ether and finally by preparative HPLC to obtain 0.04 g of the title compound (34%).

¹H-NMR (400 MHz, CD3OD): δ 2.20-2.33 (2H, m), 2.41 (3H, s), 2.51-2.66 (4H, m), 3.37-3.54 (3H, m), 3.56-3.76 (6H, m), 3.86 (3H, s), 6.71 (1H, dd), 6.93 (1H, ddd), 7.01 (1H, d), 7.12 (1H, d), 7.34 (1H, dd), 7.52 (1H, d); m/z 454 (M+H)⁺, retention time (method b)=2.13 (10 min run)

METHOD Q

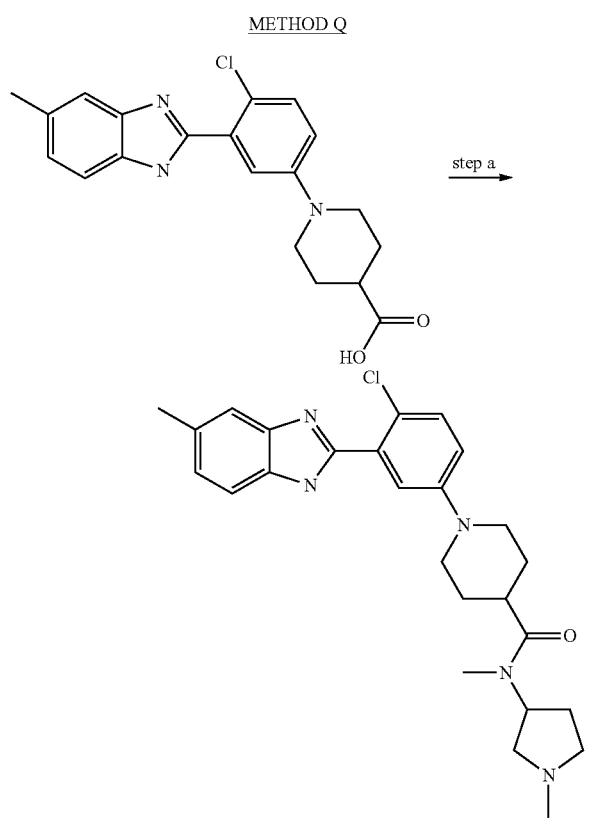

Example 17

1-[4-Chloro-3-(5-methyl-1H-benzoimidazol-2-yl)-phenyl]-piperidine-4-carboxylic acid methyl-(1-methyl-pyrrolidin-3-yl)-amide Method Q—Step a To a mixture of 1-[4-chloro-3-(5-methyl-1H-benzoimidazol-2-yl)-phenyl]-piperidine-4-carboxylic acid hydrochloride (obtained as described in general method 3,4, step e) (0.01 g, 0.25 mmol) in dcm (2 mL), HATU (0.10 g, 0.26 mmol), TEA (0.07 mL, 0.53 mmol) and methyl-(1-methyl-pyrrolidin-3-yl)-amine (0.03 g, 0.31 mmol) were added. The reaction mixture was heated at 35° C. overnight, cooled to room temperature, washed with ammonium chloride solution (2 mL), filtered through a phase separator and organic phase was filtered by SCX column (eluent: first dcm:MeOH/1:1 then NH3 in MeOH (2N)). This work up was done using the Zinsser Speedy (version 6.1.3). The crude was then purified by flash chromatography (eluent: gradient from EtOAc to EtOAc:NH3 in MeOH (2N)/10:1) to obtain 0.04 g of the title compound (37%). $^1$H-NMR (400 MHz, CD3OD): δ 1.76-1.93 (5H, m), 2.08-2.23 (2H, m), 2.36-2.48 (6H, m), 2.51-3.09 (9H, m), 3.83-3.86 (2H, m), 5.13-5.20 (1H, m), 7.09-7.13 (2H, m), 7.38-7.40 (3H, m), 7.51 (1H, bs); m/z 466 (M+H)$^+$, retention time (method b)=2.30 (10 min run)

The Table shows a selection of the compounds synthesised, which were prepared according to the method indicated in the third column of the table and above discussed in detail with the synthesis of examples 1 to 17.

TABLE

| Example | Structure | Synthesis method | Calculated mass | Found mass | LCMS r.t. | LCMS method |
|---|---|---|---|---|---|---|
| 18 | *structure* | G | 394.89708 | 395 | 2.18 | method a |
| 19 | *structure* | G | 423.93834 | 424 | 1.15 | method a |

TABLE-continued

| Example | Structure | Synthesis method | Calculated mass | Found mass | LCMS r.t. | LCMS method |
|---|---|---|---|---|---|---|
| 20 | 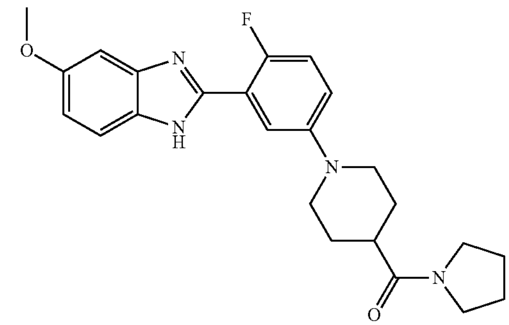 [SMILES: COc1ccc2[nH]c(-c3cc(N4CCC(C(=O)N5CCCC5)CC4)ccc3F)nc2c1] | F | 422.49534 | 423 | 2.13 | method a |
| 21 | 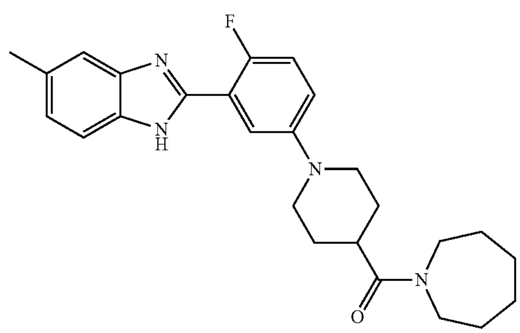 [SMILES: Cc1ccc2[nH]c(-c3cc(N4CCC(C(=O)N5CCCCCC5)CC4)ccc3F)nc2c1] | F | 434.5491 | 435 | 2.62 | method a |
| 22 | 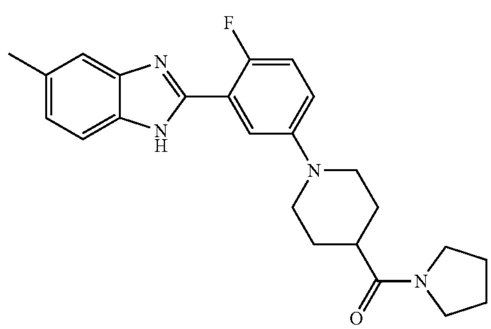 [SMILES: Cc1ccc2[nH]c(-c3cc(N4CCC(C(=O)N5CCCC5)CC4)ccc3F)nc2c1] | F | 406.49594 | 407 | 2.18 | method a |
| 23 | 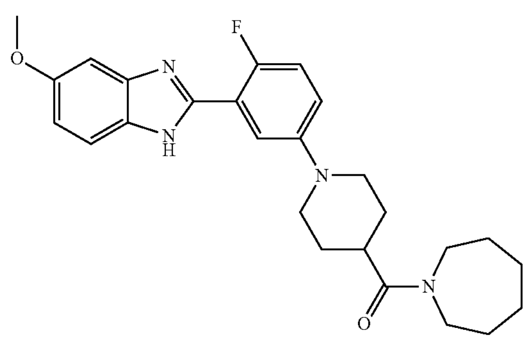 [SMILES: COc1ccc2[nH]c(-c3cc(N4CCC(C(=O)N5CCCCCC5)CC4)ccc3F)nc2c1] | F | 450.5485 | 451 | 2.55 | method a |

TABLE-continued

| Example | Structure | Synthesis method | Calculated mass | Found mass | LCMS r.t. | LCMS method |
|---|---|---|---|---|---|---|
| 24 | 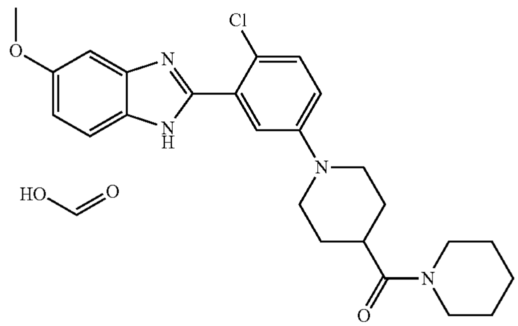 [SMILES: COc1ccc2[nH]c(-c3cc(N4CCC(C(=O)N5CCCCC5)CC4)ccc3Cl)nc2c1 ; O=CO] | F | 452.97622 | 453 | 2.47 | method a |
| 25 | 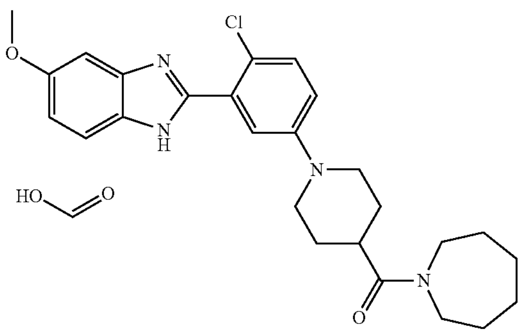 [SMILES: COc1ccc2[nH]c(-c3cc(N4CCC(C(=O)N5CCCCCC5)CC4)ccc3Cl)nc2c1 ; O=CO] | F | 468.0028 | 467 | 2.68 | method a |
| 26 | 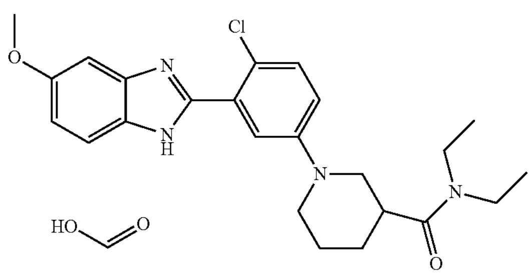 [SMILES: CCN(CC)C(=O)C1CCCN(c2ccc(Cl)c(-c3nc4cc(OC)ccc4[nH]3)c2)C1 ; O=CO] | F | 440.96552 | 441 | 2.48 | method a |
| 27 | 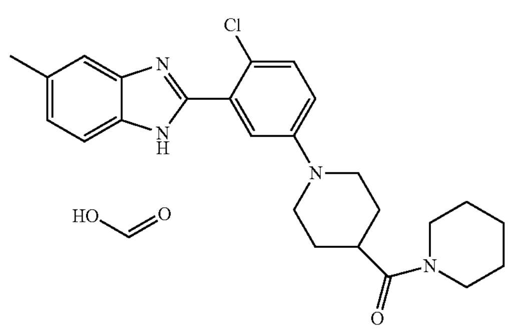 [SMILES: Cc1ccc2[nH]c(-c3cc(N4CCC(C(=O)N5CCCCC5)CC4)ccc3Cl)nc2c1 ; O=CO] | F | 436.97682 | 437 | 2.55 | method a |
| 28 | 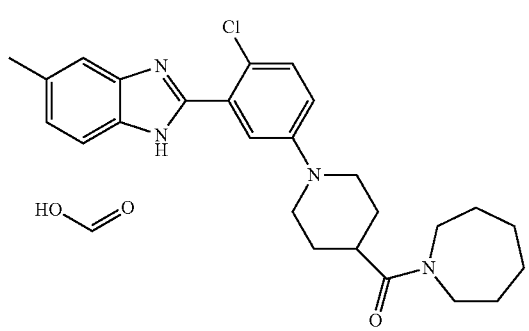 [SMILES: Cc1ccc2[nH]c(-c3cc(N4CCC(C(=O)N5CCCCCC5)CC4)ccc3Cl)nc2c1 ; O=CO] | F | 451.0034 | 451 | 2.7 | method a |

| Example | Structure | Synthesis method | Calculated mass | Found mass | LCMS r.t. | LCMS method |
|---|---|---|---|---|---|---|
| 29 | 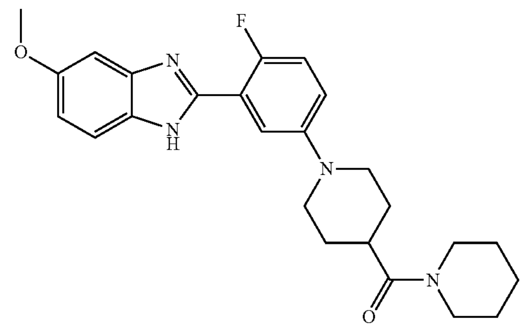 [SMILES: COc1ccc2[nH]c(-c3cc(N4CCC(C(=O)N5CCCCC5)CC4)ccc3F)nc2c1] | F | 436.52192 | 437 | 2.38 | method a |
| 30 | 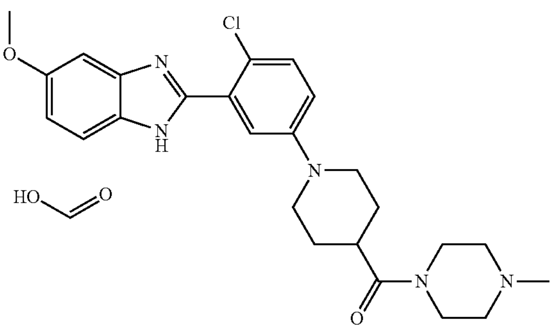 | F | 467.9909 | 468 | 1.35 | method a |
| 31 | 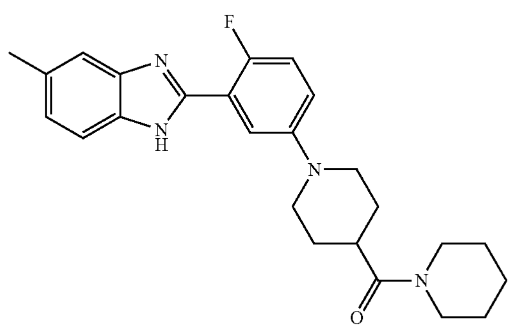 [SMILES: Cc1ccc2[nH]c(-c3cc(N4CCC(C(=O)N5CCCCC5)CC4)ccc3F)nc2c1] | F | 420.52252 | 421 | 2.43 | method a |
| 32 | 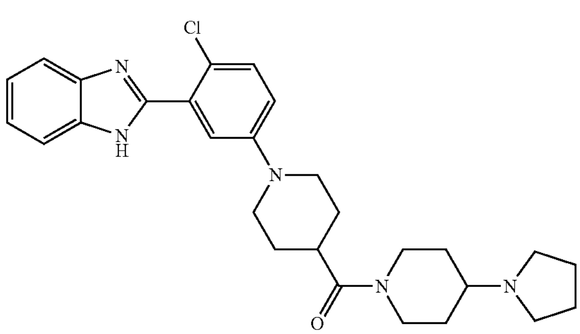 [SMILES: O=C(C1CCN(c2ccc(Cl)c(-c3nc4ccccc4[nH]3)c2)CC1)N1CCC(N2CCCC2)CC1] | H | 492.05536 | 492 | 1.38 | method a |

TABLE-continued
| Example | Structure | Synthesis method | Calculated mass | Found mass | LCMS r.t. | LCMS method |
|---|---|---|---|---|---|---|
| 33 | 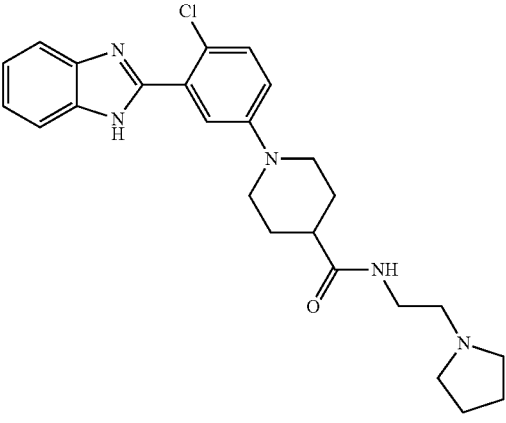 [SMILES: O=C(NCCN1CCCC1)C1CCN(c2ccc(Cl)c(-c3nc4ccccc4[nH]3)c2)CC1] | H | 451.9915 | 452 | 1.32 | method a |
| 34 | 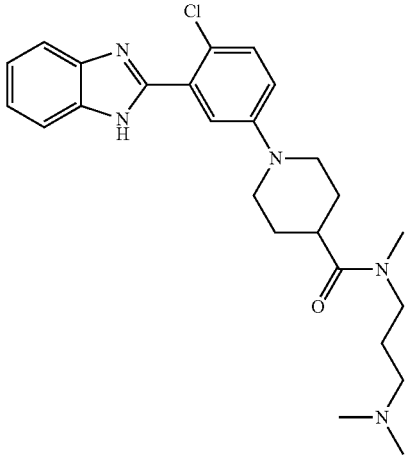 [SMILES: CN(C)CCCN(C)C(=O)C1CCN(c2ccc(Cl)c(-c3nc4ccccc4[nH]3)c2)CC1] | H | 454.00738 | 454 | 1.35 | method a |
| 35 | 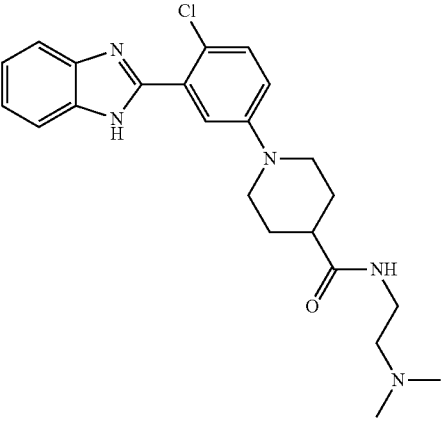 [SMILES: CN(C)CCNC(=O)C1CCN(c2ccc(Cl)c(-c3nc4ccccc4[nH]3)c2)CC1] | H | 425.95422 | 426 | 1.22 | method a |

TABLE-continued
| Example | Structure | Synthesis method | Calculated mass | Found mass | LCMS r.t. | LCMS method |
|---|---|---|---|---|---|---|
| 36 | 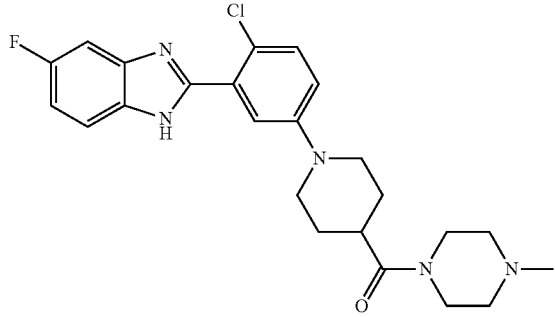 | H | 455.95538 | 456 | 1.53 | method a |
| 37 | 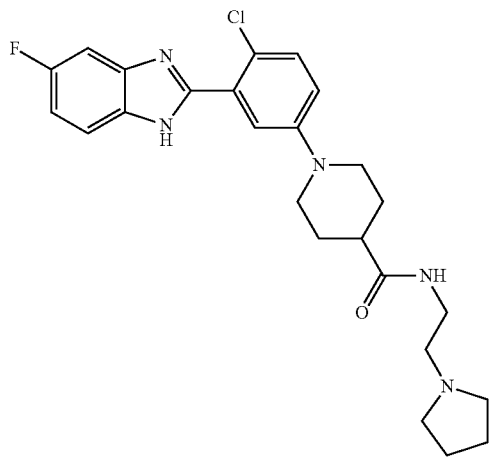 [SMILES: O=C(NCCN1CCCC1)C1CCN(c2ccc(Cl)c(-c3nc4cc(F)ccc4[nH]3)c2)CC1] | H | 469.98196 | 470 | 1.62 | method a |
| 38 | 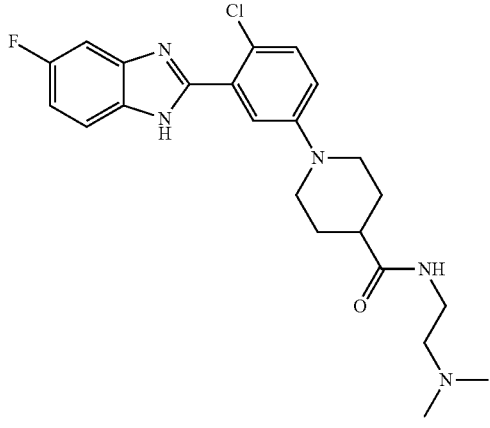 [SMILES: CN(C)CCNC(=O)C1CCN(c2ccc(Cl)c(-c3nc4cc(F)ccc4[nH]3)c2)CC1] | H | 443.94468 | 444 | 1.53 | method a |
| 39 | 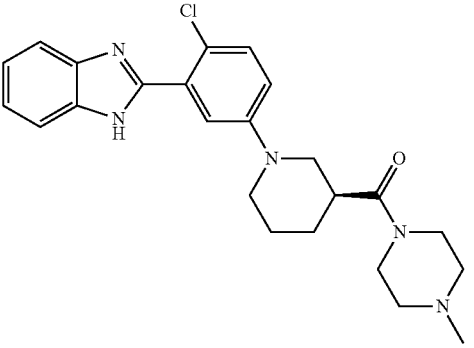 [SMILES: CN1CCN(C(=O)[C@H]2CCCN(c3ccc(Cl)c(-c4nc5ccccc5[nH]4)c3)C2)CC1] | B | 437.96492 | 438 | 0.2 | method a |

TABLE-continued

| Example | Structure | Synthesis method | Calculated mass | Found mass | LCMS r.t. | LCMS method |
|---|---|---|---|---|---|---|
| 40 | 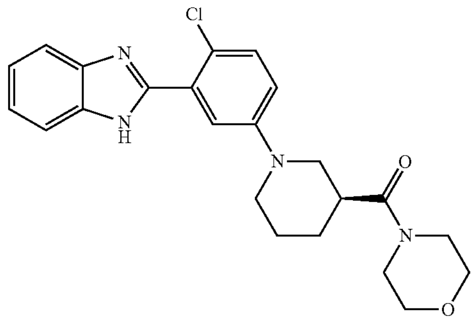 [SMILES: O=C([C@H]1CCCN(c2ccc(Cl)c(-c3nc4ccccc4[nH]3)c2)C1)N1CCOCC1] | B | 424.92306 | 425 | 2.02 | method a |
| 41 | 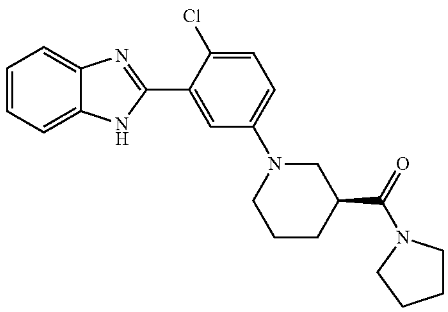 [SMILES: O=C([C@H]1CCCN(c2ccc(Cl)c(-c3nc4ccccc4[nH]3)c2)C1)N1CCCC1] | B | 408.92366 | 409 | 2.25 | method a |
| 42 | 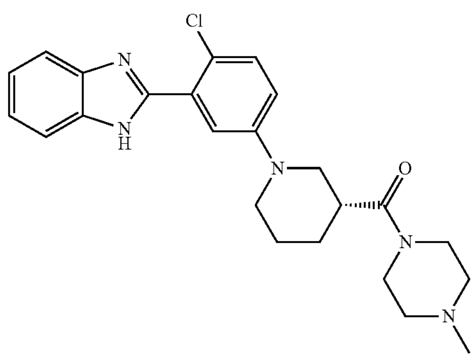 [SMILES: CN1CCN(C(=O)[C@@H]2CCCN(c3ccc(Cl)c(-c4nc5ccccc5[nH]4)c3)C2)CC1] | B | 437.96492 | 438 | 1.23 | method a |
| 43 | 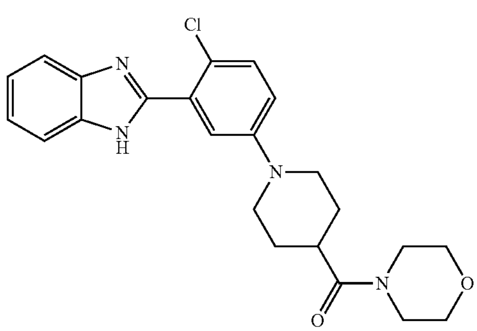 [SMILES: O=C(C1CCN(c2ccc(Cl)c(-c3nc4ccccc4[nH]3)c2)CC1)N1CCOCC1] | H | 424.92306 | 425 | 1.92 | method a |

TABLE-continued

| Example | Structure | Synthesis method | Calculated mass | Found mass | LCMS r.t. | LCMS method |
|---|---|---|---|---|---|---|
| 44 | 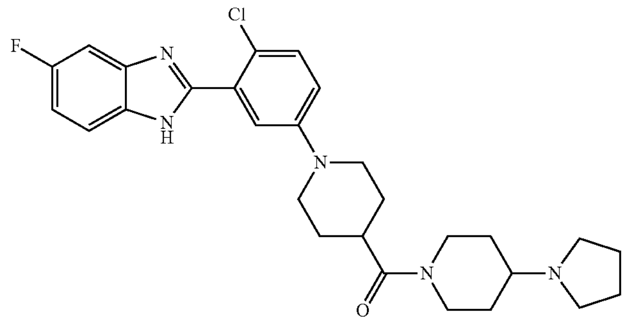 [SMILES: O=C(C1CCN(c2ccc(Cl)c(-c3nc4cc(F)ccc4[nH]3)c2)CC1)N1CCC(N2CCCC2)CC1] | H | 510.04582 | 510 | 1.7 | method a |
| 45 | 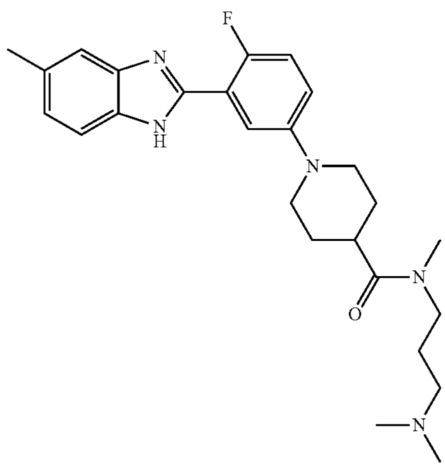 | I | 451.57966 | 452 | 1.43 | method a |
| 46 | 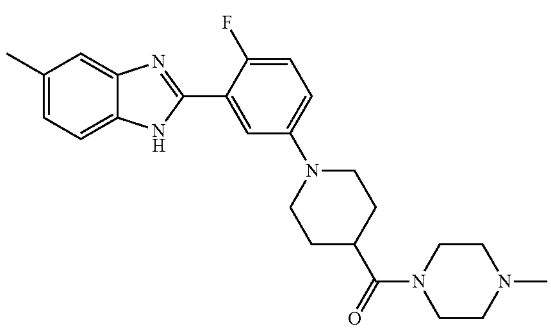 | I | 435.5372 | 436 | 1.15 | method a |
| 47 | 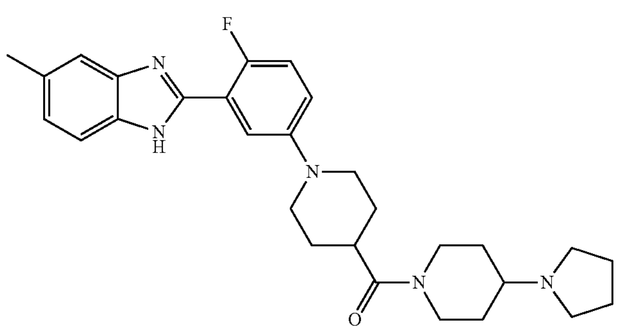 [SMILES: Cc1ccc2[nH]c(-c3cc(N4CCC(C(=O)N5CCC(N6CCCC6)CC5)CC4)ccc3F)nc2c1] | I | 489.62764 | 490 | 1.4 | method a |

TABLE-continued

| Example | Structure | Synthesis method | Calculated mass | Found mass | LCMS r.t. | LCMS method |
|---|---|---|---|---|---|---|
| 48 | 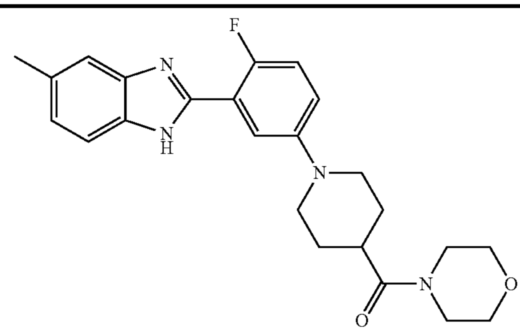 | I | 422.49534 | 423 | 1.15 | method a |
| 49 | 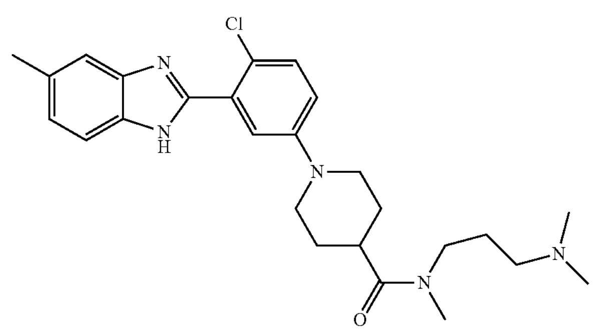 | B | 468.03396 | 469 | 1.52 | method a |
| 50 | 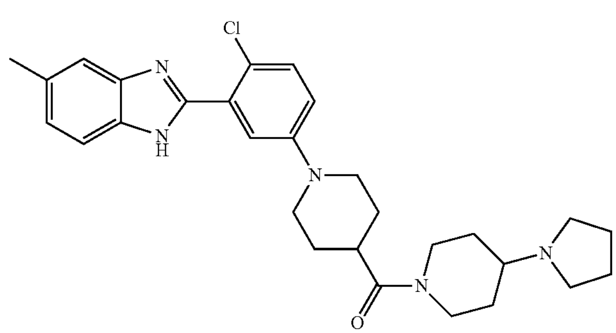 [SMILES: Cc1ccc2[nH]c(-c3cc(N4CCC(C(=O)N5CCC(N6CCCC6)CC5)CC4)ccc3Cl)nc2c1] | B | 506.08194 | 507 | 1.52 | method a |
| 51 | 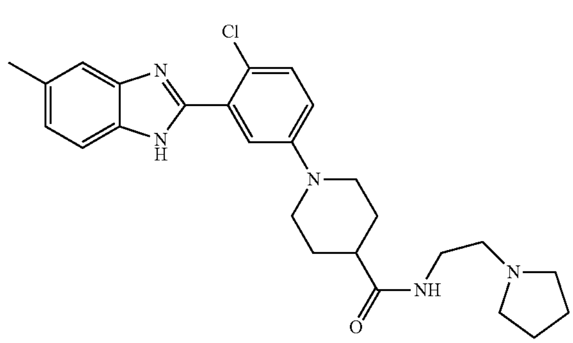 [SMILES: Cc1ccc2[nH]c(-c3cc(N4CCC(C(=O)NCCN5CCCC5)CC4)ccc3Cl)nc2c1] | B | 466.01808 | 467 | 1.5 | method a |

TABLE-continued
| Example | Structure | Synthesis method | Calculated mass | Found mass | LCMS r.t. | LCMS method |
|---|---|---|---|---|---|---|
| 52 | 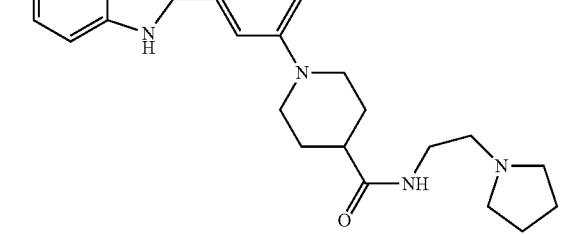 | B | 482.01748 | 482 | 1.42 | method a |
| 53 | 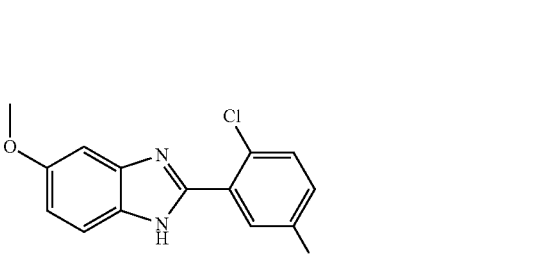 | B | 454.94904 | 455 | 2.03 | method a |
| 54 | 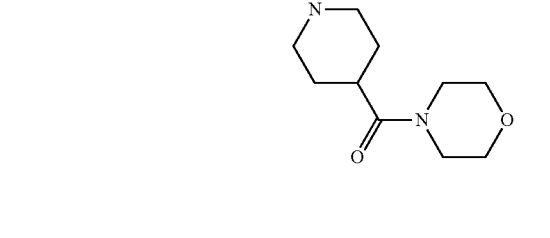 | F | 422.95024 | 423 | 2.05 | method a |
| 55 | 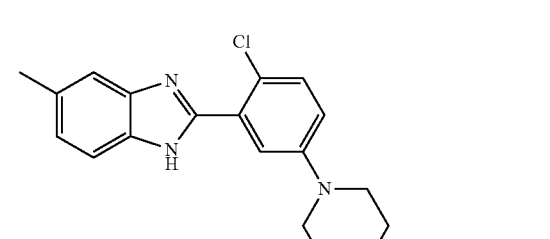 | B | 454.00738 | 454 | 0.18 | method a |

TABLE-continued

| Example | Structure | Synthesis method | Calculated mass | Found mass | LCMS r.t. | LCMS method |
|---|---|---|---|---|---|---|
| 56 | 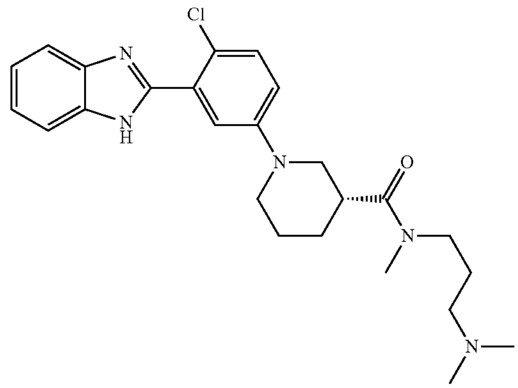 [SMILES: CN(C)CCCN(C)C(=O)[C@@H]1CCCN(c2ccc(Cl)c(-c3nc4ccccc4[nH]3)c2)C1] | B | 454.00738 | 454 | 0.2 | method a |
| 57 | 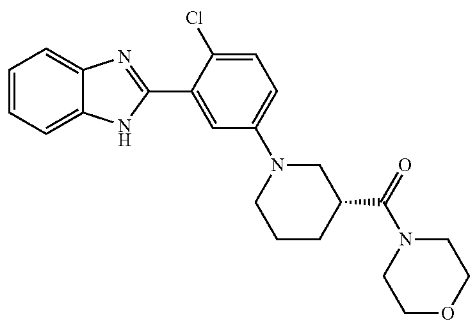 [SMILES: O=C([C@@H]1CCCN(c2ccc(Cl)c(-c3nc4ccccc4[nH]3)c2)C1)N1CCOCC1] | B | 424.92306 | 425 | 2.3 | method a |
| 58 | 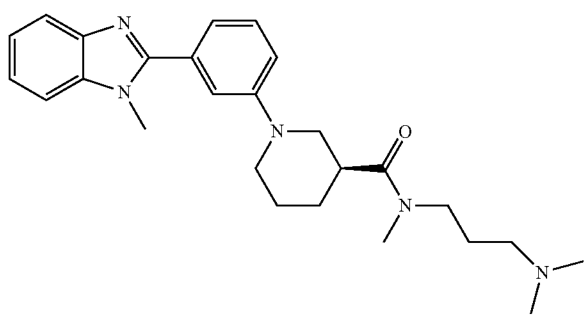 [SMILES: CN(C)CCCN(C)C(=O)[C@H]1CCCN(c2cccc(-c3nc4ccccc4n3C)c2)C1] | A | 433.5892 | 434 | | method a |
| 59 | 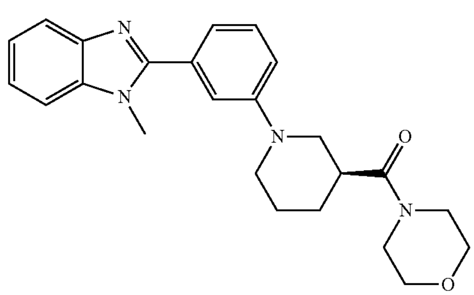 [SMILES: Cn1c(-c2cccc(N3CCC[C@H](C(=O)N4CCOCC4)C3)c2)nc2ccccc21] | A | 404.50488 | 405 | 1.68 | method a |

TABLE-continued

| Example | Structure | Synthesis method | Calculated mass | Found mass | LCMS r.t. | LCMS method |
|---|---|---|---|---|---|---|
| 60 | 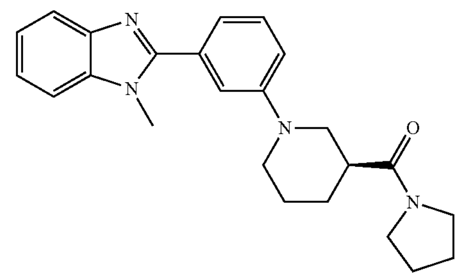 [SMILES: Cn1c(-c2cccc(N3CCC[C@H](C(=O)N4CCCC4)C3)c2)nc2ccccc21] | A | 388.50548 | 389 | 1.93 | method a |
| 61 | 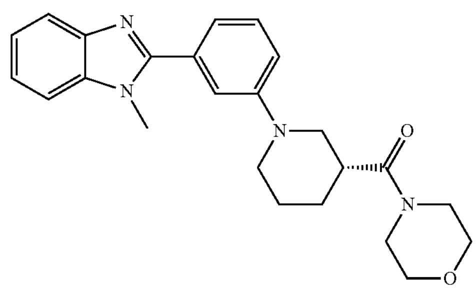 [SMILES: Cn1c(-c2cccc(N3CCC[C@@H](C(=O)N4CCOCC4)C3)c2)nc2ccccc21] | A | 404.50488 | 405 | 1.7 | method a |
| 62 | 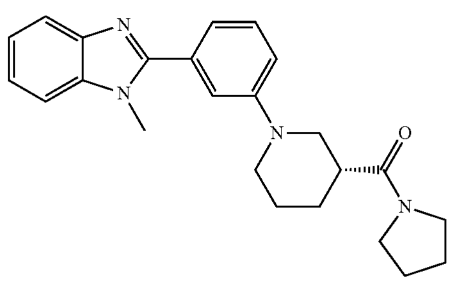 [SMILES: Cn1c(-c2cccc(N3CCC[C@@H](C(=O)N4CCCC4)C3)c2)nc2ccccc21] | A | 388.50548 | 389 | 1.9 | method a |
| 63 | 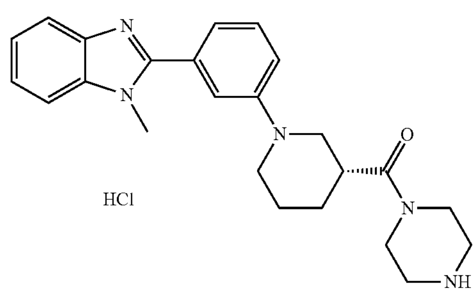 [SMILES: Cn1c(-c2cccc(N3CCC[C@@H](C(=O)N4CCNCC4)C3)c2)nc2ccccc21 ; Cl] | A | 403.52016 | 404 | 0.2 | method a |
| 64 | 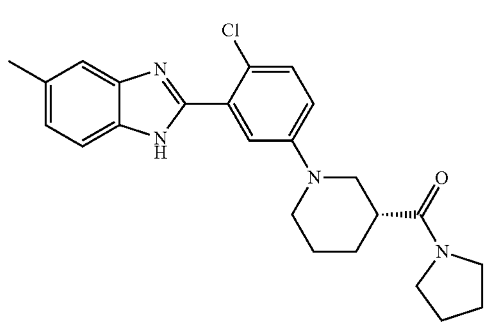 [SMILES: Cc1ccc2[nH]c(-c3cc(N4CCC[C@@H](C(=O)N5CCCC5)C4)ccc3Cl)nc2c1] | E | 422.95024 | 423 | 2.38 | method a |

TABLE-continued
| Example | Structure | Synthesis method | Calculated mass | Found mass | LCMS r.t. | LCMS method |
|---|---|---|---|---|---|---|
| 65 | 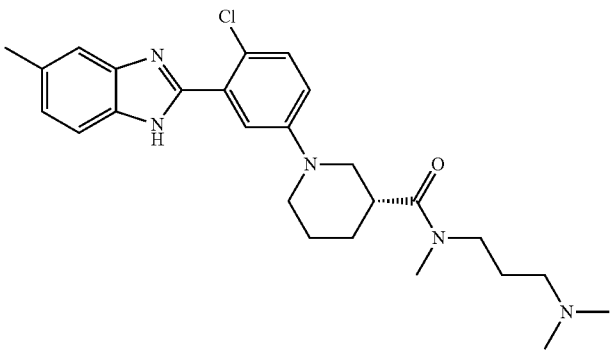 | E | 468.03396 | 468 | 1.48 | method a |
| 66 | 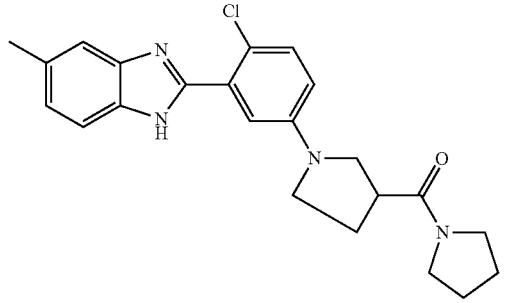 [SMILES: Cc1ccc2[nH]c(-c3cc(N4CCC(C(=O)N5CCCC5)C4)ccc3Cl)nc2c1] | E | 408.92366 | 409 | 2.33 | method a |
| 67 | 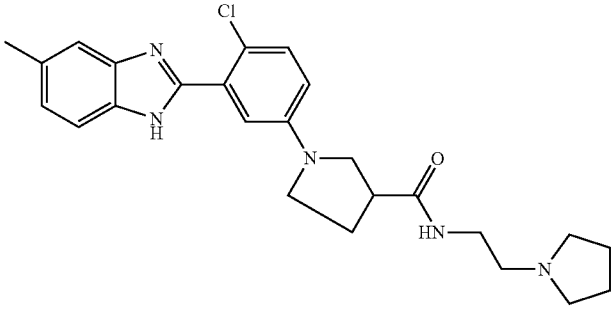 [SMILES: Cc1ccc2[nH]c(-c3cc(N4CCC(C(=O)NCCN5CCCC5)C4)ccc3Cl)nc2c1] | E | 451.9915 | 452 | 1.42 | method a |
| 68 | 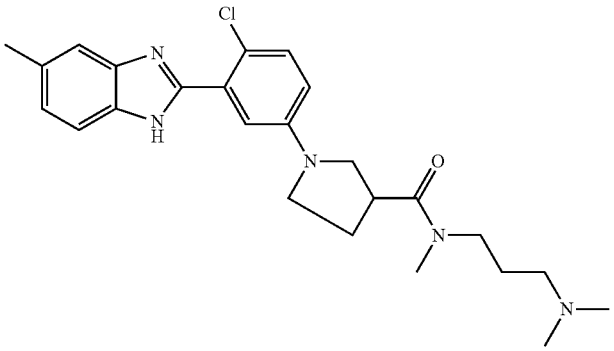 | E | 454.00738 | 454 | 1.37 | method a |

TABLE-continued

| Example | Structure | Synthesis method | Calculated mass | Found mass | LCMS r.t. | LCMS method |
|---|---|---|---|---|---|---|
| 69 | 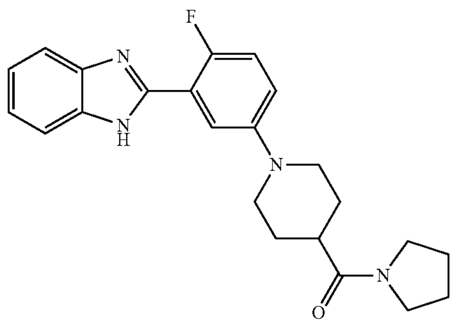 [SMILES: O=C(C1CCN(c2ccc(F)c(-c3nc4ccccc4[nH]3)c2)CC1)N1CCCC1] | E | 392.46936 | 393 | 2.05 | method a |
| 70 | 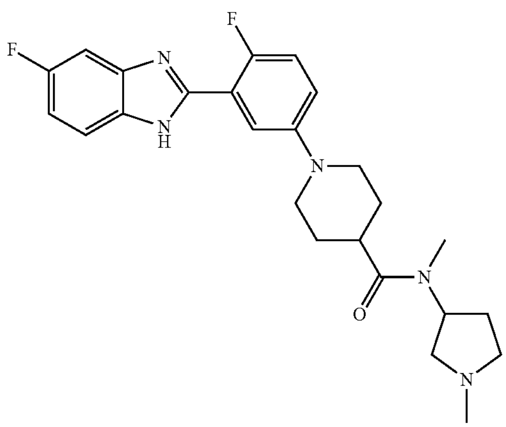 [SMILES: CN1CCC(N(C)C(=O)C2CCN(c3ccc(F)c(-c4nc5cc(F)ccc5[nH]4)c3)CC2)C1] | I | 453.52767 | 454 | 1.55 | method a |
| 71 | 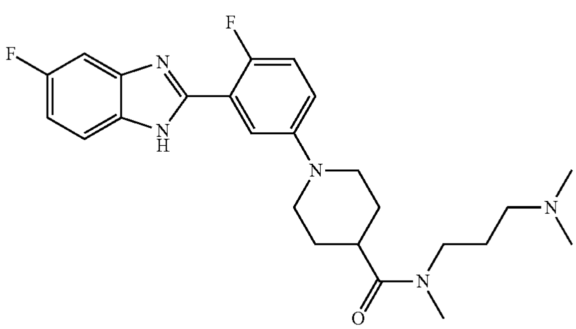 [SMILES: CN(C)CCCN(C)C(=O)C1CCN(c2ccc(F)c(-c3nc4cc(F)ccc4[nH]3)c2)CC1] | I | 455.54355 | 456 | 1.57 | method a |
| 72 | 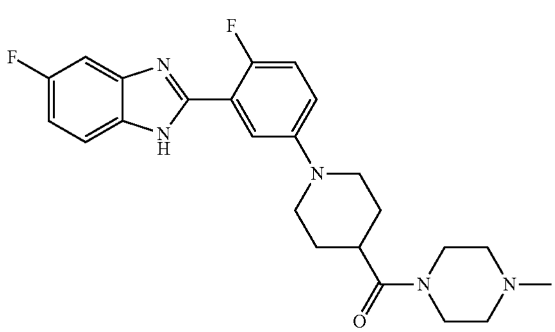 [SMILES: CN1CCN(C(=O)C2CCN(c3ccc(F)c(-c4nc5cc(F)ccc5[nH]4)c3)CC2)CC1] | D | 439.50109 | 440 | 1.28 | method a |

TABLE-continued

| Example | Structure | Synthesis method | Calculated mass | Found mass | LCMS r.t. | LCMS method |
|---|---|---|---|---|---|---|
| 73 | 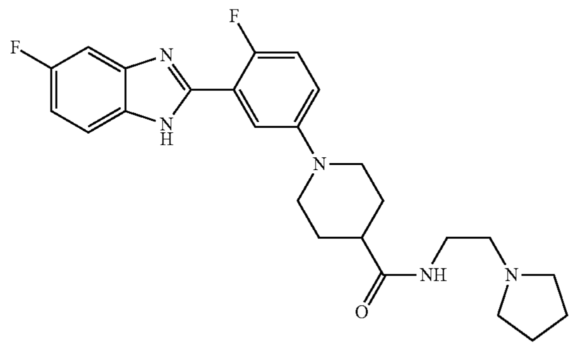 [SMILES: O=C(NCCN1CCCC1)C1CCN(c2ccc(F)c(-c3nc4cc(F)ccc4[nH]3)c2)CC1] | D | 453.52767 | 454 | 1.47 | method a |
| 74 | 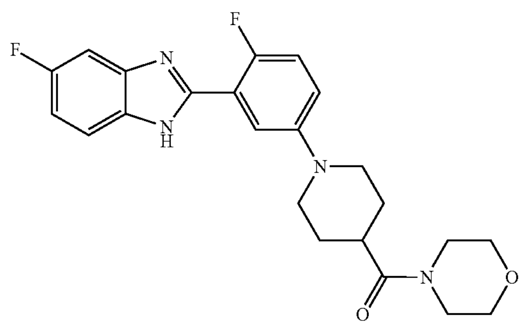 [SMILES: O=C(C1CCN(c2ccc(F)c(-c3nc4cc(F)ccc4[nH]3)c2)CC1)N1CCOCC1] | D | 426.45923 | 427 | 2.2 | method a |
| 75 | 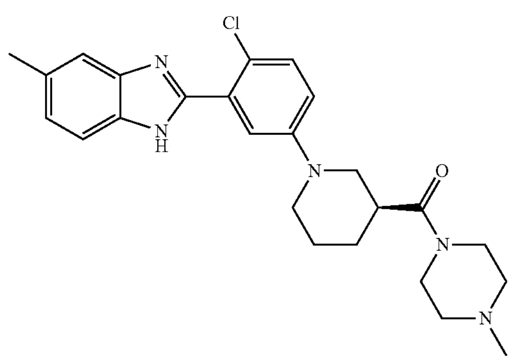 | E | 451.9915 | 452 | 1.45 | method a |
| 76 | 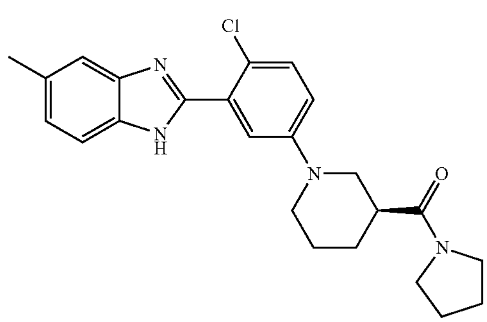 [SMILES: Cc1ccc2[nH]c(-c3cc(N4CCC[C@H](C(=O)N5CCCC5)C4)ccc3Cl)nc2c1] | E | 422.95024 | 423 | 2.37 | method a |

TABLE-continued
| Example | Structure | Synthesis method | Calculated mass | Found mass | LCMS r.t. | LCMS method |
|---|---|---|---|---|---|---|
| 77 | 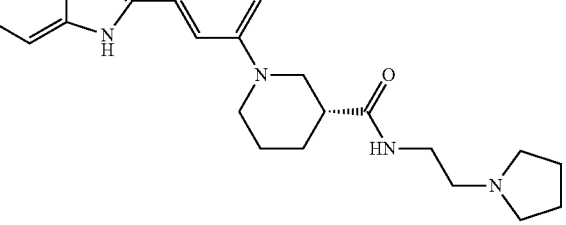 | E | 466.01808 | 466 | 1.52 | method a |
| 78 | 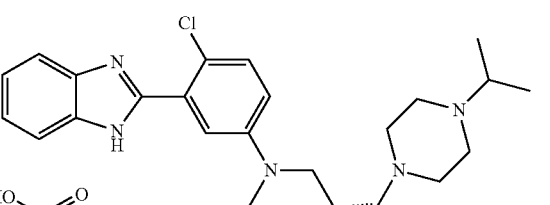 | D | 466.01808 | 466 | 1.23 | method a |
| 79 | 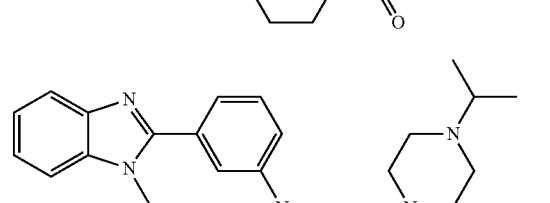 | D | 445.5999 | 446 | 0.97 | method a |
| 80 | 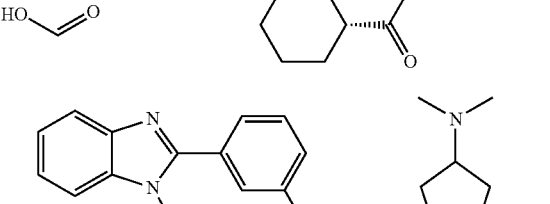 | D | 431.57332 | 432 | 0.65 | method a |
| 81 | 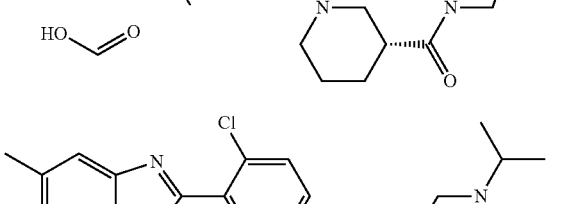 | D | 480.04466 | 480 | 1.48 | method a |
| 82 | 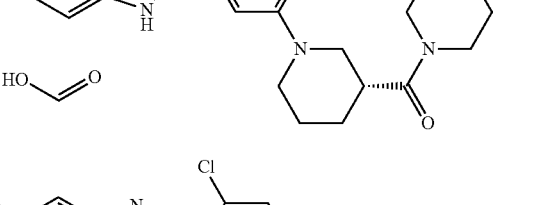 | D | 466.01808 | 466 | 1.37 | method a |

| Example | Structure | Synthesis method | Calculated mass | Found mass | LCMS r.t. | LCMS method |
|---|---|---|---|---|---|---|
| 83 | 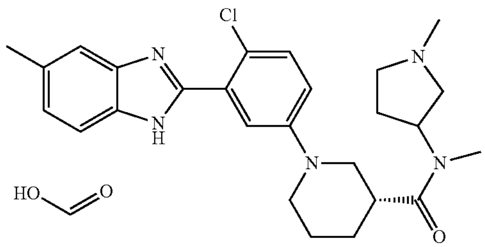 | D | 466.01808 | 466 | 1.43 | method a |
| 84 | 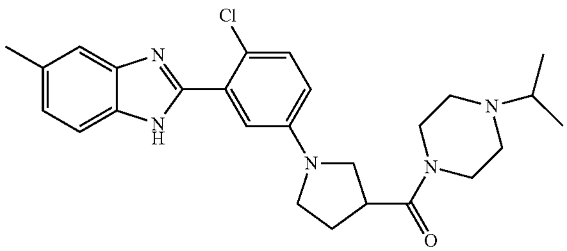 [SMILES: Cc1ccc2[nH]c(-c3cc(N4CCC(C(=O)N5CCN(C(C)C)CC5)C4)ccc3Cl)nc2c1] | D | 466.01808 | 466 | 1.5 | method a |
| 85 | 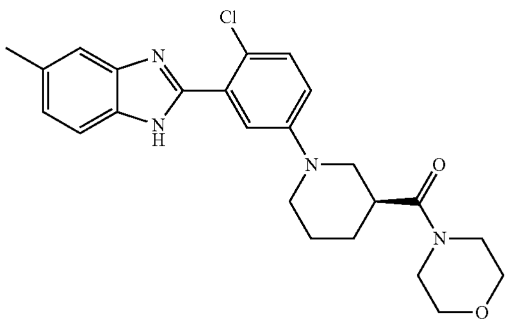 [SMILES: Cc1ccc2[nH]c(-c3cc(N4CCC[C@H](C(=O)N5CCOCC5)C4)ccc3Cl)nc2c1] | E | 438.94964 | 439 | 2.15 | method a |
| 86 | 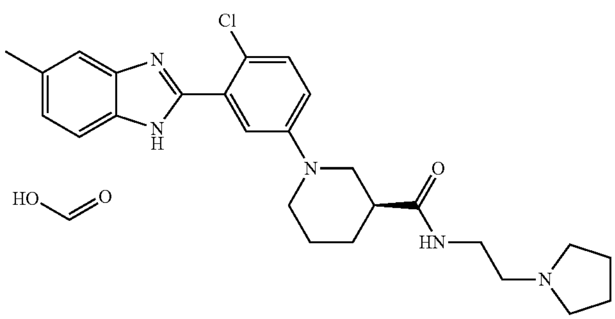 [SMILES: Cc1ccc2[nH]c(-c3cc(N4CCC[C@H](C(=O)NCCN5CCCC5)C4)ccc3Cl)nc2c1 ; O=CO] | E | 466.01808 | 466 | 1.42 | method a |
| 87 | 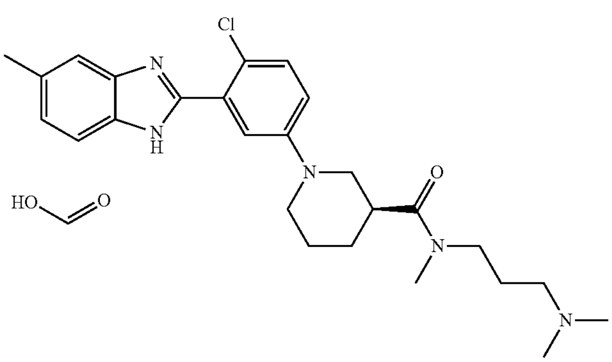 | E | 468.03396 | 468 | 1.42 | method a |

TABLE-continued
| Example | Structure | Synthesis method | Calculated mass | Found mass | LCMS r.t. | LCMS method |
|---|---|---|---|---|---|---|
| 88 | 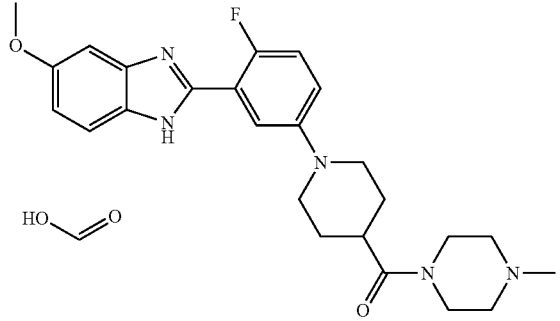 [SMILES: COc1ccc2[nH]c(-c3cc(N4CCC(C(=O)N5CCN(C)CC5)CC4)ccc3F)nc2c1 ; O=CO] | E | 451.5366 | 452 | 1.13 | method a |
| 89 | 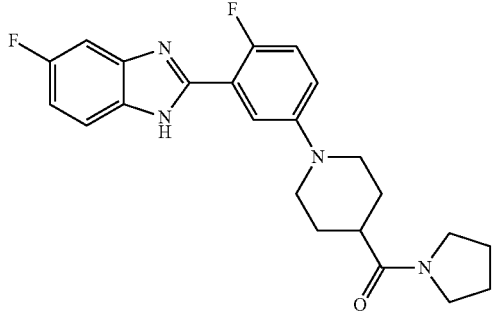 [SMILES: O=C(C1CCN(c2ccc(F)c(-c3nc4cc(F)ccc4[nH]3)c2)CC1)N1CCCC1] | D | 410.45983 | 411 | 2.48 | method a |
| 90 | 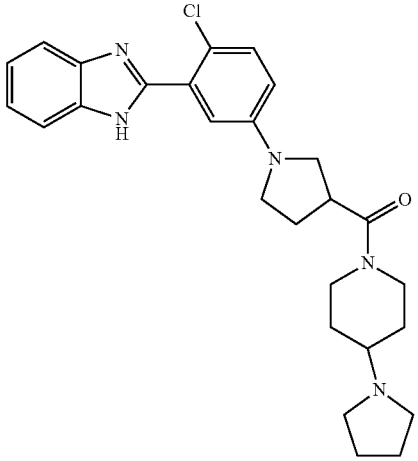 [SMILES: O=C(C1CCN(c2ccc(Cl)c(-c3nc4ccccc4[nH]3)c2)C1)N1CCC(N2CCCC2)CC1] | G | 478.02878 | 478 | 1.32 | method a |
| 91 | 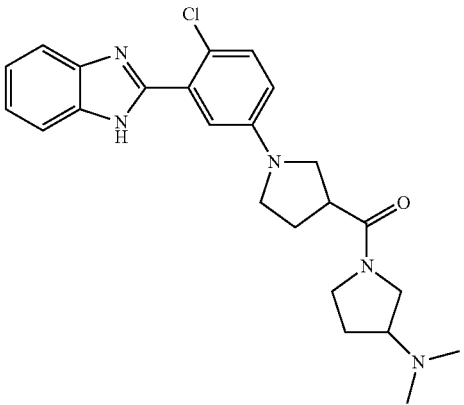 [SMILES: CN(C)C1CCN(C(=O)C2CCN(c3ccc(Cl)c(-c4nc5ccccc5[nH]4)c3)C2)C1] | G | 437.96492 | 438 | 1.23 | method a |

| Example | Structure | Synthesis method | Calculated mass | Found mass | LCMS r.t. | LCMS method |
|---|---|---|---|---|---|---|
| 92 | 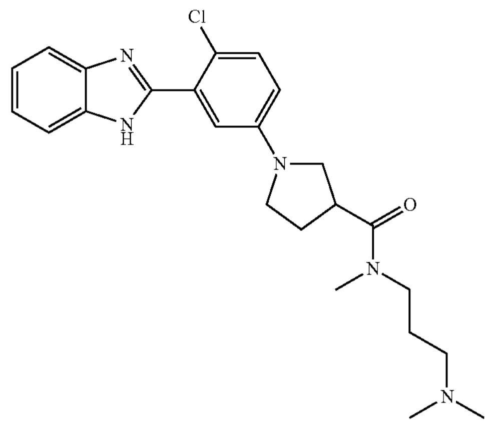 [SMILES: CN(C)CCCN(C)C(=O)C1CCN(c2ccc(Cl)c(-c3nc4ccccc4[nH]3)c2)C1] | G | 439.9808 | 440 | 1.27 | method a |
| 93 | 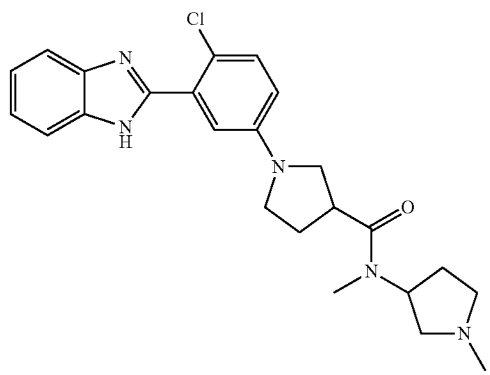 [SMILES: CN1CCC(N(C)C(=O)C2CCN(c3ccc(Cl)c(-c4nc5ccccc5[nH]4)c3)C2)C1] | G | 437.96492 | 438 | 1.27 | method a |
| 94 | 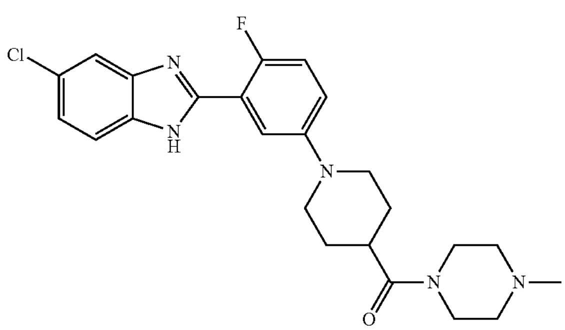 [SMILES: CN1CCN(C(=O)C2CCN(c3ccc(F)c(-c4nc5cc(Cl)ccc5[nH]4)c3)CC2)CC1] | J | 455.95538 | 455 | 1.68 | method b |
| 95 | 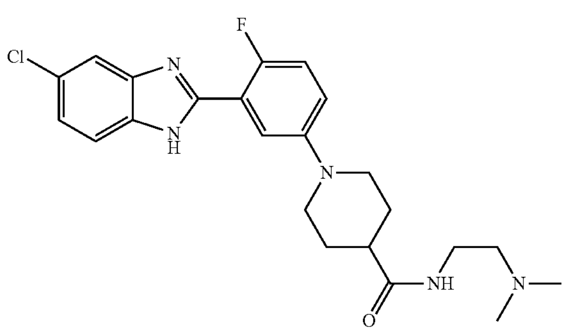 [SMILES: CN(C)CCNC(=O)C1CCN(c2ccc(F)c(-c3nc4cc(Cl)ccc4[nH]3)c2)CC1] | J | 443.94468 | 443 | 1.72 | method b |

| Example | Structure | Synthesis method | Calculated mass | Found mass | LCMS r.t. | LCMS method |
|---|---|---|---|---|---|---|
| 96 | 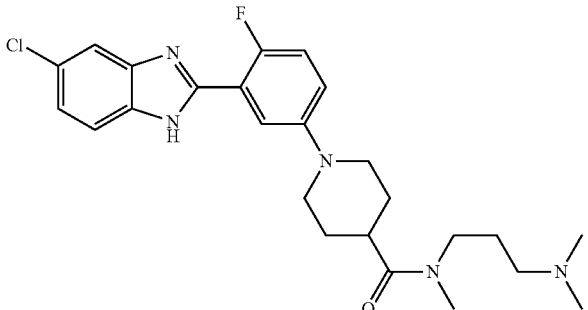 | J | 471.99784 | 472 | 1.78 | method b |
| 97 | 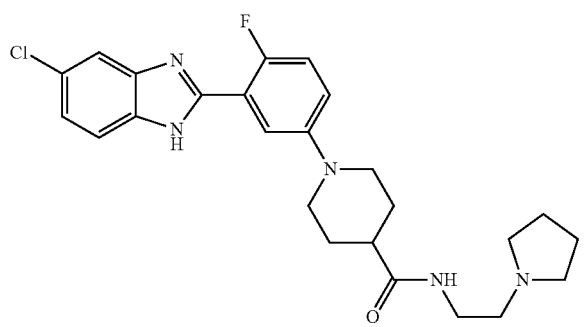 [SMILES: O=C(NCCN1CCCC1)C1CCN(c2ccc(F)c(-c3nc4cc(Cl)ccc4[nH]3)c2)CC1] | J | 469.98196 | 470 | 1.72 | method b |
| 98 | 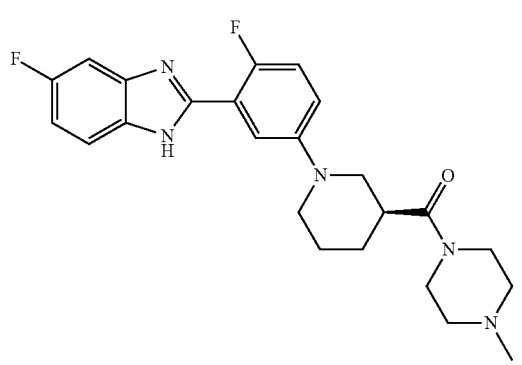 [SMILES: CN1CCN(C(=O)[C@H]2CCCN(c3ccc(F)c(-c4nc5cc(F)ccc5[nH]4)c3)C2)CC1] | J | 439.50109 | 440 | 1.48 | method b |
| 99 | 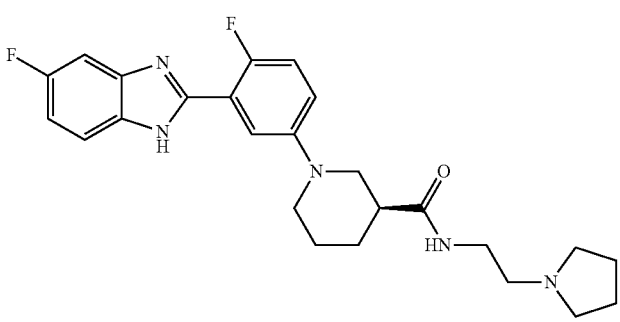 [SMILES: O=C(NCCN1CCCC1)[C@H]1CCCN(c2ccc(F)c(-c3nc4cc(F)ccc4[nH]3)c2)C1] | J | 453.52767 | 454 | 1.65 | method b |

TABLE-continued

| Example | Structure | Synthesis method | Calculated mass | Found mass | LCMS r.t. | LCMS method |
|---|---|---|---|---|---|---|
| 100 | 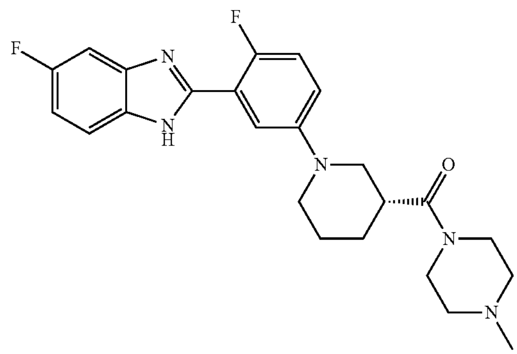 [SMILES: CN1CCN(C(=O)[C@@H]2CCCN(c3ccc(F)c(-c4nc5cc(F)ccc5[nH]4)c3)C2)CC1] | J | 439.50109 | 440 | 1.47 | method b |
| 101 | 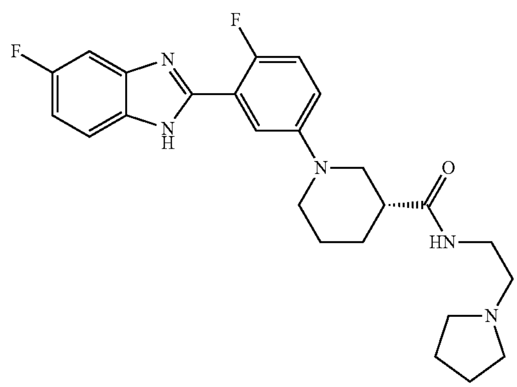 [SMILES: O=C(NCCN1CCCC1)[C@@H]1CCCN(c2ccc(F)c(-c3nc4cc(F)ccc4[nH]3)c2)C1] | J | 453.52767 | 454 | 2.93 | method b |
| 102 | 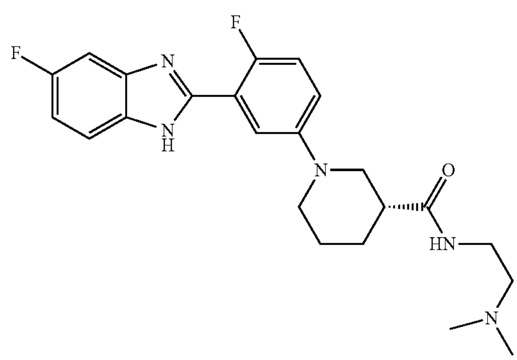 [SMILES: CN(C)CCNC(=O)[C@@H]1CCCN(c2ccc(F)c(-c3nc4cc(F)ccc4[nH]3)c2)C1] | J | 427.49039 | 428 | 1.55 | method b |
| 103 | 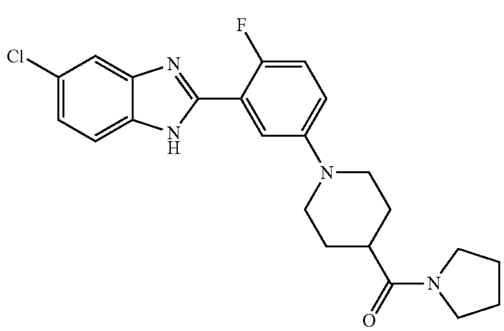 [SMILES: O=C(C1CCN(c2ccc(F)c(-c3nc4cc(Cl)ccc4[nH]3)c2)CC1)N1CCCC1] | J | 426.91412 | 427 | 2.87 | method b |

TABLE-continued

| Example | Structure | Synthesis method | Calculated mass | Found mass | LCMS r.t. | LCMS method |
|---|---|---|---|---|---|---|
| 104 | 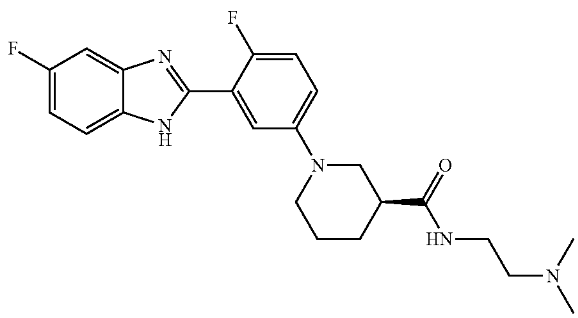 [SMILES: CN(C)CCNC(=O)[C@H]1CCCN(c2ccc(F)c(-c3nc4cc(F)ccc4[nH]3)c2)C1] | J | 427.49039 | 428 | 1.6 | method b |
| 105 | 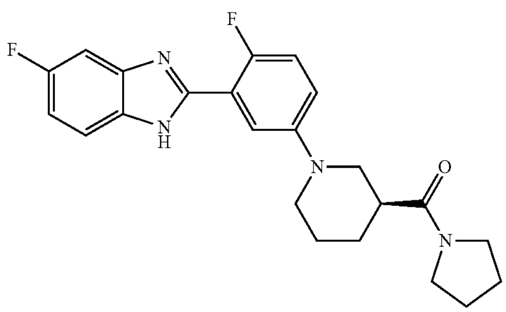 [SMILES: O=C([C@H]1CCCN(c2ccc(F)c(-c3nc4cc(F)ccc4[nH]3)c2)C1)N1CCCC1] | J | 410.45983 | 411 | 2.62 | method b |
| 106 | 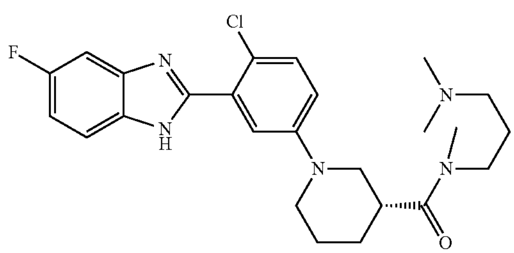 [SMILES: CN(C)CCCN(C)C(=O)[C@@H]1CCCN(c2ccc(Cl)c(-c3nc4cc(F)ccc4[nH]3)c2)C1] | K | 471.99784 | 472 | 2.93 | method b |
| 107 | 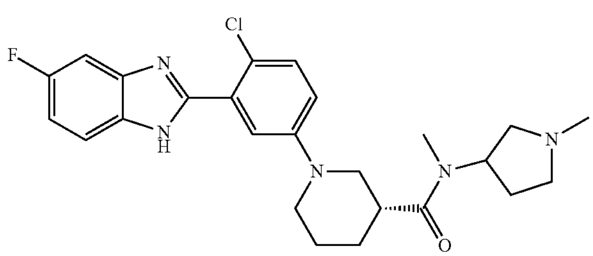 [SMILES: CN1CCC(N(C)C(=O)[C@@H]2CCCN(c3ccc(Cl)c(-c4nc5cc(F)ccc5[nH]4)c3)C2)C1] | K | 469.98196 | 470 | 2.92 | method b |
| 108 | 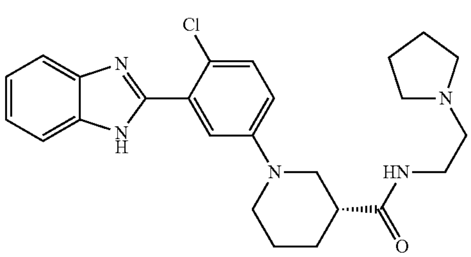 [SMILES: O=C(NCCN1CCCC1)[C@@H]1CCCN(c2ccc(Cl)c(-c3nc4ccccc4[nH]3)c2)C1] | K | 451.9915 | 452 | 2.27 | method b |

TABLE-continued
| Example | Structure | Synthesis method | Calculated mass | Found mass | LCMS r.t. | LCMS method |
|---|---|---|---|---|---|---|
| 109 | 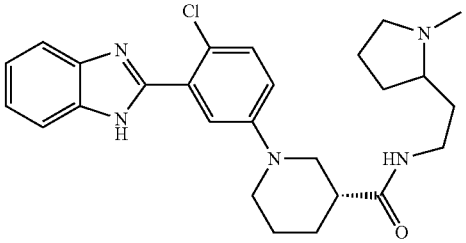 [SMILES: CN1CCCC1CCNC(=O)[C@@H]1CCCN(c2ccc(Cl)c(-c3nc4ccccc4[nH]3)c2)C1] | K | 466.01808 | 466 | 2.35 | method b |
| 110 | 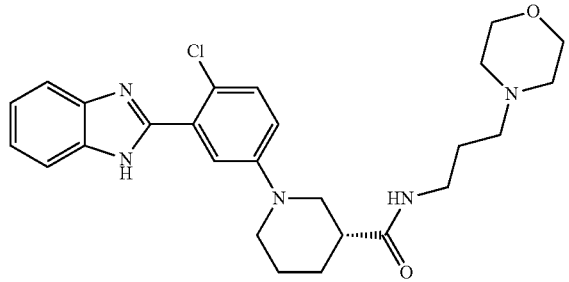 [SMILES: O=C(NCCCN1CCOCC1)[C@@H]1CCCN(c2ccc(Cl)c(-c3nc4ccccc4[nH]3)c2)C1] | K | 482.01748 | 482 | 2.18 | method b |
| 111 | 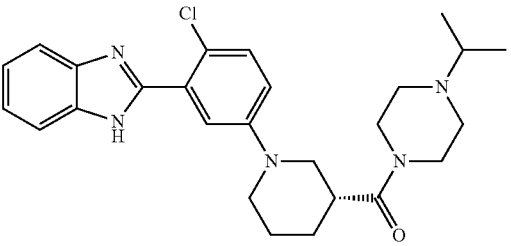 [SMILES: CC(C)N1CCN(C(=O)[C@@H]2CCCN(c3ccc(Cl)c(-c4nc5ccccc5[nH]4)c3)C2)CC1] | K | 466.01808 | 466 | 0.23 | method b |
| 112 | 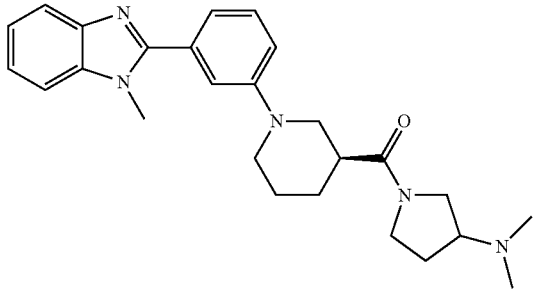 [SMILES: CN(C)C1CCN(C(=O)[C@H]2CCCN(c3cccc(-c4nc5ccccc5n4C)c3)C2)C1] | O | 431.57332 | 432 | 1.38 | method b |
| 113 | 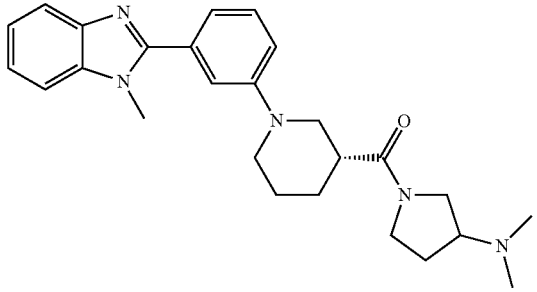 [SMILES: CN(C)C1CCN(C(=O)[C@@H]2CCCN(c3cccc(-c4nc5ccccc5n4C)c3)C2)C1] | O | 431.57332 | 432 | 1.43 | method b |

TABLE-continued

| Example | Structure | Synthesis method | Calculated mass | Found mass | LCMS r.t. | LCMS method |
|---|---|---|---|---|---|---|
| 114 | 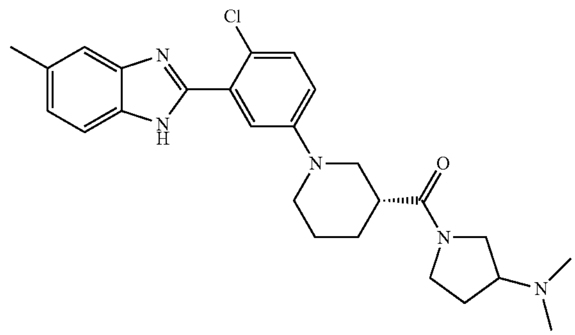 | O | 466.01808 | 466 | 2.28 | method b |
| 115 | 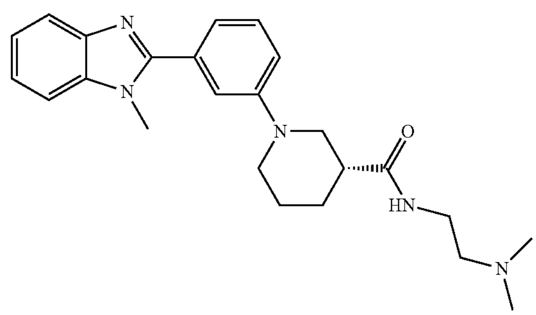 [SMILES: CN(C)CCNC(=O)[C@@H]1CCCN(c2cccc(-c3nc4ccccc4n3C)c2)C1] | O | 405.53604 | 406 | 1.48 | method b |
| 116 | 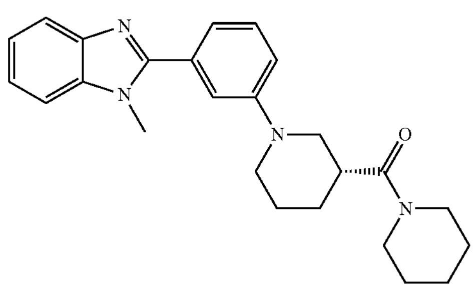 [SMILES: Cn1c(-c2cccc(N3CCC[C@@H](C(=O)N4CCCCC4)C3)c2)nc2ccccc21] | O | 402.53206 | 403 | 4.05 | method b |
| 117 | 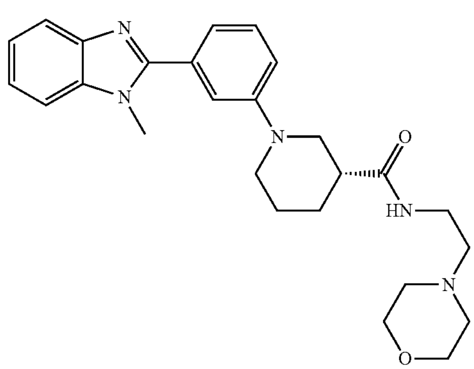 [SMILES: Cn1c(-c2cccc(N3CCC[C@@H](C(=O)NCCN4CCOCC4)C3)c2)nc2ccccc21] | O | 447.57272 | 448 | 1.63 | method b |

TABLE-continued
| Example | Structure | Synthesis method | Calculated mass | Found mass | LCMS r.t. | LCMS method |
|---|---|---|---|---|---|---|
| 118 | 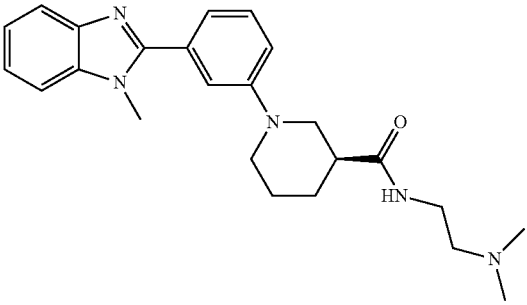 [SMILES: CN(C)CCNC(=O)[C@H]1CCCN(c2cccc(-c3nc4ccccc4n3C)c2)C1] | O | 405.53604 | 406 | 1.33 | method b |
| 119 | 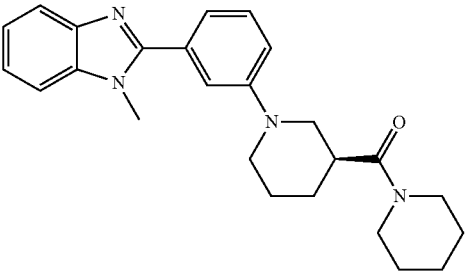 [SMILES: Cn1c(-c2cccc(N3CCC[C@H](C(=O)N4CCCCC4)C3)c2)nc2ccccc21] | O | 402.53206 | 402 | 4.05 | method b |
| 120 | 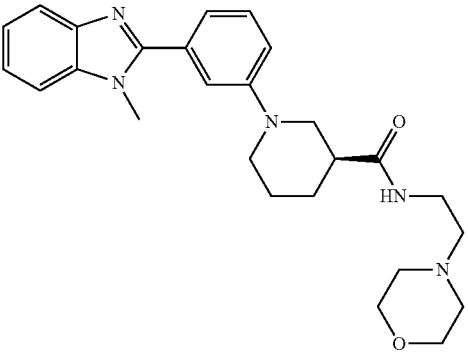 | O | 447.57272 | 448 | 1.58 | method b |
| 121 | 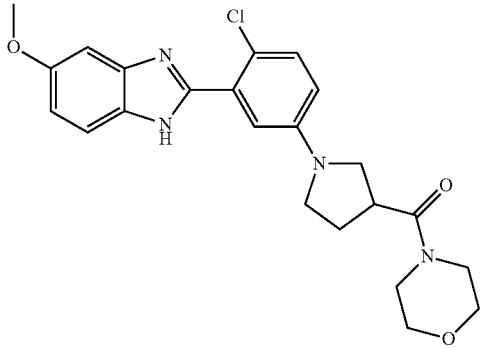 [SMILES: COc1ccc2[nH]c(-c3cc(N4CCC(C(=O)N5CCOCC5)C4)ccc3Cl)nc2c1] | O | 440.92246 | 441 | 3.83 | method b |
| 122 | 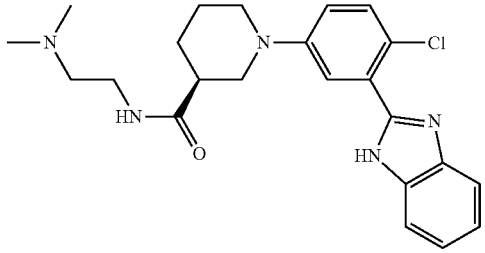 [SMILES: CN(C)CCNC(=O)[C@H]1CCCN(c2ccc(Cl)c(-c3nc4ccccc4[nH]3)c2)C1] | O | 425.95422 | 426 | 2.05 | method b |

TABLE-continued

| Example | Structure | Synthesis method | Calculated mass | Found mass | LCMS r.t. | LCMS method |
|---|---|---|---|---|---|---|
| 123 | 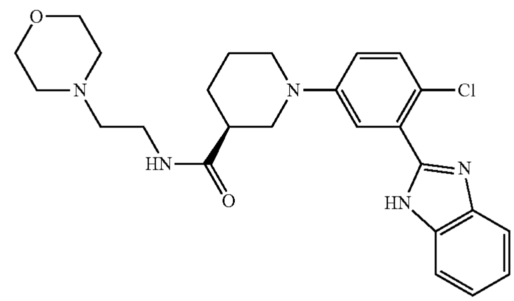 [SMILES: O=C(NCCN1CCOCC1)[C@H]1CCCN(c2ccc(Cl)c(-c3nc4ccccc4[nH]3)c2)C1] | O | 467.9909 | 468 | 2.23 | method b |
| 124 | 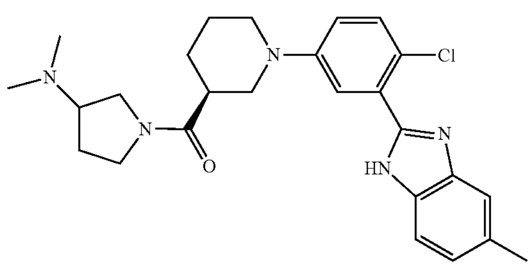 | O | 466.01808 | 466 | 2.32 | method b |
| 125 | 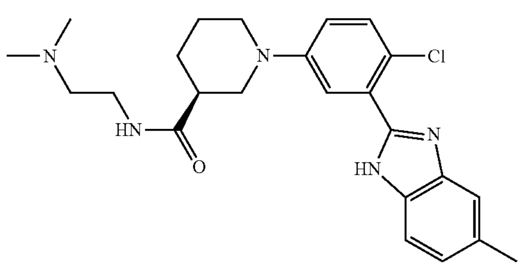 | O | 439.9808 | 440 | 2.35 | method b |
| 126 | 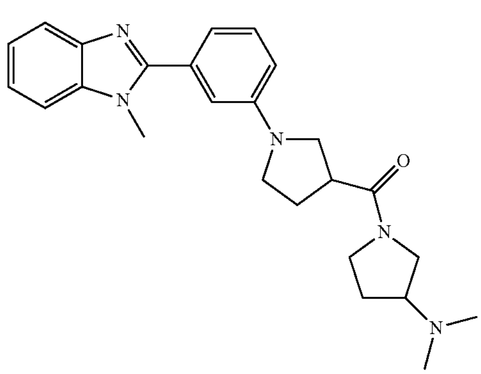 [SMILES: CN(C)C1CCN(C(=O)C2CCN(c3cccc(-c4nc5ccccc5n4C)c3)C2)C1] | O | 417.54674 | 418 | 1.63 | method b |

TABLE-continued

| Example | Structure | Synthesis method | Calculated mass | Found mass | LCMS r.t. | LCMS method |
|---|---|---|---|---|---|---|
| 127 | 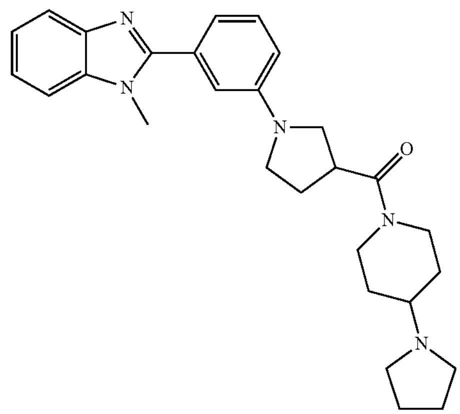 [SMILES: Cn1c(-c2cccc(N3CCC(C(=O)N4CCC(N5CCCC5)CC4)C3)c2)nc2ccccc21] | O | 457.6106 | 458 | 1.85 | method b |
| 128 | 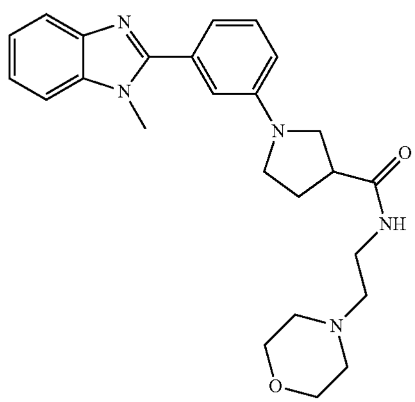 [SMILES: Cn1c(-c2cccc(N3CCC(C(=O)NCCN4CCOCC4)C3)c2)nc2ccccc21] | O | 433.54614 | 434 | 1.73 | method b |
| 129 | 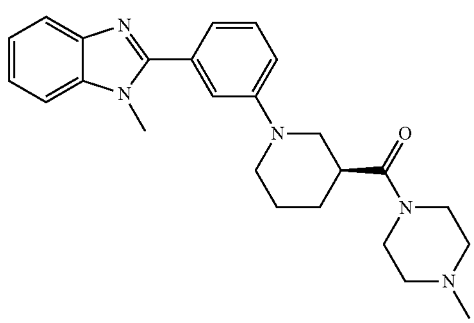 [SMILES: CN1CCN(C(=O)[C@H]2CCCN(c3cccc(-c4nc5ccccc5n4C)c3)C2)CC1] | O | 417.54674 | 418 | 1.62 | method b |
| 130 | 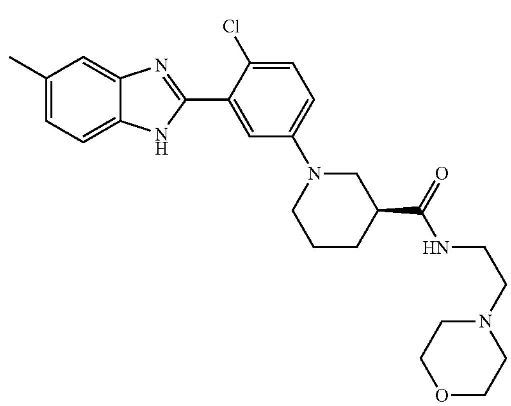 [SMILES: Cc1ccc2[nH]c(-c3cc(N4CCC[C@H](C(=O)NCCN5CCOCC5)C4)ccc3Cl)nc2c1] | O | 482.01748 | 482 | 2.43 | method b |

TABLE-continued

| Example | Structure | Synthesis method | Calculated mass | Found mass | LCMS r.t. | LCMS method |
|---|---|---|---|---|---|---|
| 131 | 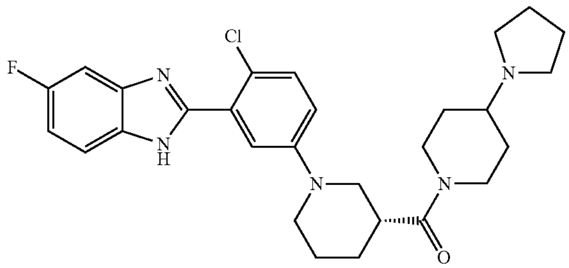 [SMILES: O=C([C@@H]1CCCN(c2ccc(Cl)c(-c3nc4cc(F)ccc4[nH]3)c2)C1)N1CCC(N2CCCC2)CC1] | K | 510.04582 | 510 | 3.12 | method b |
| 132 | 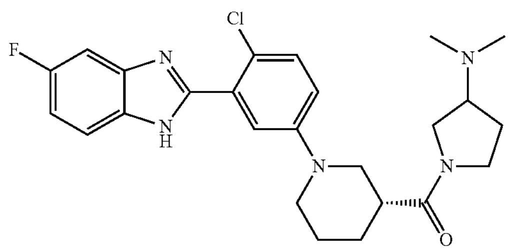 [SMILES: CN(C)C1CCN(C(=O)[C@@H]2CCCN(c3ccc(Cl)c(-c4nc5cc(F)ccc5[nH]4)c3)C2)C1] | K | 469.98196 | 470 | 2.83 | method b |
| 133 | 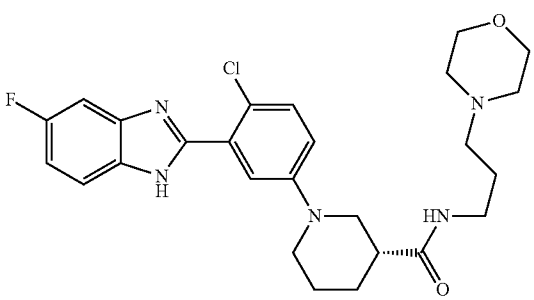 [SMILES: O=C(NCCCN1CCOCC1)[C@@H]1CCCN(c2ccc(Cl)c(-c3nc4cc(F)ccc4[nH]3)c2)C1] | K | 500.00794 | 500 | 3.07 | method b |
| 134 | 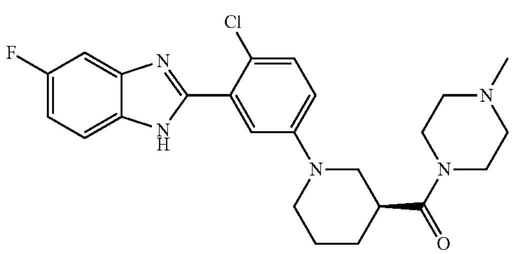 [SMILES: CN1CCN(C(=O)[C@H]2CCCN(c3ccc(Cl)c(-c4nc5cc(F)ccc5[nH]4)c3)C2)CC1] | K | 455.95538 | 456 | 2.75 | method b |
| 135 | 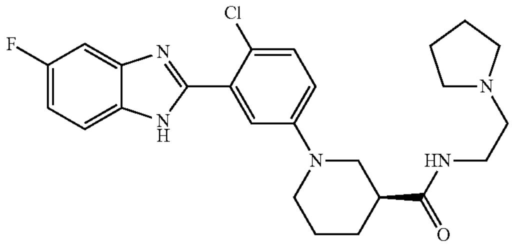 [SMILES: O=C(NCCN1CCCC1)[C@H]1CCCN(c2ccc(Cl)c(-c3nc4cc(F)ccc4[nH]3)c2)C1] | K | 469.98196 | 470 | 3.08 | method b |

TABLE-continued

| Example | Structure | Synthesis method | Calculated mass | Found mass | LCMS r.t. | LCMS method |
|---|---|---|---|---|---|---|
| 136 | 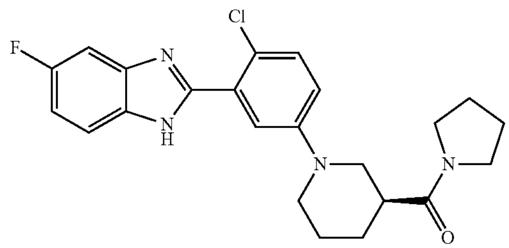 [SMILES: O=C([C@H]1CCCN(c2ccc(Cl)c(-c3nc4cc(F)ccc4[nH]3)c2)C1)N1CCCC1] | K | 426.91412 | 427 | 5.5 | method b |
| 137 | 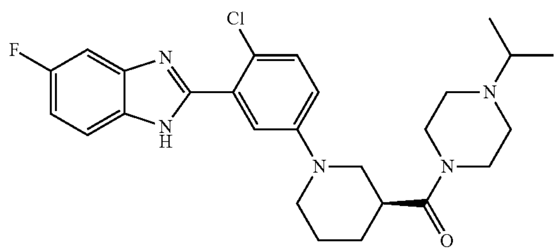 [SMILES: CC(C)N1CCN(C(=O)[C@H]2CCCN(c3ccc(Cl)c(-c4nc5cc(F)ccc5[nH]4)c3)C2)CC1] | K | 484.00854 | 484 | 3 | method b |
| 138 | 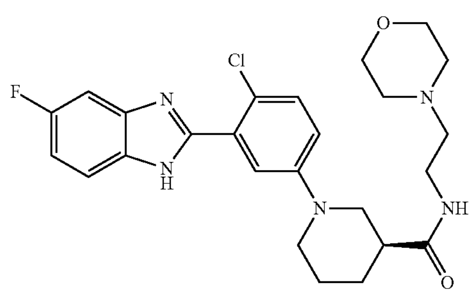 [SMILES: O=C(NCCN1CCOCC1)[C@H]1CCCN(c2ccc(Cl)c(-c3nc4cc(F)ccc4[nH]3)c2)C1] | K | 485.98136 | 486 | 2.92 | method b |
| 139 | 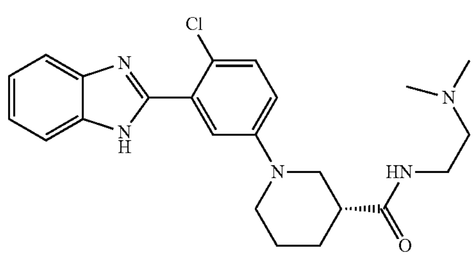 [SMILES: CN(C)CCNC(=O)[C@@H]1CCCN(c2ccc(Cl)c(-c3nc4ccccc4[nH]3)c2)C1] | K | 425.95422 | 426 | 2.1 | method b |
| 140 | 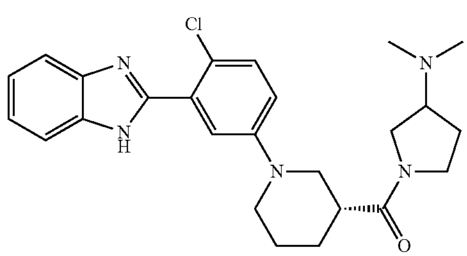 [SMILES: CN(C)C1CCN(C(=O)[C@@H]2CCCN(c3ccc(Cl)c(-c4nc5ccccc5[nH]4)c3)C2)C1] | K | 451.9915 | 452 | 0.27 | method b |
| 141 | 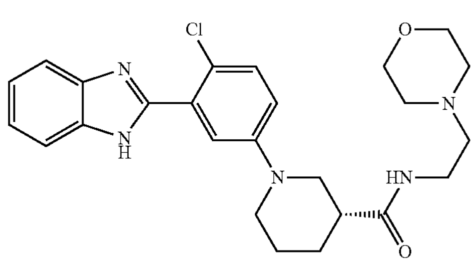 [SMILES: O=C(NCCN1CCOCC1)[C@@H]1CCCN(c2ccc(Cl)c(-c3nc4ccccc4[nH]3)c2)C1] | K | 467.9909 | 468 | 1.88 | method b |

TABLE-continued

| Example | Structure | Synthesis method | Calculated mass | Found mass | LCMS r.t. | LCMS method |
|---|---|---|---|---|---|---|
| 142 | 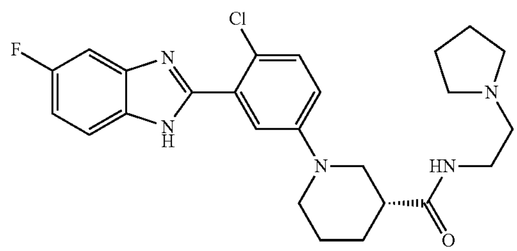 [SMILES: O=C(NCCN1CCCC1)[C@@H]1CCCN(c2ccc(Cl)c(-c3nc4cc(F)ccc4[nH]3)c2)C1] | K | 469.98196 | 470 | 3.1 | method b |
| 143 | 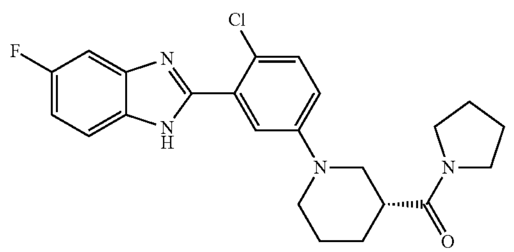 [SMILES: O=C([C@@H]1CCCN(c2ccc(Cl)c(-c3nc4cc(F)ccc4[nH]3)c2)C1)N1CCCC1] | K | 426.91412 | 427 | 5.55 | method b |
| 144 | 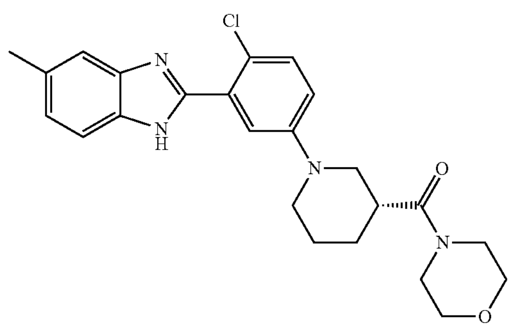 [SMILES: Cc1ccc2[nH]c(-c3cc(N4CCC[C@@H](C(=O)N5CCOCC5)C4)ccc3Cl)nc2c1] | E | 438.94964 | 439 | 4.17 | method b |
| 145 | 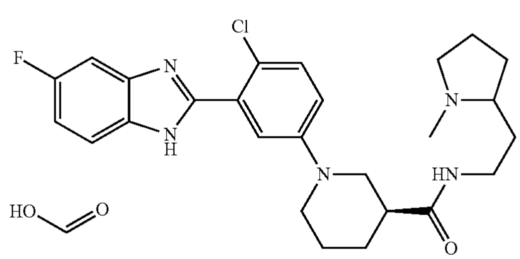 [SMILES: CN1CCCC1CCNC(=O)[C@H]1CCCN(c2ccc(Cl)c(-c3nc4cc(F)ccc4[nH]3)c2)C1 ; O=CO] | K | 484.00854 | 484 | 3.05 | method b |
| 146 | 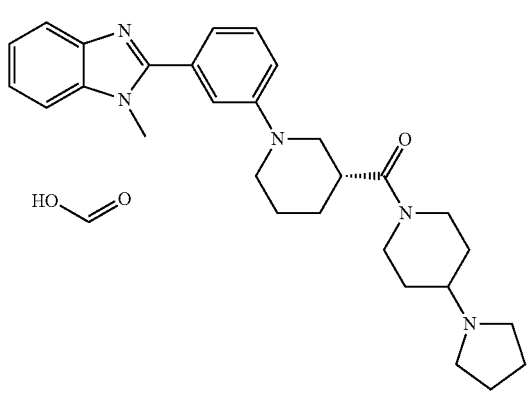 [SMILES: Cn1c(-c2cccc(N3CCC[C@@H](C(=O)N4CCC(N5CCCC5)CC4)C3)c2)nc2ccccc21 ; O=CO] | P | 471.63718 | 472 | 1.8 | method b |

| Example | Structure | Synthesis method | Calculated mass | Found mass | LCMS r.t. | LCMS method |
|---|---|---|---|---|---|---|
| 147 | 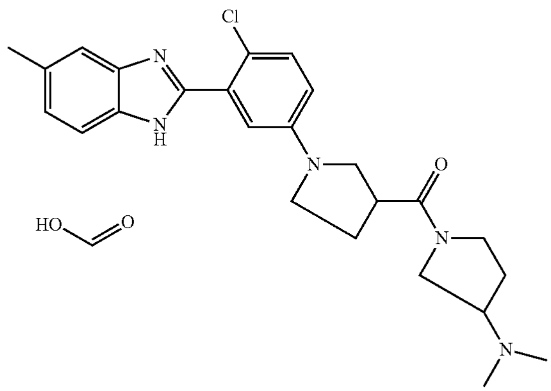 | P | 451.9915 | 452 | 2.22 | method b |
| 148 | 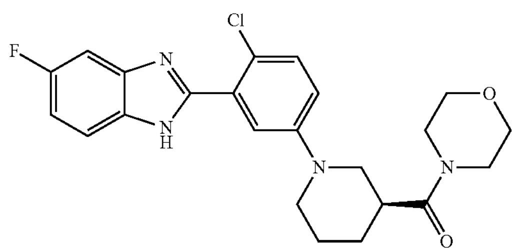 | K | 442.91352 | 443 | 5.02 | method b |
| 149 | 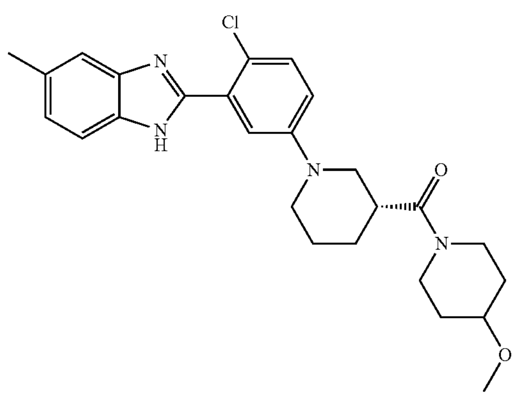 [SMILES: COC1CCN(C(=O)[C@@H]2CCCN(c3ccc(Cl)c(-c4nc5cc(C)ccc5[nH]4)c3)C2)CC1] | M | 467.0028 | 467 | 4.68 | method b |
| 150 | 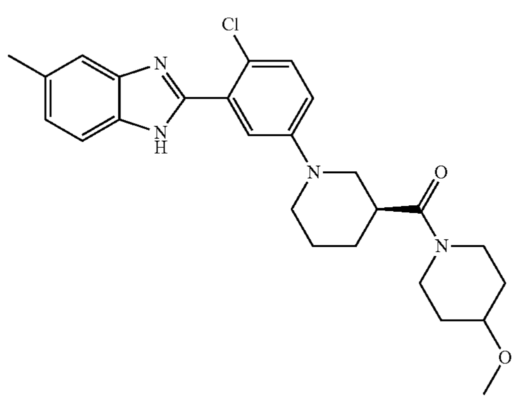 [SMILES: COC1CCN(C(=O)[C@H]2CCCN(c3ccc(Cl)c(-c4nc5cc(C)ccc5[nH]4)c3)C2)CC1] | M | 467.0028 | 467 | 4.68 | method b |

TABLE-continued
| Example | Structure | Synthesis method | Calculated mass | Found mass | LCMS r.t. | LCMS method |
|---|---|---|---|---|---|---|
| 151 | 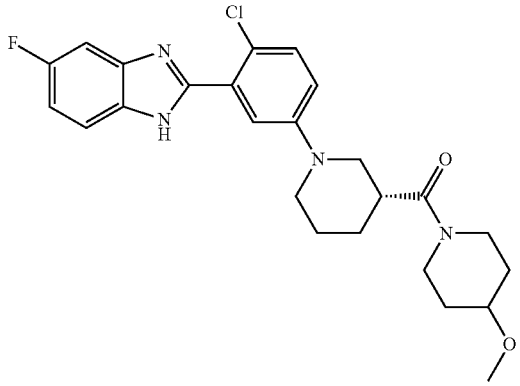 [SMILES: COC1CCN(C(=O)[C@@H]2CCCN(c3ccc(Cl)c(-c4nc5cc(F)ccc5[nH]4)c3)C2)CC1] | M | 470.96668 | 471 | 5.57 | method b |
| 152 | 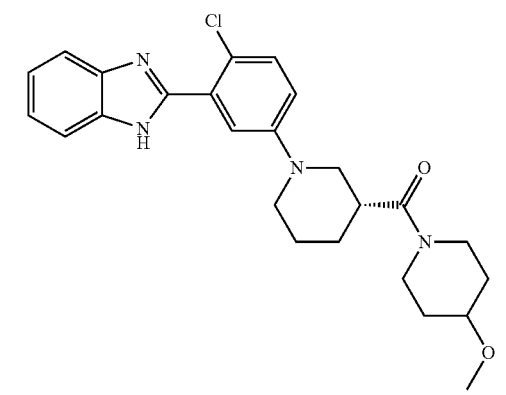 [SMILES: COC1CCN(C(=O)[C@@H]2CCCN(c3ccc(Cl)c(-c4nc5ccccc5[nH]4)c3)C2)CC1] | M | 452.97622 | 453 | 4.43 | method b |
| 153 | 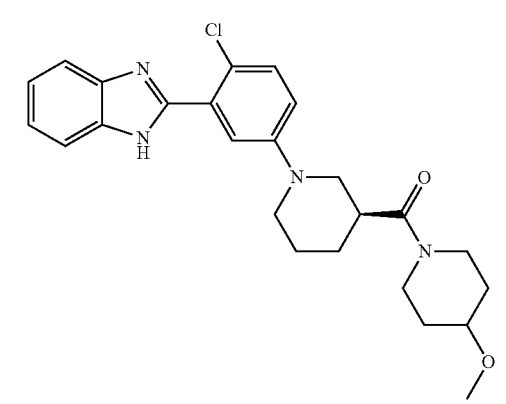 [SMILES: COC1CCN(C(=O)[C@H]2CCCN(c3ccc(Cl)c(-c4nc5ccccc5[nH]4)c3)C2)CC1] | M | 452.97622 | 453 | 4.45 | method b |

| Example | Structure | Synthesis method | Calculated mass | Found mass | LCMS r.t. | LCMS method |
|---|---|---|---|---|---|---|
| 154 | 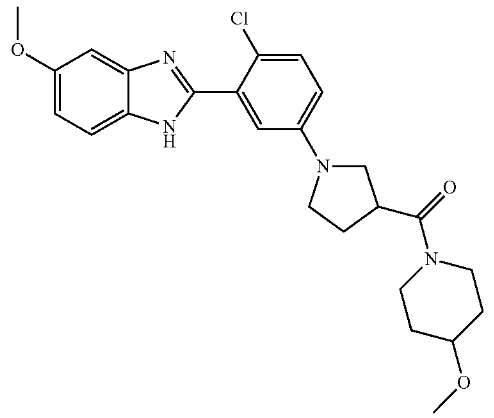 [SMILES: COc1ccc2[nH]c(-c3cc(N4CCC(C(=O)N5CCC(OC)CC5)C4)ccc3Cl)nc2c1] | M | 468.97562 | 469 | 4.28 | method b |
| 155 | 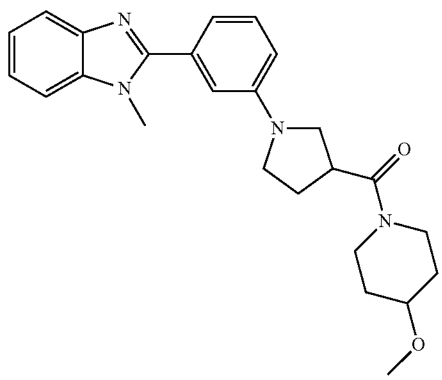 [SMILES: COC1CCN(C(=O)C2CCN(c3cccc(-c4nc5ccccc5n4C)c3)C2)CC1] | M | 418.53146 | 419 | 3.53 | method b |
| 156 | 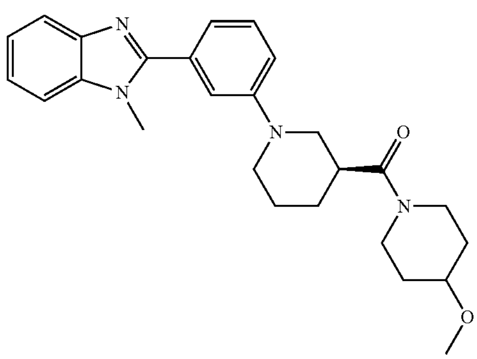 [SMILES: COC1CCN(C(=O)[C@H]2CCCN(c3cccc(-c4nc5ccccc5n4C)c3)C2)CC1] | M | 432.55804 | 433 | 3.6 | method b |
| 157 | 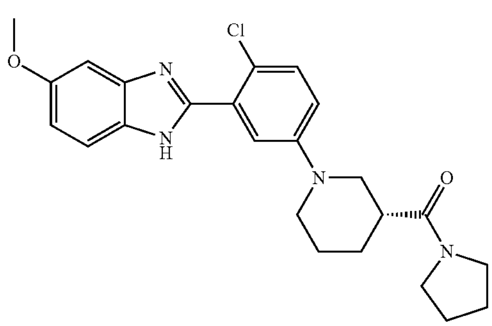 [SMILES: COc1ccc2[nH]c(-c3cc(N4CCC[C@@H](C(=O)N5CCCC5)C4)ccc3Cl)nc2c1] | O | 438.94964 | 439 | 4.42 | method b |

TABLE-continued

| Example | Structure | Synthesis method | Calculated mass | Found mass | LCMS r.t. | LCMS method |
|---|---|---|---|---|---|---|
| 158 | 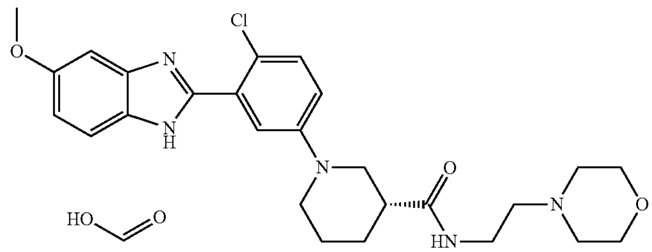 [SMILES: COc1ccc2[nH]c(-c3cc(N4CCC[C@@H](C(=O)NCCN5CCOCC5)C4)ccc3Cl)nc2c1 ; O=CO] | O | 498.01688 | 498 | 2.4 | method b |
| 159 | 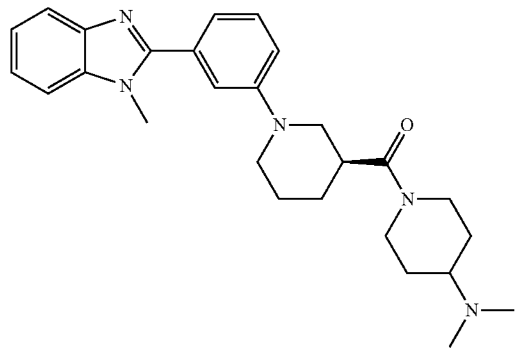 [SMILES: CN(C)C1CCN(C(=O)[C@H]2CCCN(c3cccc(-c4nc5ccccc5n4C)c3)C2)CC1] | N | 445.5999 | 446 | 1.65 | method b |
| 160 | 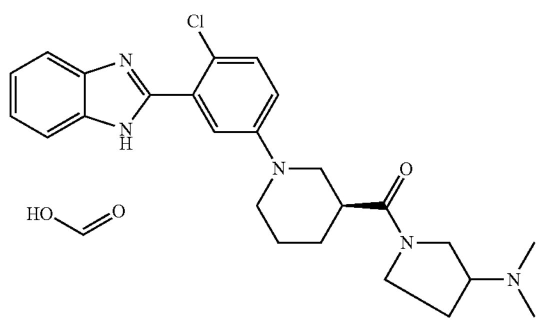 [SMILES: CN(C)C1CCN(C(=O)[C@H]2CCCN(c3ccc(Cl)c(-c4nc5ccccc5[nH]4)c3)C2)C1 ; O=CO] | O | 451.9915 | 452 | 1.87 | method b |
| 161 | 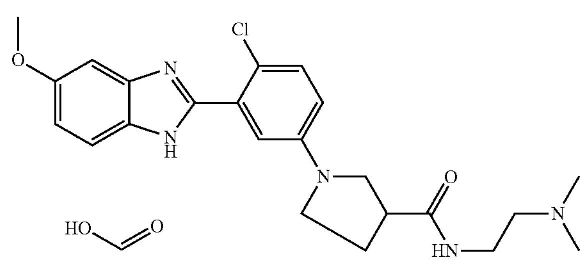 [SMILES: COc1ccc2[nH]c(-c3cc(N4CCC(C(=O)NCCN(C)C)C4)ccc3Cl)nc2c1 ; O=CO] | P | 441.95362 | 442 | 2.18 | method b |
| 162 | 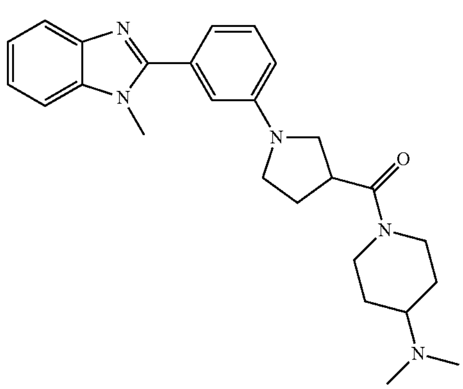 [SMILES: CN(C)C1CCN(C(=O)C2CCN(c3cccc(-c4nc5ccccc5n4C)c3)C2)CC1] | N | 431.57332 | 432 | 1.7 | method b |

TABLE-continued
| Example | Structure | Synthesis method | Calculated mass | Found mass | LCMS r.t. | LCMS method |
|---|---|---|---|---|---|---|
| 163 | 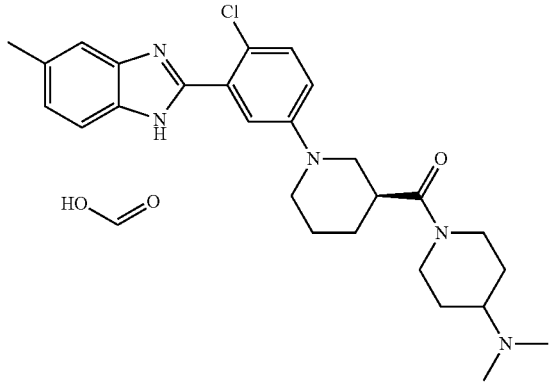 | N | 480.04466 | 480 | 2.45 | method b |
| 164 | 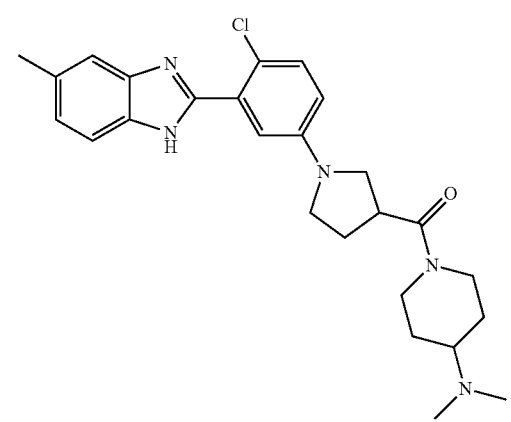 | N | 466.01808 | 466 | 2.43 | method b |
| 165 | 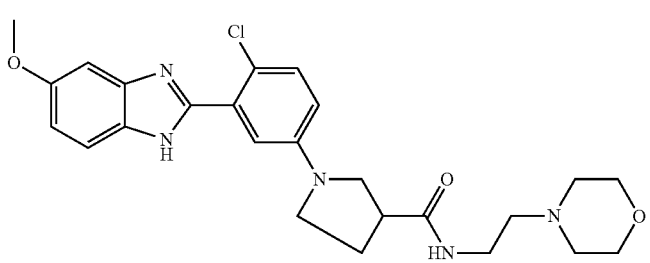 [SMILES: COc1ccc2[nH]c(-c3cc(N4CCC(C(=O)NCCN5CCOCC5)C4)ccc3Cl)nc2c1] | P | 483.9903 | 484 | 2.33 | method b |
| 166 | 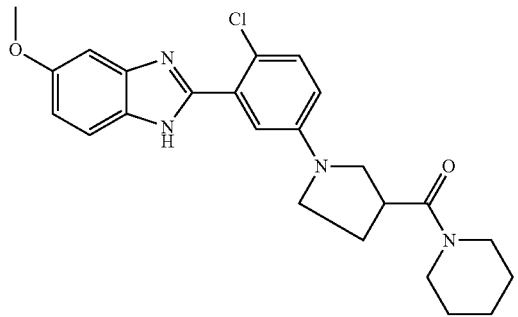 [SMILES: COc1ccc2[nH]c(-c3cc(N4CCC(C(=O)N5CCCCC5)C4)ccc3Cl)nc2c1] | O | 438.94964 | 439 | 4.58 | method b |

TABLE-continued

| Example | Structure | Synthesis method | Calculated mass | Found mass | LCMS r.t. | LCMS method |
|---|---|---|---|---|---|---|
| 167 | 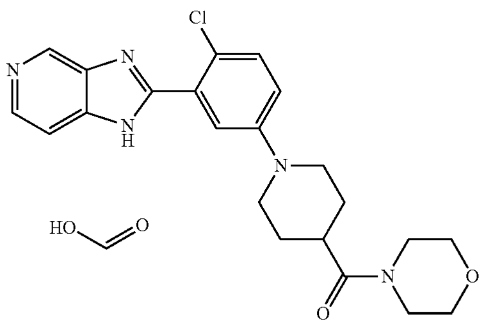 [SMILES: O=C(C1CCN(c2ccc(Cl)c(-c3nc4cnccc4[nH]3)c2)CC1)N1CCOCC1 ; O=CO] | C | 425.91116 | 426 | 2.63 | method b |
| 168 | 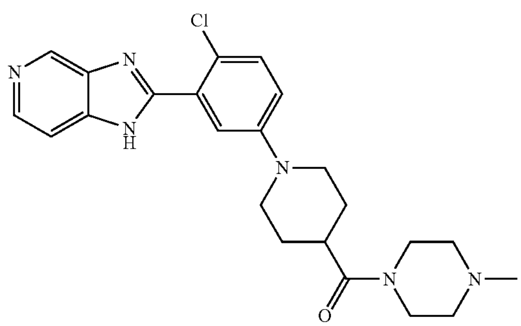 [SMILES: CN1CCN(C(=O)C2CCN(c3ccc(Cl)c(-c4nc5cnccc5[nH]4)c3)CC2)CC1] | C | 438.95302 | 439 | 0.62 | method b |
| 169 | 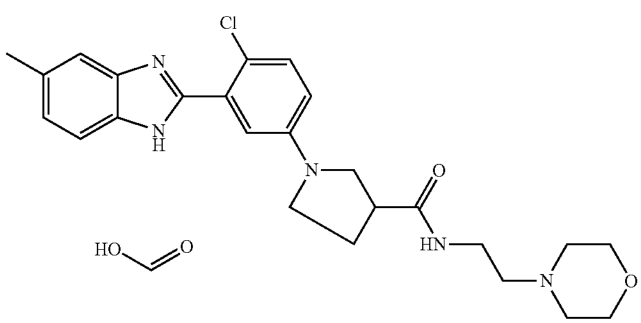 [SMILES: Cc1ccc2[nH]c(-c3cc(N4CCC(C(=O)NCCN5CCOCC5)C4)ccc3Cl)nc2c1 ; O=CO] | P | 467.9909 | 468 | 2.33 | method b |
| 170 | 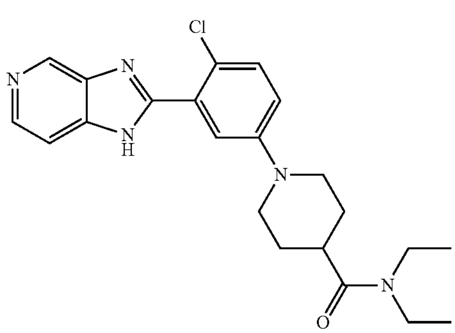 [SMILES: CCN(CC)C(=O)C1CCN(c2ccc(Cl)c(-c3nc4cnccc4[nH]3)c2)CC1] | C | 411.92764 | 412 | 3.2 | method b |

TABLE-continued

| Example | Structure | Synthesis method | Calculated mass | Found mass | LCMS r.t. | LCMS method |
|---|---|---|---|---|---|---|
| 171 | 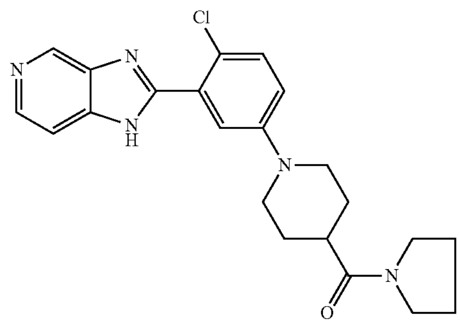 [SMILES: O=C(C1CCN(c2ccc(Cl)c(-c3nc4cnccc4[nH]3)c2)CC1)N1CCCC1] | C | 409.91176 | 410 | 3.02 | method b |
| 172 | 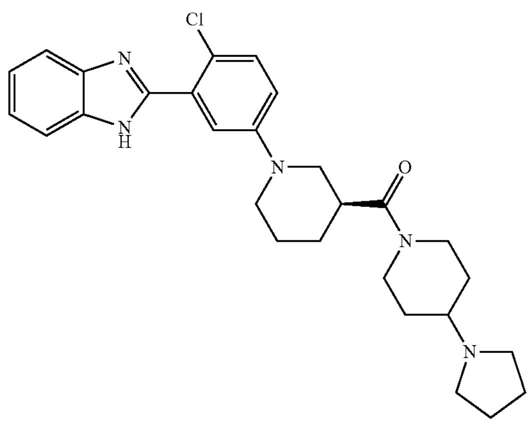 [SMILES: O=C([C@H]1CCCN(c2ccc(Cl)c(-c3nc4ccccc4[nH]3)c2)C1)N1CCC(N2CCCC2)CC1] | O | 492.05536 | 492 | 2.25 | method b |
| 173 | 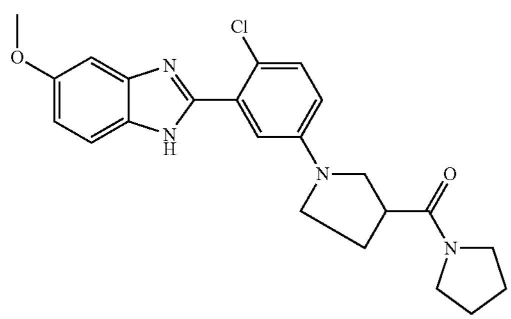 [SMILES: COc1ccc2[nH]c(-c3cc(N4CCC(C(=O)N5CCCC5)C4)ccc3Cl)nc2c1] | P | 424.92306 | 425 | 4.15 | method b |
| 174 | 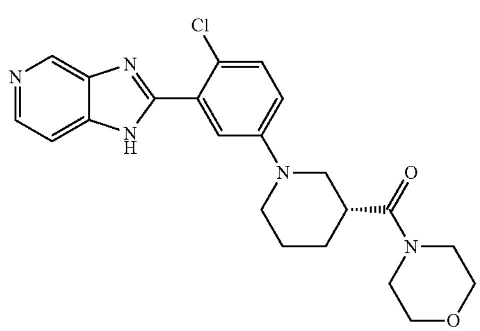 [SMILES: O=C([C@@H]1CCCN(c2ccc(Cl)c(-c3nc4cnccc4[nH]3)c2)C1)N1CCOCC1] | C | 425.91116 | 426 | 2.77 | method b |

TABLE-continued
| Example | Structure | Synthesis method | Calculated mass | Found mass | LCMS r.t. | LCMS method |
|---|---|---|---|---|---|---|
| 175 | 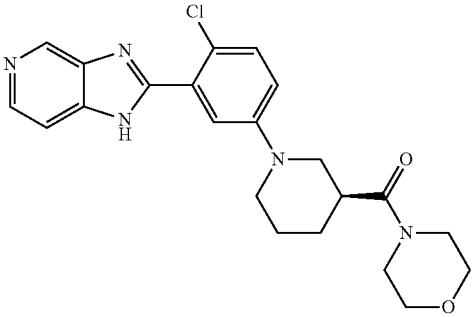 [SMILES: O=C([C@H]1CCCN(c2ccc(Cl)c(-c3nc4cnccc4[nH]3)c2)C1)N1CCOCC1] | C | 425.91116 | 426 | 2.68 | method b |
| 176 | 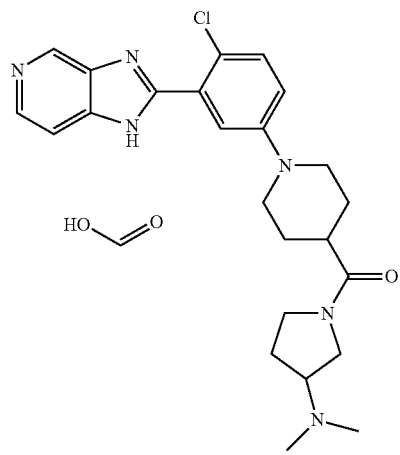 [SMILES: CN(C)C1CCN(C(=O)C2CCN(c3ccc(Cl)c(-c4nc5cnccc5[nH]4)c3)CC2)C1 ; O=CO] | C | 452.9796 | 453 | 1.47 | method b |
| 177 | 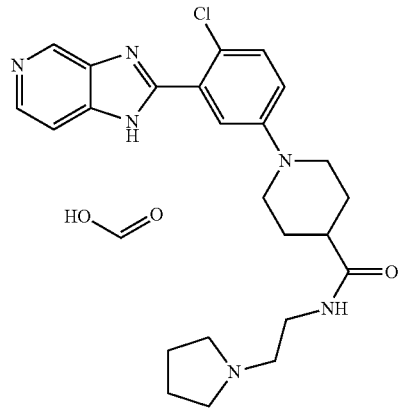 [SMILES: O=C(NCCN1CCCC1)C1CCN(c2ccc(Cl)c(-c3nc4cnccc4[nH]3)c2)CC1 ; O=CO] | C | 452.9796 | 453 | 1.47 | method b |
| 178 | 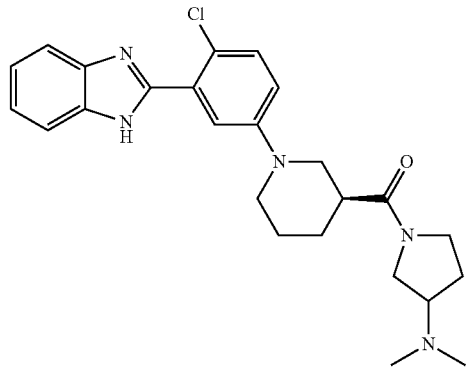 [SMILES: CN(C)C1CCN(C(=O)[C@H]2CCCN(c3ccc(Cl)c(-c4nc5ccccc5[nH]4)c3)C2)C1] | Q | 451.9915 | 452 | 1.97 | method b |

| Example | Structure | Synthesis method | Calculated mass | Found mass | LCMS r.t. | LCMS method |
|---|---|---|---|---|---|---|
| 179 | 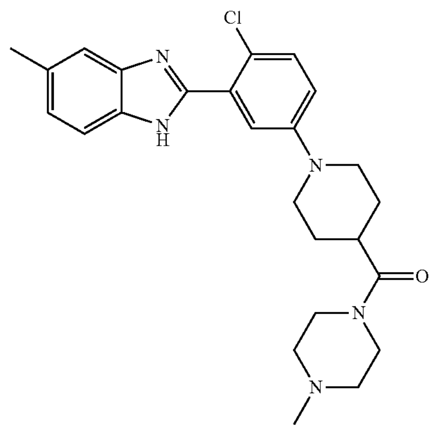 [SMILES: Cc1ccc2[nH]c(-c3cc(N4CCC(C(=O)N5CCN(C)CC5)CC4)ccc3Cl)nc2c1] | Q | 451.9915 | 452 | 2.08 | method b |
| 180 | 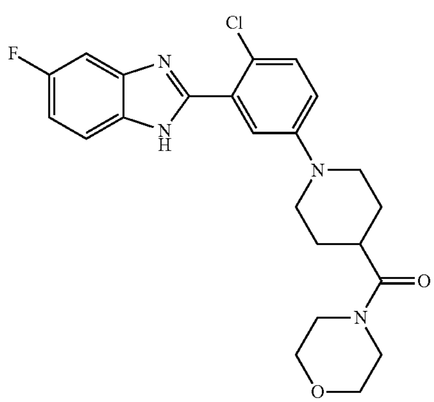 [SMILES: O=C(C1CCN(c2ccc(Cl)c(-c3nc4cc(F)ccc4[nH]3)c2)CC1)N1CCOCC1] | Q | 442.91352 | 443 | 4.55 | method b |
| 181 | 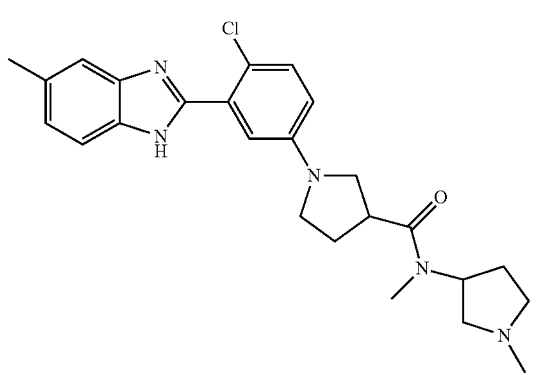 [SMILES: Cc1ccc2[nH]c(-c3cc(N4CCC(C(=O)N(C)C5CCN(C)C5)C4)ccc3Cl)nc2c1] | Q | 451.9915 | 452 | 2.3 | method b |

TABLE-continued

| Example | Structure | Synthesis method | Calculated mass | Found mass | LCMS r.t. | LCMS method |
|---|---|---|---|---|---|---|
| 182 | 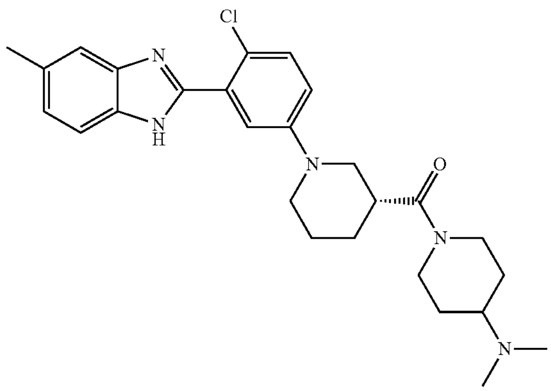 | Q | 480.04466 | 480 | 2.45 | method b |
| 183 | 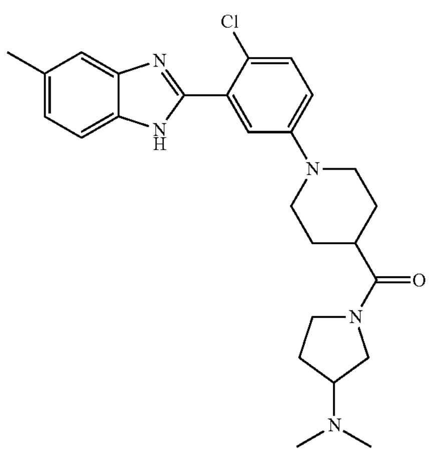 [SMILES: Cc1ccc2[nH]c(-c3cc(N4CCC(C(=O)N5CCC(N(C)C)C5)CC4)ccc3Cl)nc2c1] | Q | 466.01808 | 466 | 2.08 | method b |
| 184 | 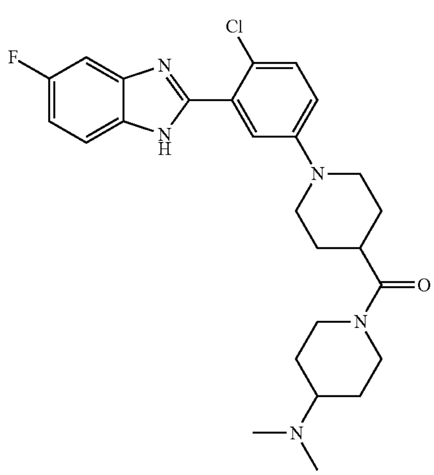 [SMILES: CN(C)C1CCN(C(=O)C2CCN(c3ccc(Cl)c(-c4nc5cc(F)ccc5[nH]4)c3)CC2)CC1] | M | 484.00854 | 484 | 2.38 | method b |

TABLE-continued
| Example | Structure | Synthesis method | Calculated mass | Found mass | LCMS r.t. | LCMS method |
|---|---|---|---|---|---|---|
| 185 | 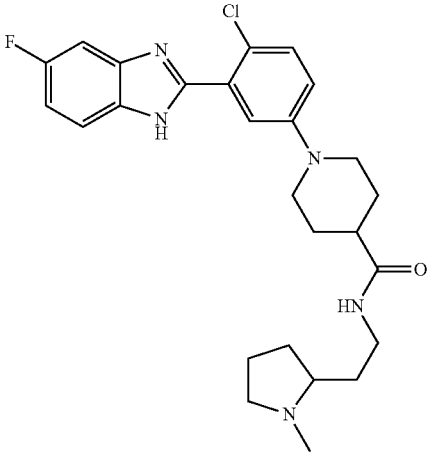 [SMILES: CN1CCCC1CCNC(=O)C1CCN(c2ccc(Cl)c(-c3nc4cc(F)ccc4[nH]3)c2)CC1] | M | 484.00854 | 484 | 2.67 | method b |
| 186 | 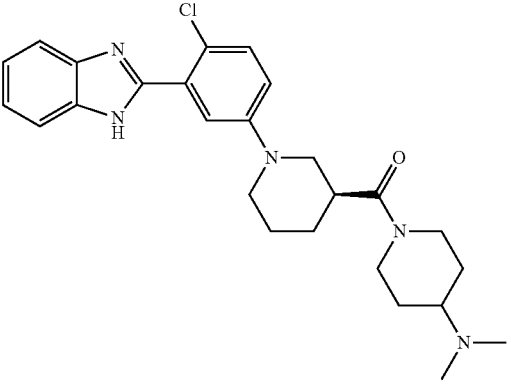 [SMILES: CN(C)C1CCN(C(=O)[C@H]2CCCN(c3ccc(Cl)c(-c4nc5ccccc5[nH]4)c3)C2)CC1] | Q | 466.01808 | 466 | 2.05 | method b |
| 187 | 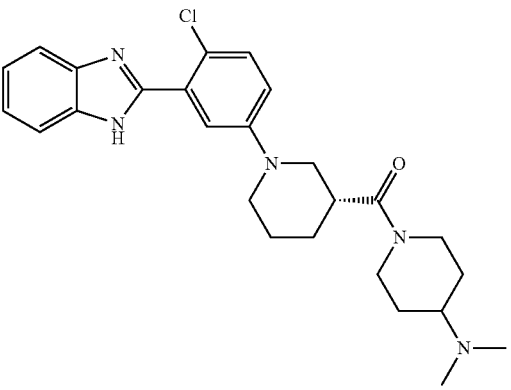 [SMILES: CN(C)C1CCN(C(=O)[C@@H]2CCCN(c3ccc(Cl)c(-c4nc5ccccc5[nH]4)c3)C2)CC1] | Q | 466.01808 | 467 | 2.05 | method b |

TABLE-continued

| Example | Structure | Synthesis method | Calculated mass | Found mass | LCMS r.t. | LCMS method |
|---|---|---|---|---|---|---|
| 188 | 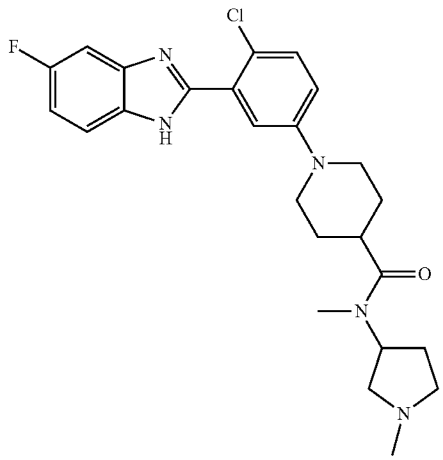 [SMILES: CN1CCC(N(C)C(=O)C2CCN(c3ccc(Cl)c(-c4nc5cc(F)ccc5[nH]4)c3)CC2)C1] | Q | 469.98196 | 470 | 2.57 | method b |
| 189 | 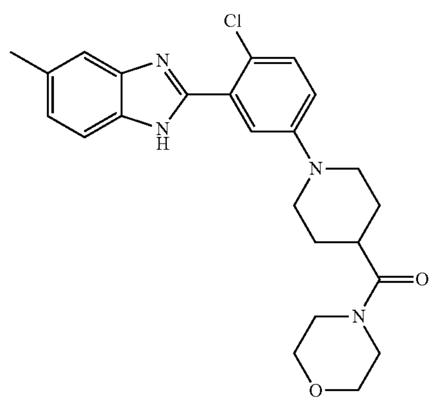 [SMILES: Cc1ccc2[nH]c(-c3cc(N4CCC(C(=O)N5CCOCC5)CC4)ccc3Cl)nc2c1] | Q | 438.94964 | 439 | 3.9 | method b |
| 190 | 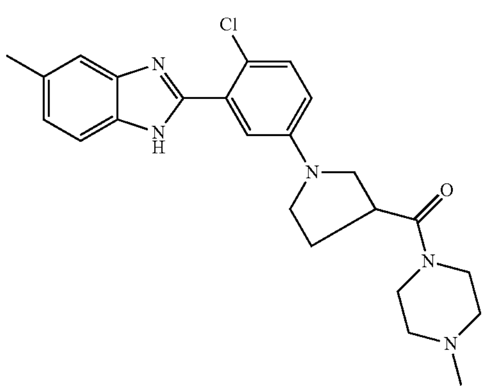 [SMILES: Cc1ccc2[nH]c(-c3cc(N4CCC(C(=O)N5CCN(C)CC5)C4)ccc3Cl)nc2c1] | Q | 437.96492 | 438 | 2.12 | method b |

TABLE-continued

| Example | Structure | Synthesis method | Calculated mass | Found mass | LCMS r.t. | LCMS method |
|---|---|---|---|---|---|---|
| 191 | 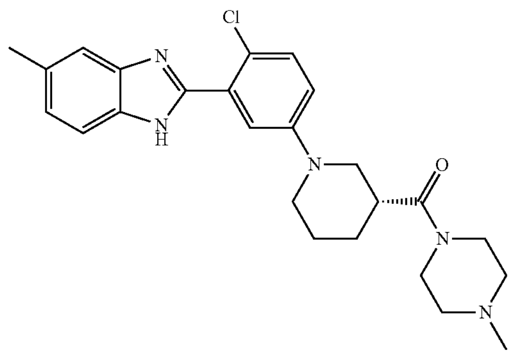 | Q | 451.9915 | 452 | 2.28 | method b |
| 192 | 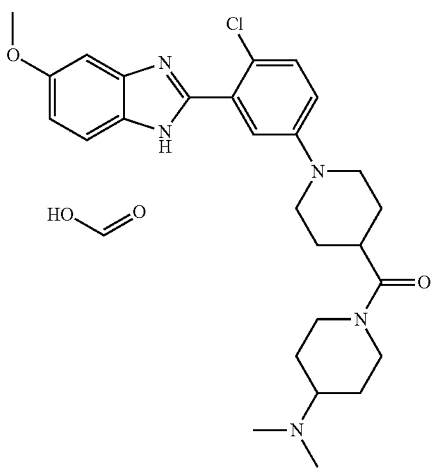 [SMILES: COc1ccc2[nH]c(-c3cc(N4CCC(C(=O)N5CCC(N(C)C)CC5)CC4)ccc3Cl)nc2c1 ; O=CO] | Q | 496.04406 | 496 | 2.3 | method b |
| 193 | 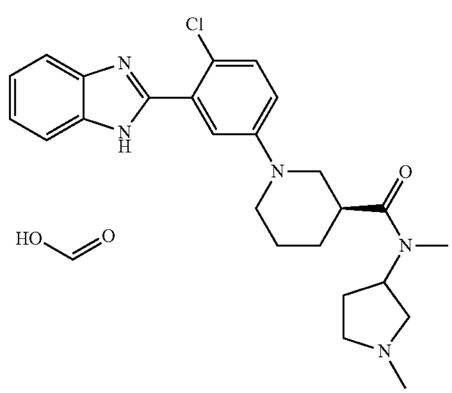 [SMILES: CN1CCC(N(C)C(=O)[C@H]2CCCN(c3ccc(Cl)c(-c4nc5ccccc5[nH]4)c3)C2)C1 ; O=CO] | Q | 451.9915 | 452 | 2.15 | method b |

Cloning of Smo and Generation of Stable Recombinant Smo Expressing Cell Lines

The human Smo coding sequence was amplified by PCR using standard conditions. The template was ipcMV6-XL5-Smo from Origene (cat. TC122724). The primers were designed as follows:

Forward (5' GATCGGTACCGGGCTTTTGCTGAGTT 3') has a KpnI restriction site;

Reverse (5' GATCGCGGCCGCCTACTTATCGTCGT-CATCCTTG TAATCGAAGTCCGAGTCTGC 3') has a NotI restriction site, a stop codon and a FLAG-coding sequence at the 5' end.

The obtained amplicon was 2424 bp long and contained the complete Smo-coding sequence, a FLAG-tag and two restriction sites, one at each end. The amplicon was double-digested with KpnI and NotI restriction enzymes, as well as pcDNA5/FRT plasmid (Invitrogen) chosen for cloning. The ligation and cloning of the Smo-FLAG coding sequence into the pcDNA5/FRT plasmid produced a plasmid that was named pcDNA5/FRT_Smo-FLAG and that was 7432 bp long.

The FlpIN technique (Invitrogen) was used to create the stable expressing Smo-FLAG cell line using the FlpIN293 cell line (Invitrogen, RT50-07). This is a line derived from HEK293 cells by stable transfection with pFRT/lacZeo plasmid to generate the zeocin-resistant FlpIN293 host cell line.

FlpIN293 cells are suitable to create a stable mammalian cell line containing an integrated Flp Recombinant Target (FRT) site (Invitrogen).

Transfection with pcDNA5/FRT_Smo-FLAG plasmid (or, in the case of the mock transfected cells, transfection with the empty plasmid) was made together with transfection of pOG44 plasmid, carrying the Flp recombinase, that catalyzed a homologous recombination between the FRT site in the host cells and the pcDNA5/FRT_Smo-FLAG expression vector or the pcDNA5/FRT empty vector respectively. Smo-FLAG expressing cells as well as mock transfected cells possess hygromycin B resistance and are negative to β-gal staining. The expression of Smo and FLAG antigens was checked also by western blot. The two cell lines generated were named 293FlpIN/clone E-3 indicating the mock transfected and 293FlpIN/clone 3-5 indicating the Smo-FLAG transfected cell line.

Cell Cultures Conditions

Cells were maintained in DMEM containing 10% foetal bovine serum (both from Invitrogen), with addition of 0.25 mg/ml hygromycin B (Invitrogen). Cells were maintained at 37° C. in a 95% air-5% carbon dioxide fully humidified environment, and used up to 22-25 cycles after thawing.

Binding Assay Development

The interaction of compounds with the Smo receptor was tested by a displacement binding assay using fluorescent ligand for the Smo receptor (Bodipy-Cyclopamine, Toronto Research Chemical Inc, cat#B674800) as the labeled ligand to be displaced.

In order to determine the Kd (concentration of the ligand where 50% of the maximal binding is reached) and the Bmax (maximal amount of ligand which can bind specifically to the receptor in a biological preparation) of the fluorescent ligand, the Specific Binding (SB) was calculated by subtraction Non Specific Binding (NSB) from Total Binding (TB). The TB was determined by adding increasing concentration of Bodipy-Cyclopamine to the cells, while the NSB was determined by adding a mixture of increasing concentration of Bodipy-Cyclopamine with a saturating concentration of an well described antagonist (in this case, N-[3-(1H-benzimidazol-2-yl)-4-chlorophenyl]-3,5-dimethoxy-benzamide (Rubin et al. WO2003011219) at 10 µM was selected) to the cells. For each concentration of Bodipy-Cyclopamine, the SB was calculated by subtracting the value of NSB from TB. From the SB curve Bmax and Kd were calculated. In this case, the stable mock transfected cell line clone E-3 was found to have a Kd of 115 nM, while the stable Smo-FLAG transfected cell line clone 3-5 was found to have a Kd of 44.3 nM. The Ki is the concentration of non labeled ligand which inhibits 50% of the specific binding (SB) of the labeled ligand, and corrected for the effective used concentration of the labeled ligand. Ki was calculated following the Cheng-Prusoff equation, as $Ki=IC_{50}/[1+[bodipy-cyclopamine]/Kd)]$.

Testing Compounds with the Binding Assay

293FlpIN/clone E-3 and 293FlpIN/clone 3-5 cells were counted with a Burker chamber and 100000 cells/1000 µl DMEM 1% FBS were transferred in two 96 well plates (U bottom, Sigma Aldrich, cat#M8185-100EA). 293FlpIN/clone E-3 cells were used as internal control to check Smo over-expressing 293FlpIN/clone 3-5 cells fluorescence (FLU) variation in time.

Controls and compounds were prepared in DMEM 1% FBS and 100 µl were added to the cells. All the controls and compounds were incubated with a final concentration of 5 nM Bodipy-Cyclopamine.

Compounds were dissolved in DMSO (stock 10 mM), and were tested first at 10 µM (single concentration assay); each compound was repeated at least twice (in two different plates). When Bodipy-Cyclopamine was displaced above a 30% threshold the compound was re-tested with a concentration-response assay with a throughput of 8 compounds per plate and the concentration range was: 100, 10, 1, 0.5, 0.1, 0.01, 0.05, 0.001 and 0.0001 µM.

As negative control 293FlpIN/clone 3-5 cells were used in which DMSO was added diluted 1:1000 for single concentration assay and 1:100 for concentration response assay.

As positive control to completely displace Bodipy-Cyclopamine binding, N-[3-(1H-benzimidazol-2-yl)-4-chlorophenyl]-3,5-dimethoxy-benzamide (Rubin et al. WO2003011219) was used at a concentration of 10 µM.

The two plates were incubated 4 hours at room temperature protected from light on a rocking platform. After incubation plates were centrifuged for 5 min. at 1600 rpm and washed twice with PBS containing 2% FBS. Cells were finally re-suspended in 170 µl of washing buffer and fluorescent signals were acquired with FACScalibur HTS system (Becton Dickinson).

Instrument acquisition parameters were set at the beginning of the reading of each plate using untreated non-labeled 293FlpIN/clone E-3 cells. The HTS acquisition program used was BD™ Plate Manager (BD Bioscience) and data analysis was performed using BD CellQuest™ Pro software (BD Bioscience).

Quantification was made by overlaying the FL1-H histograms of the positive and negative controls and setting a marker at the intersection between the two curves. Only those events more fluorescent than the set marker were quantified. Values were then normalized according to the negative control (0% Bodipy-Cyclopamine displacement) and the positive control (100% Bodipy-Cyclopamine displacement).

Compounds from examples 1-193 when tested in the above conditions, all display a Ki value ranging between 0.8 nM and 21.6 µM.

Testing Compounds with an Alkaline Phosphatase Assay

Shh has been demonstrated in vitro to induce alkaline phosphatase (AP), a marker of osteoblast differentiation, in the mouse mesenchymal cell line C3H10T1/2 (Katsuura et al., 1999; Kinto et al., 1997; Murone et al., 1999; Nakamura et al., 1997, Wu et al. 2004. Therefore and to analyse interference of small molecules with Hedgehog-Gli signaling a functional assay based on activation of AP in this mouse cell line was implemented. The substrate of the AttoPhos® kit (Cat S1000, Promega) was used to detect AP in solution. Briefly, the following procedure was applied.

Polylysine-coated clear, flat bottomed 96-well plates (Corning, Cat. 3667) were filled with 10.000 cells in 100 µl of cell culture solution per well. Cell culture medium consisted of DMEM (Cat 21969-035) with 1% Glutamax (Cat 35050-038), 1% Penicillin/Streptomycin (Cat 15140-122) and 1% Hepes (15630-056). All reagents were obtained from Invitrogen. The plates were incubated overnight at 37° C. with 5% carbon dioxide. Then medium was removed, and 100 µl of fresh medium containing either compound or reference antagonist (N-[3-(1H-benzimidazol-2-yl)-4-chlorophenyl]-3,5-dimethoxy-benzamide (Rubin et al. WO2003011219)) was added to the wells. All compound and reference solutions contained the agonist purmorphamine (Sinha et al. Nature Chem. Biol. 2, 29-30 (2005)) at a concentration of 2 µM. Compounds were tested at ten concentrations in triplicates in the range between 100 pM and 50 µM. The final DMSO concentration in each sample was adjusted to 1% in culture medium. Cells were incubated with compound solution for 72 hours at 37° C. in the presence of 5% carbon dioxide. Cell culture medium was removed from the plates, and 40 µl of a 1:5 diluted lysis solution (Cat E194A, Promega) was added to each well. Plates were then incubated in the dark for 20 minutes on a shaker. Finally, 40 μl of reconstituted AttoPhos substrate solution was added to the wells, followed by another incubation period of 15 minutes on a shaker. The AttoPhos substrate was reconstituted according to the instructions of the supplier but substrate solution was always stored at −80° C. The Safire 2 plate reader (Tecan) was used for measurement of changes in fluorescence intensity in the samples, with an excitation wavelength of 430 nm and an emission wavelength of 560 nm.

Compounds from examples 1-193 when tested in the above conditions, all display an $IC_{50}$ value ranging between 1.1 μM and 14.8 μM.

The invention claimed is:
1. Compounds of formula I and pharmaceutically acceptable salts thereof

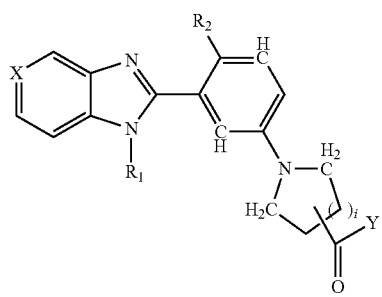

wherein, as valence permits,
i is 1 or 2
$R_1$ is H; linear ($C_1$-$C_4$) alkyl group, branched or cyclic ($C_3$-$C_4$) alkyl group
$R_2$ is H, Cl or F
X is either N or $CR_3$
$R_3$ is H; halogen; a linear ($C_1$-$C_4$) alkyl or alkoxy group, branched or cyclic ($C_3$-$C_4$) alkyl or alkoxy group,
Y is

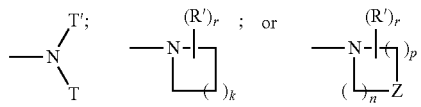

Z is O or NRx
Rx is H or a linear ($C_1$-$C_4$) alkyl group, branched or cyclic ($C_3$-$C_4$) alkyl group
k is 1, 2, 3 or 4
n and p are independently 1, 2 or 3 and the sum n+p cannot exceed 5
T is H or a linear ($C_1$-$C_4$) alkyl group or branched ($C_3$-$C_4$) alkyl group;
T' is a linear ($C_1$-$C_3$) alkyl chain or branched $C_3$ alkyl chain substituted with either a ($C_1$-$C_6$)-dialkylamino group or a 4 to 6 membered saturated heterocycle containing one nitrogen atom and optionally containing a second heteroatom selected from N and O, such heterocyclic ring being optionally substituted a the nitrogen atoms with a ($C_1$-$C_4$) alkyl chain; or a 4 to 6 membered saturated heterocycle containing one nitrogen atom and optionally containing a second heteroatom selected from N and O, such heterocyclic ring being optionally substituted at the nitrogen atoms with a ($C_1$-$C_4$) alkyl chain r is zero, 1, 2 or 3;
R' is halogen; hydroxy; amino; cyano; nitro; oxo; linear ($C_1$-$C_6$) alkyl, or branched ($C_3$-$C_6$) alkyl, dihaloalkyl, azaalkyl, oxaalkyl, alkylcarbonyl, oxaalkylcarbonyl, alkoxycarbonyl, alkylaminocarbonyl, alkylcarbonylamino, alkenyl, oxaalkenyl, azaalkenyl, alkenylcarbonyl, oxaalkenylcarbonyl, alkenyloxycarbonyl, alkenylaminocarbonyl, alkylamino, dialkylamino, mercaptoalkyl, alkoxy, or alkylthio group optionally substituted with one or more fluorine atoms; or wherein two R' groups may form a 5- to 8-membered ring with spiro or fused junction;
with the exclusion of:

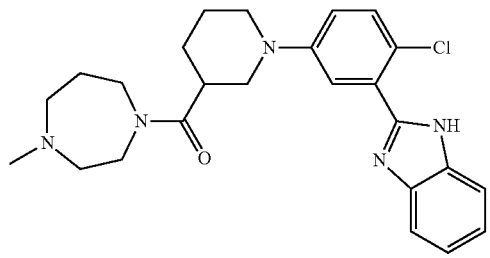

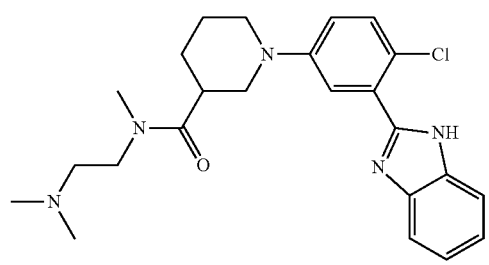

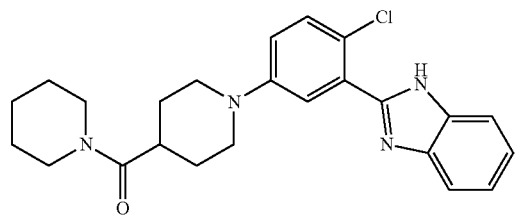

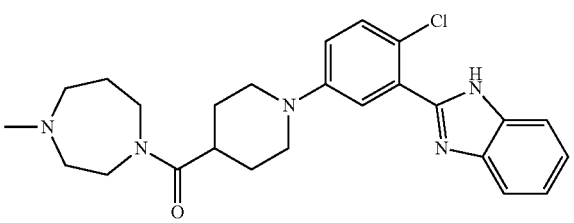

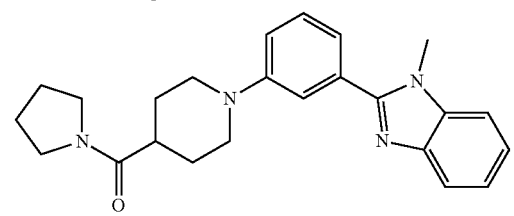

139
-continued
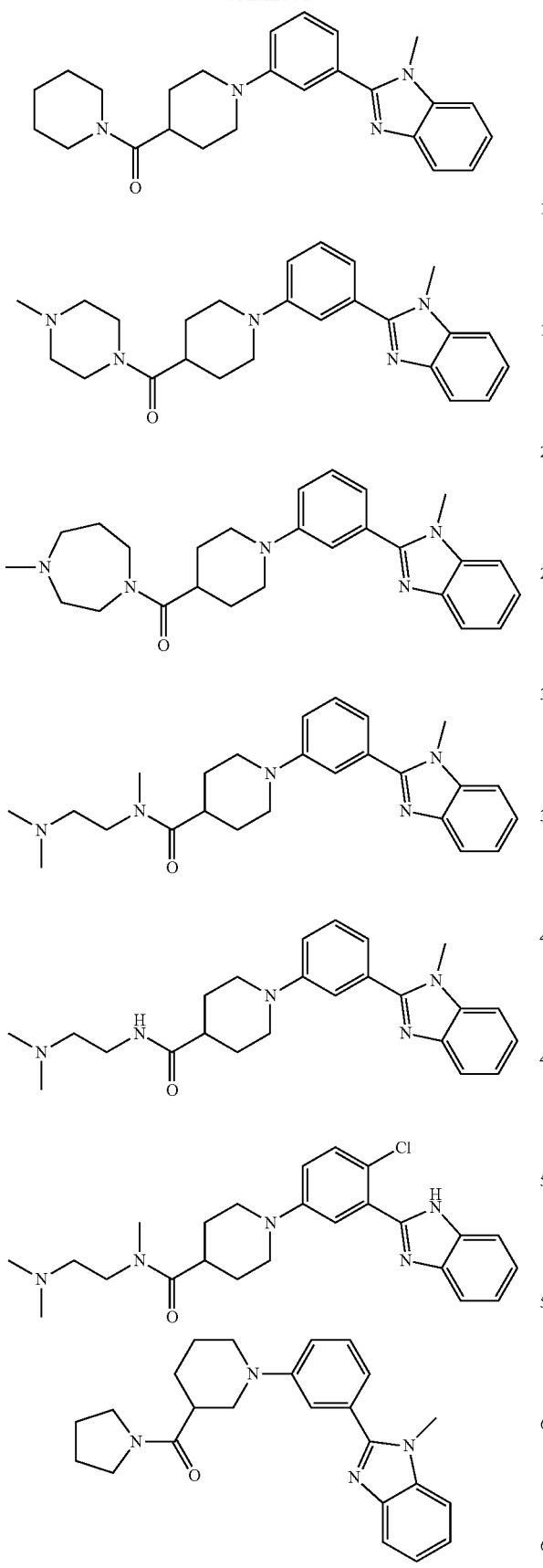
140
-continued
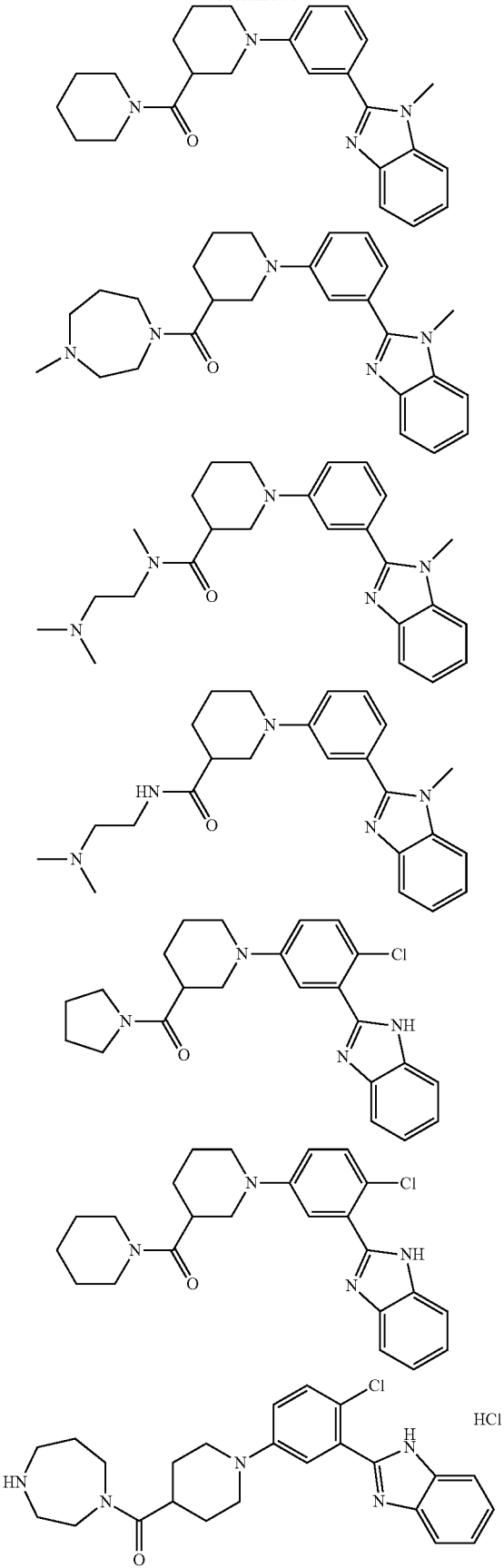

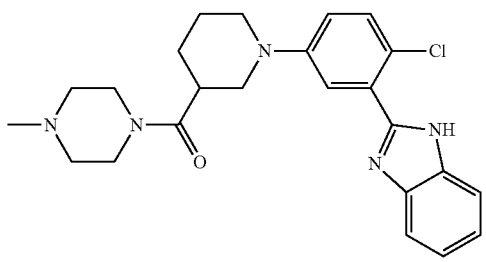

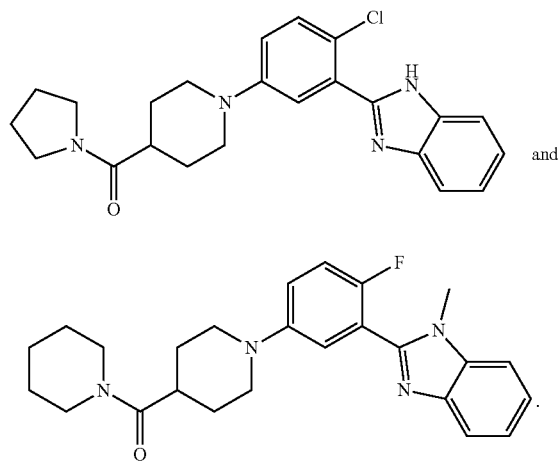

2. Compounds according to claim 1 wherein i equals 2 and —C(=O)—Y stands in the 4 position of the ensuing piperidine ring and wherein $R_1$, $R_2$, X, $R_3$, Y, Z, Rx, k, n, p, T, T', r and R' are as defined in claim 1.

3. Compounds according to claim 1 wherein i equals 2 and —C(=O)—Y stands in the 3 position of the ensuing piperidine ring and wherein $R_1$, $R_2$, X, $R_3$, Y, Z, Rx, k, n, p, T, T', r and R' are as defined in claim 1.

4. Compounds according to claim 1 wherein i equals 1 and wherein $R_1$, $R_2$, X, $R_3$, Y, Z, Rx, k, n, p, T, T', r and R' are as defined in claim 1.

5. Compounds according to claim 1 wherein $R_1$ is H, $R_2$ is Cl or F and wherein i, X, $R_3$, Y, Z, Rx, k, n, p, T, T', r and R' are as defined in claim 1.

6. Compounds according to claim 1 wherein $R_2$ is H, $R_1$ is linear ($C_1$-$C_4$) alkyl group, branched or cyclic ($C_3$-$C_4$) alkyl group and wherein i, X, $R_3$, Y, Z, Rx, k, n, p, T, T', r and R' are as defined in claim 1.

7. Compounds according to claim 1 wherein X is N and wherein i, $R_1$, $R_2$, $R_3$, Y, Z, Rx, k, n, p, T, T', r and R' are as defined in claim 1.

8. Compounds according to claim 1 wherein X is $CR_3$ and wherein i, $R_1$, $R_2$, $R_3$, Y, Z, Rx, k, n, p, T, T', r and R' are as defined in claim 1.

9. Compounds according to claim 8 wherein $R_3$ is H and wherein i, $R_1$, $R_2$, Y, Z, Rx, k, n, p, T, T', r and R' are as defined in claim 8.

10. Compounds according to claim 1 wherein $R_3$ is Cl, F, OMe or Me and wherein i, $R_1$, $R_2$, Y, Z, Rx, k, n, p, T, T', r and R' are as defined in claim 1.

11. Compounds according to claim 1 wherein r equals zero.

12. Compounds according to claim 1 wherein Y is

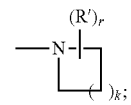

and wherein k equals 2, r equals 1, R' is dimethylamino and i, $R_1$, $R_2$, X, and $R_3$ are as defined in claim 1.

13. Compounds according to claim 1 wherein Y is

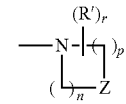

and wherein both n and p equal 2, Z is O, r equals zero and wherein i, $R_1$, $R_2$, X, and $R_3$ are as defined in claim 1.

14. Compounds according to claim 1 wherein i equals 2 and —C(=O)—Y stands in the 4 position of the ensuing piperidine ring, X is C $R_3$, $R_3$ is methyl, $R_2$ is F and wherein $R_1$, Y, Z, Rx, k, n, p, T, T', r and R' are as defined in claim 1.

15. A compound according to claim 1, which is selected from the group of:
{1-[4-Fluoro-3-(5-methyl-1H-benzoimidazol-2-yl)-phenyl]-piperidin-4-yl}-piperazin-1-yl-methanone;
Azepan-1-yl-{1-[4-fluoro-3-(5-methyl-1H-benzoimidazol-2-yl)-phenyl]-piperidin-4-yl}-methanone;
{1-[4-Fluoro-3-(5-methyl-1H-benzoimidazol-2-yl)-phenyl]-piperidin-4-yl}-pyrrolidin-1-yl-methanone,
{1-[4-Fluoro-3-(5-methyl-1H-benzoimidazol-2-yl)-phenyl]-piperidin-4-yl}-piperidin-1-yl-methanone;
{(S)-1-[3-(1H-Benzoimidazol-2-yl)-4-chloro-phenyl]-piperidin-3-yl}-morpholin-4-yl-methanone;
{1-[3-(1H-Benzoimidazol-2-yl)-4-chloro-phenyl]-piperidin-4-yl}-morpholin-4-yl-methanone;
1-[4-Fluoro-3-(5-methyl-1H-benzoimidazol-2-yl)-phenyl]-piperidine-4-carboxylic acid (3-dimethylamino-propyl)-methyl-amide;
{1-[4-Fluoro-3-(5-methyl-1H-benzoimidazol-2-yl)-phenyl]-piperidin-4-yl}-(4-methyl-piperazin-1-yl)-methanone;
{1-[4-Fluoro-3-(5-methyl-1H-benzoimidazol-2-yl)-phenyl]-piperidin-4-yl}-(4-pyrrolidin-1-yl-piperidin-1-yl)-methanone;
{1-[4-Fluoro-3-(5-methyl-1H-benzoimidazol-2-yl)-phenyl]-piperidin-4-yl}-morpholin-4-yl-methanone;
{1-[4-Chloro-3-(5-methoxy-1H-benzoimidazol-2-yl)-phenyl]-piperidin-4-yl}-morpholin-4-yl-methanone;
{(R)-1-[3-(1H-Benzoimidazol-2-yl)-4-chloro-phenyl]-piperidin-3-yl}-morpholin-4-yl-methanone;
{(S)-1-[3-(1-Methyl-1H-Benzoimidazol-2-yl)-phenyl]-piperidin-3-yl}-morpholin-4-yl-methanone;
{(R)-1-[3-(1-Methyl-1H-Benzoimidazol-2-yl)-phenyl]-piperidin-3-yl}-morpholin-4-yl-methanone;
{1-[4-Fluoro-3-(5-fluoro-1H-benzoimidazol-2-yl)-phenyl]-piperidin-4-yl}-morpholin-4-yl-methanone;
(3-Dimethylaminopyrrolidin-1-yl)-{(R)-1-[3-(1-methyl-1H-benzoimidazol-2-yl-) -phenyl]-piperidin-3-yl}-methanone;
{(R)-1-[4-Chloro-3-(5-methyl-1H-benzoimidazol-2-yl)-phenyl]-piperidin-3-yl}-(3-dimethylamino-pyrrolidin-1-yl)-methanone;
{(S)-1-[4-Chloro-3-(5-methyl-1H-benzoimidazol-2-yl)-phenyl]-piperidin-3-yl}-morpholin-4-yl-methanone;

{1-[3-(1H-Benzoimidazol-2-yl)-4-chloro-phenyl]-pyrrolidin-3-yl}-(3-dimethylamino-pyrrolidin-1-yl)-methanone, (3-Dimethylamino-pyrrolidin-1-yl)-{(S)-1-[3-(1-methyl-1H-benzoimidazol-2-yl)-phenyl]-piperidin-3-yl}-methanone;

(3-Dimethylamino-pyrrolidin-1-yl)-{(R)-1-[3-(1-methyl-1H-benzoimidazol-2-yl)-phenyl]-piperidin-3-yl}-methanone;

{(R)-1-[4-Chloro-3-(5-methyl-1H-benzoimidazol-2-yl)-phenyl]-piperidin-3-yl}-(3-dimethylamino-pyrrolidin-1-yl)-methanone;

{1-[4-Chloro-3-(5-methoxy-1H-benzoimidazol-2-yl)-phenyl]-pyrrolidin-3-yl}-morpholin-4-yl-methanone;

(3-Dimethylamino-pyrrolidin-1-yl)-{1-[3-(1-methyl-1H-benzoimidazol-2-yl)-phenyl]-pyrrolidin-3-yl}-methanone;

{(R)-1-[4-Chloro-3-(5-fluoro-1H-benzoimidazol-2-yl)-phenyl]-piperidin-3-yl}-(3-dimethylamino-pyrrolidin-1-yl)-methanone, {(R)-1-[3-(1H-Benzoimidazol-2-yl)-4-chloro-phenyl]-piperidin-3-yl}-(3-dimethylamino-pyrrolidin-1-yl)-methanone;

{(R)-1-[4-Chloro-3-(5-methyl-1H-benzoimidazol-2-yl)-phenyl]-piperidin-3-yl}-morpholin-4-yl-methanone;

{1-[4-Chloro-3-(5-methyl-1H-benzoimidazol-2-yl)-phenyl]-pyrrolidin-3-yl}-(3-dimethylamino-pyrrolidin-1-yl)-methanone, {(S)-1-[4-Chloro-3-(5-fluoro-1H-benzoimidazol-2-yl)-phenyl]-piperidin-3-yl}-morpholin-4-yl-methanone, {(S)-1-[3-(1H-Benzoimidazol-2-yl)-4-chloro-phenyl]-piperidin-3-yl}-(3-dimethylamino-pyrrolidin-1-yl)-methanone;

{1-[4-Chloro-3-(-1H-imidazo[4,5-c]pyridin-2-yl)-phenyl]-piperidin-4-yl}-morpholin-4-yl-methanone, {(R)-1-[4-Chloro-3-(-1H-imidazo[4,5-c]pyridin-2-yl)-phenyl]-piperidin-3-yl}-morpholin-4-yl-methanone;

{(S)-1-[4-Chloro-3-(-1H-imidazo[4,5-c]pyridin-2-yl)-phenyl]-piperidin-3-yl}-morpholin-4-yl-methanone;

{1-[4-Chloro-3-(-1H-imidazo[4,5-c]pyridin-2-yl)-phenyl]-piperidin-4-yl}-(3-dimethylamino-pyrrolidin-1-yl)-methanone;

{(S)-1-[3-(1H-Benzoimidazol-2-yl)-4-chloro-phenyl]-piperidin-3-yl}-(3-dimethylamino-pyrrolidin-1-yl)-methanone, {1-[4-Chloro-3-(5-fluoro-1H-benzoimidazol-2-yl)-phenyl]-piperidin-4-yl}-morpholin-4-yl-methanone, {1-[4-Chloro-3-(5-fluoro-1H-benzoimidazol-2-yl)-phenyl]-piperidin-4-yl}-(3-dimethylamino-pyrrolidin-1-yl)-methanone; and {1-[4-Chloro-3-(5-methyl-1H-benzoimidazol-2-yl)-phenyl]-piperidin-4-yl}-morpholin-4-yl-methanone, or a pharmaceutically acceptable salt thereof.

16. A pharmaceutical composition containing a compound according to claim 1 with a pharmaceutically acceptable carrier or excipient.

17. A method for treating osteoporosis comprising administering a pharmaceutical composition comprising a compound according to claim 1.

* * * * *